(12) United States Patent
Walker et al.

(10) Patent No.: US 12,258,679 B2
(45) Date of Patent: *Mar. 25, 2025

(54) POLYCLONAL MIXTURES OF ANTIBODIES, AND METHODS OF MAKING AND USING THEM

(71) Applicant: Adimab, LLC, Lebanon, NH (US)

(72) Inventors: Laura M. Walker, Lebanon, NH (US); Eric Krauland, Lebanon, NH (US); Karl Dane Wittrup, Lebanon, NH (US)

(73) Assignee: Adimab, LLC, Lebanon, NH (US)

(*) Notice: Subject to any disclaimer, the term of this patent is extended or adjusted under 35 U.S.C. 154(b) by 165 days.

This patent is subject to a terminal disclaimer.

(21) Appl. No.: 17/838,458

(22) Filed: Jun. 13, 2022

(65) Prior Publication Data
US 2023/0071129 A1  Mar. 9, 2023

Related U.S. Application Data

(60) Continuation of application No. 16/844,255, filed on Apr. 9, 2020, now Pat. No. 11,390,964, which is a (Continued)

(51) Int. Cl.
C40B 30/04 (2006.01)
C07K 16/00 (2006.01)
G01N 33/68 (2006.01)

(52) U.S. Cl.
CPC .............. *C40B 30/04* (2013.01); *C07K 16/00* (2013.01); *C07K 16/005* (2013.01);
(Continued)

(58) Field of Classification Search
None
See application file for complete search history.

(56) References Cited

U.S. PATENT DOCUMENTS 10,684,289 B2  6/2020  Walker et al.
11,390,964 B2  7/2022  Walker et al.
(Continued)

FOREIGN PATENT DOCUMENTS

CA  2175482 A1  6/1995
WO  WO-95/15982 A2  6/1995
(Continued)

OTHER PUBLICATIONS

Bostrom, J. et al., Improving antibody binding affinity and specificity for therapeutic development, Methods Mol Biol., 525:353-76, xiii (2009).
(Continued)

*Primary Examiner* — Christian C Boesen
(74) *Attorney, Agent, or Firm* — Choate, Hall & Stewart LLP; Brenda Herschbach Jarrell; Meaghan E. Bychowski

(57) ABSTRACT

A method of broadening epitopic coverage of an antigen of interest, wherein a first sample of the antigen of interest is contacted with a first plurality of host cells collectively expressing a first library of antibodies. Host cells expressing antibodies that bind to the antigen are then collected from among the first plurality of host cells, and a composition is prepared comprising a polyclonal mixture of antibodies expressed by these host cells. A second sample of the antigen of interest is then contacted with an aliquot of the prepared composition and a second plurality of host cells collectively expressing a second library of antibodies. Host cells expressing antibodies that bind to the second sample of the antigen are then collected from among the second plurality of host cells.

16 Claims, 18 Drawing Sheets

Specification includes a Sequence Listing.

Related U.S. Application Data division of application No. 15/102,312, filed as application No. PCT/US2014/069357 on Dec. 9, 2014, now Pat. No. 10,684,289.

(60) Provisional application No. 61/913,855, filed on Dec. 9, 2013.

(52) U.S. Cl.
CPC ..... *G01N 33/6854* (2013.01); *G01N 33/6878* (2013.01); *C07K 2317/10* (2013.01)

(56) References Cited

U.S. PATENT DOCUMENTS

| | | |
|---|---|---|
| 2012/0141463 A1 | 6/2012 | Wu et al. |
| 2013/0085072 A1 | 4/2013 | Bradbury et al. |
| 2016/0313345 A1 | 10/2016 | Walker et al. |
| 2020/0278354 A1 | 9/2020 | Walker et al. |

FOREIGN PATENT DOCUMENTS

| | | |
|---|---|---|
| WO | WO-2004/021013 A1 | 3/2004 |
| WO | WO-2012/066129 A1 | 5/2012 |
| WO | WO-2015/089080 A2 | 6/2015 |

OTHER PUBLICATIONS

Bostrom, J. et al., Variants of the antibody herceptin that interact with HER2 and VEGF at the antigen binding site, Science, 323(5921):1610-4 (2009).

Delano, WL et al., Convergent solutions to binding at a protein-protein interface, Science, 287(5456):1279-83 (2000).

Deng, L. et al., Structural evidence for a bifurcated mode of action in the antibody-mediated neutralization of hepatitis C virus, Proc Natl Acad Sci USA, 110(18):7418-22 (2013).

Ditzel, H. et al., Neutralizing Recombinant Human Antibodies to a Conformational V2- and CD4-Binding Site-Sensitive Epitope of HIV-1 gp120 Isolated by Using an Epitope-Masking Procedure, The Journal of Immunology, 154:893-906 (1995).

Ekiert, DC and Wilson, IA, Broadly neutralizing antibodies against influenza virus and prospects for universal therapies, Curr Opin Virol., 2(2):134-41 (2012).

Fagete, S. et al., Dual specificity of anti-CXCL10-CXCL9 antibodies is governed by structural mimicry, J Biol Chem., 287(2):1458-67 (2012).

Felding-Habermann, B. et al., Combinatorial antibody libraries from cancer patients yield ligand-mimetic Arg-Gly-Asp-containing immunoglobulins that inhibit breast cancer metastasis, Proc Natl Acad Sci USA, 101(49):17210-5 (2004).

Garcia-Rodriquez, C et al., Neutralizing human monoclonal antibodies binding multiple serotypes of botulinum neurotoxin, Protein Eng Des Sel., 24(3):321-31 (2011).

International Search Report for PCT/US14/69357, 4 pages (Jul. 2, 2015).

Kong, L. et al., Structural basis of hepatitis C virus neutralization by broadly neutralizing antibody HCV1, Proc Natl Acad Sci USA, 109(24):9499-504 (2012).

Kwong, PD and Wilson, IA, HIV-1 and influenza antibodies: seeing antigens in new ways, Nat Immunol., 10(6):573-8 (2009).

Kwong, PD and Mascola, JR, Human antibodies that neutralize HIV-1: identification, structures, and B cell ontogenies, Immunity, 37(3):412-25 (2012).

Pavoor, TV et al., An enhanced approach for engineering thermally stable proteins using yeast display, Protein Eng Des Sel., 25(10):625-30 (2012).

Schaefer, G. et al., A two-in-one antibody against HER3 and EGFR has superior inhibitory activity compared with monospecific antibodies, Cancer Cell, 20(4):472-86 (2011).

Traxlmayr, MW, et al., Directed evolution of Her2/neu-binding IgG1-Fc for improved stability and resistance to aggregation by using yeast surface display, Protein Eng Des Sel., 26(4):255-65 (2013).

Tsui, P. et al., Progressive epitope-blocked panning of a phage library for isolation of human RSV antibodies, Journal of Immunological Methods, 263:123-132 (2002).

Written Opinion for PCT/US14/69357, 22 pages (Jul. 2, 2015).

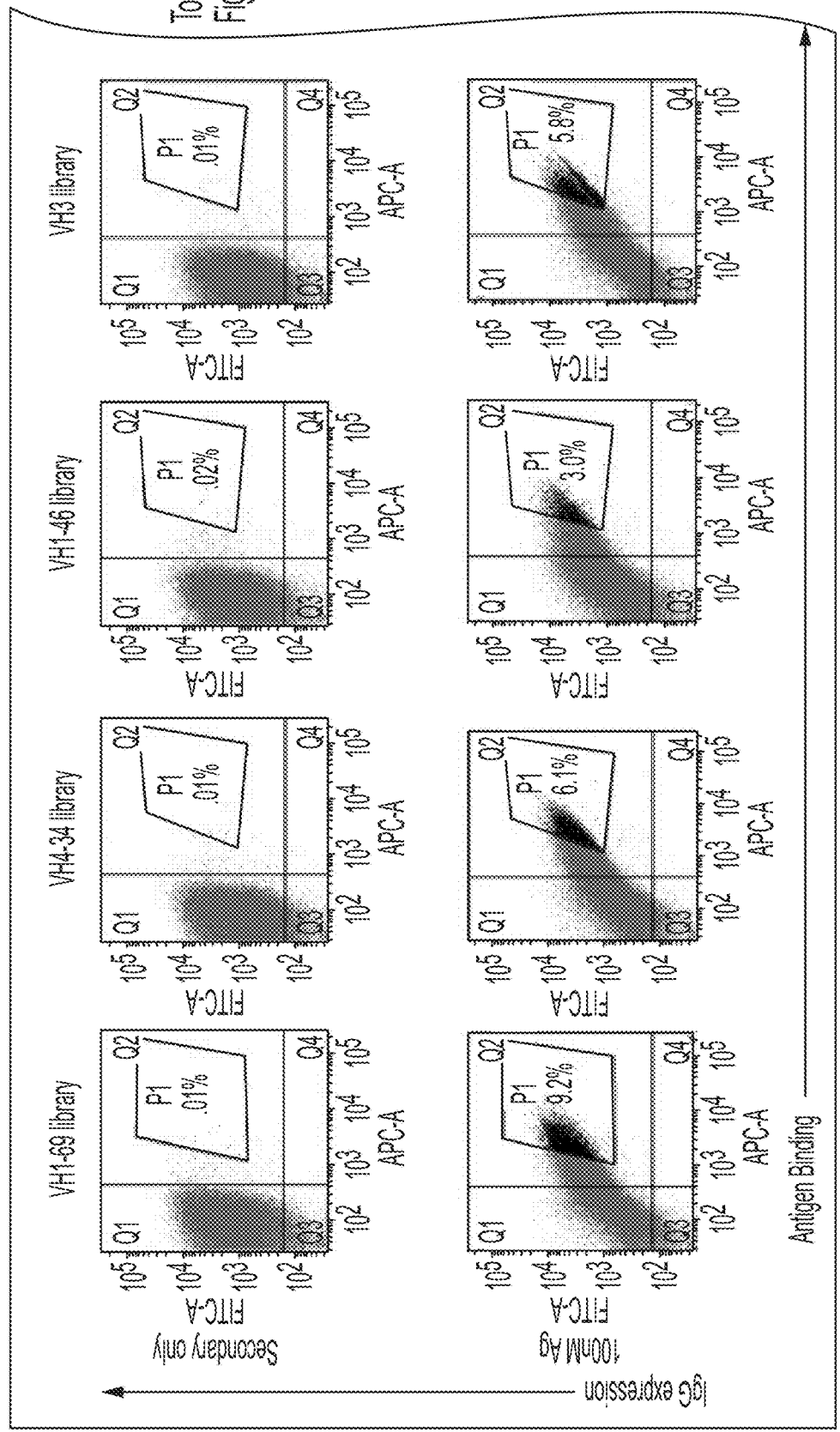

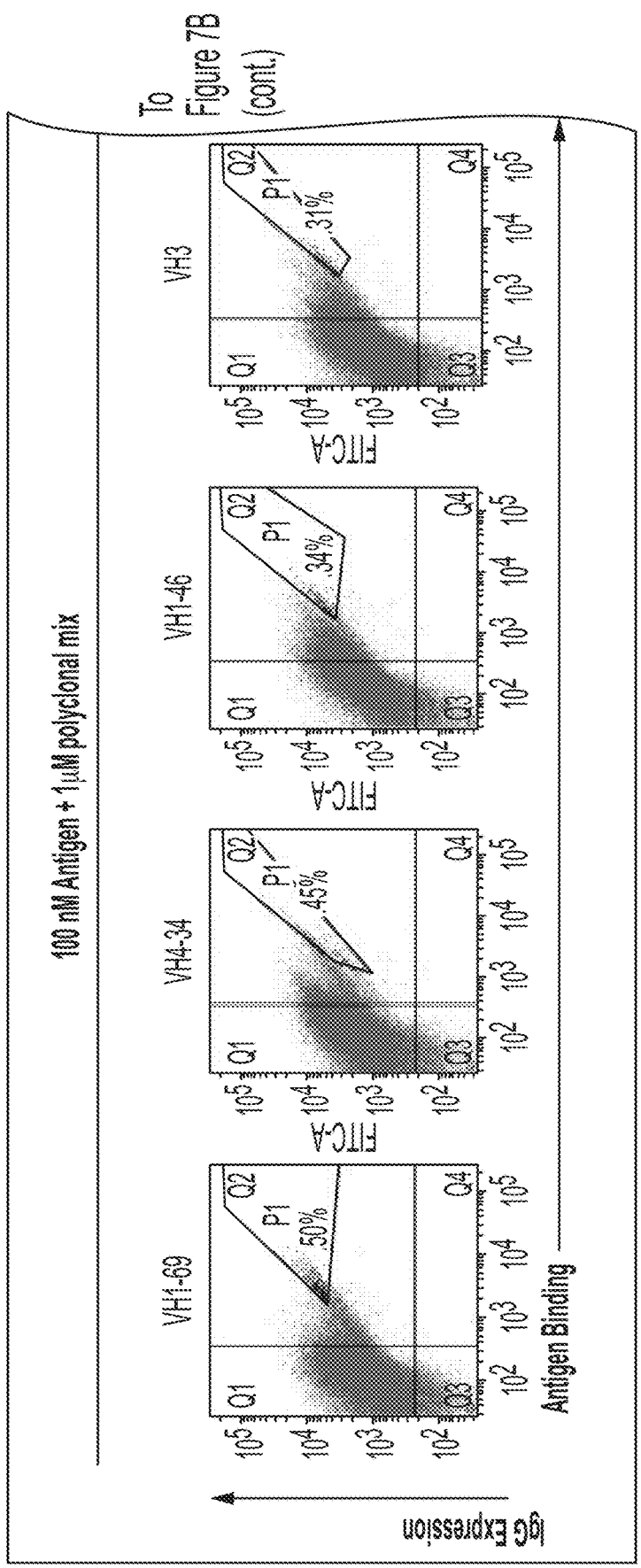

Figure 11

| Library Name | Heavy Chain Germline | Light Chain Germline |
|---|---|---|
| VH1-23 | VH1-23 | 8 Vk Mix^ |
| VH1-69 | VH1-69 | 8 Vk Mix |
| VH1-46 | VH1-46 | 8 Vk Mix |
| VH4-39 | VH4-39 | 8 Vk Mix |
| VH4-34 | VH4-34 | 8 Vk Mix |
| VH3 | VH3-9, VH3-30/33, VH3-07, VH3-48, VH3-21, VH3-72* | 8 Vk Mix |
| VH1/5 | VH1-2, VH1-18, VH5-51* | 8 Vk Mix |
| VH3/4 | VH3-66, VH4-31, VH4-61, VH4-59, VH4-b* | 8 Vk Mix |

*All germlines are represented equally
^Vk1-05, Vk1-12, Vk1-33, Vk1-39, Vk2-28, Vk3-11, Vk3-15, Vk3-20. All germlines are represented equally.

POLYCLONAL MIXTURES OF ANTIBODIES, AND METHODS OF MAKING AND USING THEM

RELATED APPLICATIONS

This application is a continuation of U.S. patent application Ser. No. 16/844,255, which is a division of U.S. patent application Ser. No. 15/102,312, filed Jun. 7, 2016, which is a 35 U.S.C. § 371 National Phase Entry Application of International Application No. PCT/US2014/069357 filed Dec. 9, 2014, which claims priority from U.S. provisional patent application Ser. No. 61/913,855, entitled "Polyclonal Mixtures of Antibodies, and Methods of Making and Using Them", filed on Dec. 9, 2013, each of which are hereby incorporated herein by reference in their entirety for all purposes.

SEQUENCE LISTING

In accordance with 37 CFR 1.52 (e) (5), a Sequence Listing in the form of an ASCII text file (entitled "2009186-0360_SL.txt," created on Jun. 12, 2022, and 3,504 bytes in size) is incorporated herein by reference in its entirety.

FIELD OF THE INVENTION

The present invention relates, inter alia, to polyclonal mixtures of antibodies, and methods of making and using them.

BACKGROUND OF THE INVENTION

All references, including patents, patent applications, and non-patent publications, cited throughout are hereby expressly incorporated by reference in their entireties for all purposes.

Antibody display technologies, such as phage and yeast display, have proven powerful alternatives to natural antibodies for generating high affinity antibodies for therapeutics and diagnostics (Bradbury et al., 2011, Feldhaus et al., 2003, Fuh, 2007, Hanes et al., 2000, Hoogenboom, 2005, Winter et al., 1994). There are several advantages of in vitro technologies compared to traditional hybridoma systems, including the ability to simultaneously screen very large numbers of antibodies for binding to antigens of interest, overcome immunological tolerance, and further mature selected antibodies to higher affinities than can be achieved in vivo (see, e.g., Boder et al., 2000, Boder et al., 1997, Bostrom et al., 2009, Bostrom et al., 2009, Garcia-Rodriguez et al., 2011, Hanes, et al., 2000, and Lou et al., 2010). One of the more significant advantages of antibody library technology is the ability to control selection conditions to preferentially select for binders with desirable properties. For instance, a number of methods have been employed in order to enrich for high affinity clones, such as lowered antigen concentrations, increased washing stringency, and the inclusion of unlabeled antigen to pressure clones with fast dissociation rates (see, e.g., Boder, et al., 2000, Bostrom, et al., 2009, Hawkins et al., 1992, and Winter, et al., 1994). Selections can also be performed at high temperatures or in the presence of chaotropic agents to enrich for clones with high thermostability (see, e.g., Pavoor et al., 2012, and Traxlmayr et al., 2013). In addition, cross-reactive clones can be recovered by performing sequential selections with related antigens (see, e.g., Bostrom, et al., 2009, Fagete et al., 2012, Garcia-Rodriguez, et al., 2011, Schaefer et al., 2011).

One of the more definitive feature of an antibody is its epitope(s), which stereospecifically determine(s) any functional activity of the antibody/antigen complex (see, e.g., Deng et al., 2013, Ekiert et al., 2012, Felding-Habermann et al., 2004, Kong et al., 2012, Kwong et al., 2012, and Kwong et al., 2009). When available, lead antibodies or ligands that target a desired epitope allows these reagents to be used as competitors during selections to enrich for clones of cross-blocking specificity. However, as is often the case such control reagents are unavailable and/or the identity, nature, and/or number of functional epitopes on an antigen of interest is not known, it is desirable—indeed, often necessary—to isolate and characterize antibodies against a broad range of different epitopes in order to screen for functional clones. Unfortunately, however, many protein antigens often contain one or more highly antigenic epitopes (see, e.g., DeLano et al., 2000) that make the search for clones targeting rarer epitopes a time-consuming, laborious and expensive process dominated by large numbers of binders to one or a few dominant epitopes only.

Accordingly, there is a need for the provision of reagents and methods which allow for a more comprehensive interrogation of the full repertoire of epitopes available on antigens of interest, particularly in such cases where there is little or no prior knowledge of the epitopic diversity of such antigens. Such reagents and methods would advantageously thus facilitate the isolation and/or identification of collections of antibodies containing members with epitopic specificities that, are collectively, more reflective of the epitopic diversity of such antigens of interest than other methods in the art.

SUMMARY OF THE INVENTION

Applicants have discovered and developed reagents methods to more efficiently and more productively interrogate antibody repertoires for antibodies against an antigen of interest by, inter alia, broadening of epitopic coverage of the antigen of interest, normalizing epitopic coverage of the antigen of interest, reducing selection bias towards (a) dominant epitope(s) of the antigen of interest, blocking (a) dominant epitope(s) of the antigen of interest, identifying (a) rare or under-represented epitope(s) of the antigen of interest, enriching for antibodies with specificity toward (a) rare or under-represented epitope(s) of the antigen of interest, and identifying antibodies with specificity toward (a) rare or under-represented epitope(s) of the antigen of interest. The inventive reagents and methods disclosed throughout allow for the recovery of large numbers of clones against rare epitopes that are not rescued in practical abundance using prior library selection protocols. Advantageously, the aforementioned benefits may be realized when employing the inventive reagents and methods without requiring any prior knowledge of epitopic coverage or diversity of the antigen of interest.

Accordingly, in certain embodiments, provided are methods of broadening epitopic coverage of an antigen of interest, the method comprising:
 a) contacting a first sample of the antigen of interest with a first library of antibodies;
 b) collecting antibodies that bind to the antigen from among the first sample employed in step a);
 c) preparing a composition comprising a polyclonal mixture of antibodies collected in step b);

d) contacting a second sample of the antigen of interest with an aliquot of the composition prepared in step c) and a second library of antibodies; and e) after performing step d), collecting antibodies that bind to the second sample of the antigen from among the second library of antibodies employed in the contacting step d);

wherein an increase in the number of different epitopes collectively recognized by the antibodies collected in step e) relative to the number of different epitopes collectively recognized by the antibodies contained in the composition prepared in step b) indicates that epitopic coverage of the antigen has been broadened.

In certain embodiments, optionally in combination with any of the preceding or following embodiments, provided are methods of normalizing epitopic coverage of an antigen of interest, the method comprising:

a) contacting a first sample of the antigen of interest with a first library of antibodies;

b) collecting antibodies that bind to the antigen from among the first library of antibodies employed in step a);

c) preparing a composition comprising a polyclonal mixture of antibodies collected in step b);

d) contacting a second sample of the antigen of interest with an aliquot of the composition prepared in step c) and a second library of antibodies;

e) after performing step d), collecting antibodies that bind to the second sample of the antigen from among the second library of antibodies employed in the contacting step d), wherein either:
i) an increase in the number of different antibodies collected in step e) that bind to at least one under-represented epitope relative to the number of different antibodies contained in the composition prepared in step c) that bind the at least one under-represented epitope;
ii) a decrease in the number of different antibodies collected in step e) that bind to at least one over-represented epitope relative to the number of different antibodies contained in the composition prepared in step c) that bind the at least one over-represented epitope; or
iii) both i) and ii);

indicates that the epitopic coverage of the antigen of interest has been normalized.

In certain embodiments, optionally in combination with any of the preceding or following embodiments, provided are methods of reducing selection bias towards at least one dominant epitope of an antigen of interest, the method comprising:

a) contacting a first sample of the antigen of interest with a first library of antibodies;

b) collecting antibodies that bind to the antigen from among the first library of antibodies employed in step a);

c) preparing a composition comprising a polyclonal mixture of antibodies collected in step b), wherein the composition comprises at least one antibody that recognizes at least one epitope of the antigen;

d) contacting a second sample of the antigen of interest with an aliquot of the composition prepared in step c) and a second library of antibodies;

wherein the at least one epitope is made less available for binding by antibodies contained in the second plurality of antibodies as a result of contacting the second sample of the antigen of interest with the composition prepared in step c), thereby reducing bias towards the at least one epitope on the antigen.

In certain embodiments, optionally in combination with any of the preceding or following embodiments, provided are methods of blocking at least one dominant epitope of an antigen of interest, the method comprising:

a) contacting a first sample of the antigen of interest with a first library of antibodies;

b) collecting antibodies that bind to the antigen from among the first library of antibodies employed in step a);

c) preparing a composition comprising a polyclonal mixture of antibodies collected in in step b), wherein the composition comprises at least one antibody that recognizes at least one dominant epitope on the antigen;

d) contacting a second sample of the antigen of interest with an aliquot of the composition prepared in step c) and a second library of antibodies;

wherein the at least one dominant epitope is blocked by the at least one antibody in the mixture prepared in step c).

In certain embodiments, optionally in combination with any of the preceding or following embodiments, provided are methods of identifying at least one antibody with specificity for a rare epitope on an antigen of interest, the method comprising:

a) contacting a first sample of the antigen of interest with a first library of antibodies;

b) collecting antibodies that bind to the antigen from among the first library of antibodies employed in step a);

c) preparing a composition comprising a polyclonal mixture of antibodies collected in step b), wherein the composition comprises at least one antibody that recognizes at least one dominant epitope on the antigen;

d) contacting a second sample of the antigen of interest with an aliquot of the composition prepared in step c) and a second library of antibodies;

e) after performing step d), collecting at least antibody from the second library of antibodies that binds to the rare epitope.

In certain embodiments, optionally in combination with any of the preceding or following embodiments, provided are methods of identifying at least one antibody with specificity for a rare epitope on an antigen, the method comprising:

a) contacting a first sample of the antigen of interest with a first library of antibodies;

b) collecting antibodies that bind to the antigen from among the first library of antibodies employed in step a);

c) preparing a composition comprising a polyclonal mixture of antibodies collected in step b), wherein the composition comprises at least one antibody that recognizes at least one dominant epitope on the antigen;

d) contacting a second sample of the antigen of interest with an aliquot of the composition prepared in step c) and a second library of antibodies;

e) after performing step d), identifying at least one antibody from among the second sample of antibodies having specificity for an epitope that is under-represented in the composition prepared in step c). In certain embodiments of such methods, the at least one antibody that is identified in step e) constitutes an antibody that has specificity toward a rare epitope on the antigen of interest.

In certain embodiments, optionally in combination with any of the preceding or following embodiments, provided are methods of enriching for antibodies having specificity towards at least one rare epitope of an antigen in an antibody selection process, the method comprising:
  a) contacting a first sample of the antigen of interest with a first library of antibodies;
  b) collecting antibodies that bind to the antigen from among the first library of antibodies employed in step a);
  c) preparing a composition comprising a polyclonal mixture of antibodies collected in step b), wherein the composition comprises at least one antibody that recognizes at least one dominant epitope on the antigen;
  d) contacting a second sample of the antigen of interest with an aliquot of the composition prepared in step c) and a second library of antibodies, thereby blocking the at least one dominant epitope;
  e) after performing step d), collecting antibodies from among the second library of antibodies with specificity to the at least one rare epitope;
  wherein the number of different antibodies having specificity to the at least one rare epitope collected in step e) is greater than the number of antibodies having specificity to the at least one rare epitope collected in step b).

In certain embodiments, the libraries of antibodies employed in any of the aforementioned embodiments are expressed by pluralities of host cells. Accordingly, in certain embodiments, optionally in combination any of the preceding or following embodiments, provided are methods of broadening epitopic coverage of an antigen of interest, the method comprising:
  a) contacting a first sample of the antigen of interest with a first plurality of host cells collectively expressing a first library of antibodies;
  b) collecting host cells expressing antibodies that bind to the antigen from among the first plurality of host cells employed in step a);
  c) preparing a composition comprising a polyclonal mixture of antibodies expressed by host cells collected in step b);
  d) contacting a second sample of the antigen of interest with an aliquot of the composition prepared in step c) and a second plurality of host cells collectively expressing a second library of antibodies; and
  e) after performing step d), collecting host cells from among the second plurality of host cells expressing antibodies that bind to the second sample of the antigen from among the second plurality of host cells;
  wherein an increase in the number of different epitopes collectively recognized by the antibodies expressed by the host cells collected in step e) relative to the number of different epitopes collectively recognized by the antibodies contained in the composition prepared in step b) indicates that epitopic coverage of the antigen has been broadened.

In certain embodiments, optionally in combination any of the preceding or following embodiments, provided are methods of normalizing epitopic coverage of an antigen of interest, the method comprising:
  a) contacting a first sample of the antigen of interest with a first plurality of host cells collectively expressing a first library of antibodies;
  b) collecting host cells expressing antibodies that bind to the antigen from among the first plurality of cells employed in step a);
  c) preparing a composition comprising a polyclonal mixture of antibodies expressed by host cells collected in step b);
  d) contacting a second sample of the antigen of interest with an aliquot of the composition prepared in step c) and a second plurality of host cells collectively expressing a second library of antibodies;
  e) after performing step d), collecting host cells from among the second plurality of host cells expressing antibodies that bind to the second sample of the antigen from among the second plurality of host cells,
  wherein either:
  i) an increase in the number of different antibodies expressed by the host cells collected in step e) that bind to at least one under-represented epitope relative to the number of different antibodies contained in the composition prepared in step c) that bind the at least one under-represented epitope;
  ii) a decrease in the number of different antibodies expressed by the host cells collected in step e) that bind to at least one over-represented epitope relative to the number of different antibodies contained in the composition prepared in step c) that bind the at least one over-represented epitope; or
  iii) both i) and ii);
  indicates that the epitopic coverage of the antigen of interest has been normalized.

In certain embodiments, optionally in combination any of the preceding or following embodiments, provided are methods of reducing selection bias towards at least one dominant epitope of an antigen of interest, the method comprising:
  a) contacting a first sample of the antigen of interest with a first plurality of host cells collectively expressing a first library of antibodies;
  b) collecting host cells expressing antibodies that bind to the antigen from among the first plurality of cells employed in step a);
  c) preparing a composition comprising a polyclonal mixture of antibodies expressed by host cells collected in step b), wherein the composition comprises at least one antibody that recognizes at least one epitope on the antigen;
  d) contacting a second sample of the antigen of interest with an aliquot of the composition prepared in step c) and a second plurality of host cells collectively expressing a second library of antibodies;
  wherein the at least one epitope is made less available for binding by antibodies contained in the second plurality of antibodies as a result of contacting the second sample of the antigen of interest with the composition prepared in step c), thereby reducing bias towards the at least one epitope on the antigen.

In certain embodiments, optionally in combination any of the preceding or following embodiments, provided are methods of blocking at least one dominant epitope of an antigen of interest, the method comprising:
  a) contacting a first sample of the antigen of interest with a first plurality of host cells collectively expressing a first library of antibodies;
  b) collecting host cells expressing antibodies that bind to the antigen from among the first plurality of cells employed in step a);
  c) preparing a composition comprising a polyclonal mixture of antibodies expressed by host cells collected in in step b), wherein the composition comprises at least one antibody that recognizes at least one dominant epitope on the antigen;

d) contacting a second sample of the antigen of interest with an aliquot of the composition prepared in step c) and a second plurality of host cells collectively expressing a second library of antibodies;

wherein the at least one dominant epitope is blocked by the at least one antibody in the mixture prepared in step c).

In certain embodiments, optionally in combination any of the preceding or following embodiments, provided are methods of identifying at least one host cell that expresses an antibody with specificity for a rare epitope on an antigen of interest, the method comprising:

a) contacting a first sample of the antigen of interest with a first plurality of host cells collectively expressing a first library of antibodies;

b) collecting host cells expressing antibodies that bind to the antigen from among the first plurality of cells employed in step a);

c) preparing a composition comprising a polyclonal mixture of antibodies expressed by host cells collected in step b), wherein the composition comprises at least one antibody that recognizes at least one dominant epitope on the antigen;

d) contacting a second sample of the antigen of interest with an aliquot of the composition prepared in step c) and a second plurality of host cells collectively expressing a second library of antibodies;

e) after performing step d), collecting at least one host cell from among the second plurality of host cells that expresses an antibody that binds to the rare epitope, thereby identifying the at least one host cell that expresses the antibody with specificity for the rare epitope.

In certain embodiments, optionally in combination any of the preceding or following embodiments, provided are methods of identifying at least one antibody with specificity for a rare epitope on an antigen, the method comprising:

a) contacting a first sample of the antigen of interest with a first plurality of host cells collectively expressing a first library of antibodies;

b) collecting host cells expressing antibodies that bind to the antigen from among the first plurality of cells employed in step a);

c) preparing a composition comprising a polyclonal mixture of antibodies expressed by host cells collected in step b), wherein the composition comprises at least one antibody that recognizes at least one dominant epitope on the antigen;

d) contacting a second sample of the antigen of interest with an aliquot of the composition prepared in step c) and a second plurality of host cells collectively expressing a second library of antibodies;

e) after performing step d), identifying at least one antibody expressed by at least one host cell from among the second plurality of host cells having specificity for an epitope that is under-represented in the composition prepared in step c). In certain embodiments of such methods, the at least one antibody that is identified in step e) constitutes an antibody that has specificity toward a rare epitope on the antigen of interest.

In certain embodiments, optionally in combination any of the preceding or following embodiments, provided are methods of enriching for antibodies having specificity towards at least one rare epitope of an antigen in an antibody selection process, the method comprising:

a) contacting a first sample of the antigen of interest with a first plurality of host cells collectively expressing a first library of antibodies;

b) collecting host cells expressing antibodies that bind to the antigen from among the first plurality of cells employed in step a);

c) preparing a composition comprising a polyclonal mixture of antibodies expressed by host cells collected in step b), wherein the composition comprises at least one antibody that recognizes at least one dominant epitope on the antigen;

d) contacting a second sample of the antigen of interest with an aliquot of the composition prepared in step c) and a second plurality of host cells collectively expressing a second library of antibodies, thereby blocking the at least one dominant epitope;

e) after performing step d), collecting host cells from among the second plurality of host cells that express antibodies with specificity to the at least one rare epitope;

wherein the number of different antibodies having specificity to the at least one rare epitope expressed from host cells collected in step e) is greater than the number of antibodies having specificity to the at least one rare epitope expressed from host cells collected in step b).

In certain embodiments, optionally in combination with any of the preceding or following embodiments, the first and second libraries of antibodies of antibodies comprise the same antibodies.

In certain embodiments, optionally in combination with any of the preceding or following embodiments, the first and second samples consist essentially of the same antibodies.

In certain embodiments, optionally in combination with any of the preceding or following embodiments, the first and second samples consist of the same antibodies.

In certain embodiments, optionally in combination with any of the preceding or following embodiments, the second library of antibodies comprises a subset of antibodies contained in the first library of antibodies.

In certain embodiments, optionally in combination with any of the preceding or following embodiments, the second library of antibodies comprises antibodies that are contained in the first library of antibodies as well as antibodies that are not contained in the first library of antibodies.

In certain embodiments, optionally in combination with any of the preceding or following embodiments, one or both of the first and second libraries of antibodies each comprise one or more sub-libraries.

In certain embodiments, optionally in combination with any of the preceding or following embodiments, one or more sub-libraries are physically are separated from one another.

In certain embodiments, optionally in combination with any of the preceding or following embodiments, the antibodies comprise: full length immunoglobulins; full length IgGs; full length IgMs; full length IgEs; full length IgAs; variable domains, antibody fragments; linear antibodies, single chain antibodies; scFvs, Fv fragments; Fab fragments, Fab' fragments, (Fab')$_2$ fragments; multispecific antibodies; bispecific antibodies; trispecific antibodies; tetraspecific antibodies; humanized antibodies; and combinations thereof.

In certain embodiments, optionally in combination with any of the preceding or following embodiments, at least one of the collecting or identifying steps comprises employing flow cytometry.

In certain embodiments, optionally in combination with any of the preceding or following embodiments, at least one of the collecting or identifying steps comprises employing florescence-activated cell sorting (FACS).

In certain embodiments, optionally in combination with any of the preceding or following embodiments, at least one of the collecting or identifying steps comprises employing magnetic assisted cell sorting (MACS).

In certain embodiments, optionally in combination with any of the preceding or following embodiments, the host cells are prokaryotic cells.

In certain embodiments, optionally in combination with any of the preceding or following embodiments, the host cells are bacterial cells.

In certain embodiments, optionally in combination with any of the preceding or following embodiments, the host cells are *E. coli* cells.

In certain embodiments, optionally in combination with any of the preceding or following embodiments, the host cells are eukaryotic cells.

In certain embodiments, optionally in combination with any of the preceding or following embodiments, the host cells are yeast cells.

In certain embodiments, optionally in combination with any of the preceding or following embodiments, the host cells are *Saccharomyces cerevisiae* cells In certain embodiments, optionally in combination with any of the preceding or following embodiments, the host cells are *Pichia pastoris* cells.

In certain embodiments, optionally in combination with any of the preceding or following embodiments, the host cells are mammalian cells.

In certain embodiments, optionally in combination with any of the preceding or following embodiments, either: the first library of antibodies; the second library of antibodies; or the first library of antibodies and the second library of antibodies; comprises a phage library.

In certain embodiments, optionally in combination with any of the preceding or following embodiments, either: the first library of antibodies; the second library of antibodies; or the first library of antibodies and the second library of antibodies; comprises a yeast presentation library.

In certain embodiments, optionally in combination with any of the preceding or following embodiments the first plurality of host cells and the second plurality of host cells are each transformed with a first library of polynucleotides and a second library of polynucleotides, each of which collectively encode the first library of antibodies and the second library of antibodies, respectively.

In certain embodiments, optionally in combination with any of the preceding or following embodiments the host cells collectively express the library of antibodies and present the antibodies on their cell surfaces.

In certain embodiments, provided are collections of antibodies obtained by performing any of the preceding or following methods.

In certain embodiments, provided are antibodies obtained by performing any of the preceding or following methods.

In certain embodiments, optionally in combination of any of the preceding or following embodiments, provided are polyclonal mixtures of antibodies prepared by a method comprising:
a) contacting an antigen of interest with a plurality of host cells collectively expressing a first library of antibodies;

b) collecting host cells expressing antibodies that bind to the antigen from among the plurality of host cells employed in step a);

c) preparing a composition comprising a polyclonal mixture of antibodies expressed by host cells collected in step b).

In certain embodiments, optionally in combination of any of the preceding or following embodiments, provided are polyclonal mixtures of antibodies prepared by a method comprising:
a) contacting an antigen of interest with a library of antibodies;

b) collecting antibodies that bind to the antigen from among the library of antibodies employed in step a);

c) preparing a composition comprising a polyclonal mixture of antibodies from the antibodies collected in step b).

In certain embodiments, provided are polyclonal mixtures of antibodies for use in any of the preceding or following methods.

In certain embodiments, provided are uses of a polyclonal mixtures of antibodies in any of the preceding or following methods.

In certain embodiments, provided are libraries of antibody heavy chains comprising antibodies representing heavy chain germlines VH3-23, VH1-69, VH1-46, VH4-39, VH4-34, VH3-9, VH3-30, VH3-33, VH3-07, VH3-48, VH3-21, VH3-72, VH1-2, VH1-18, VH5-51, VH3-66, VH4-31, VH4-61, VH4-59, and VH4-b.

In certain embodiments, provided are libraries of antibody light chains comprising antibodies representing light chain germlines Vk1-05, Vk1-12 Vk1-33, Vk1-39, Vk2-28, Vk3-11. Vk3-15, and VK3-20.

In certain embodiments, provided are libraries of antibody heavy chains comprising antibodies representing:
heavy chain germlines VH3-23, VH1-69, VH1-46, VH4-39, VH4-34, VH3-9, VH3-30, VH3-33, VH3-07, VH3-48, VH3-21, VH3-72, VH1-2, VH1-18, VH5-51, VH3-66, VH4-31, VH4-61, VH4-59, and VH4-b; and light chain germlines Vk1-05, Vk1-12 Vk1-33, Vk1-39, Vk2-28, Vk3-11. Vk3-15, and VK3-20.

In certain embodiments, optionally in combination of any of the preceding or following embodiments, provided are libraries comprising, consisting essentially of, and/or consisting of: antibodies representing heavy chain germlines VH3-23, VH1-69, VH1-46, VH4-39, VH4-34, VH3-9, VH3-30, VH3-33, VH3-07, VH3-48, VH3-21, VH3-72, VH1-2, VH1-18, VH5-51, VH3-66, VH4-31, VH4-61, VH4-59, and VH4-b; antibodies representing light chain germlines Vk1-05, Vk1-12 Vk1-33, Vk1-39, Vk2-28, Vk3-11. Vk3-15, and VK3-20; antibodies representing heavy chain germlines VH3-23, VH1-69, VH1-46, VH4-39, VH4-34, VH3-9, VH3-30, VH3-33, VH3-07, VH3-48, VH3-21, VH3-72, VH1-2, VH1-18, VH5-51, VH3-66, VH4-31, VH4-61, VH4-59, and VH4-b; and light chain germlines Vk1-05, Vk1-12 Vk1-33, Vk1-39, Vk2-28, Vk3-11. Vk3-15, and VK3-20 for use in preparing polyclonal mixtures of antibodies. In certain such embodiments, such libraries are used in methods according to any one of the preceding or following methods.

BRIEF DESCRIPTION OF THE FIGURES

FIG. 1A and FIG. 1B depict the results of the fourth round of selections for antibodies that bind to an antigen of interest using the indicated antibody libraries by employing flow cytometry. Yeast host cells were double labeled so that antibody expression and antigen binding could be monitored simultaneously. The 2-D dot plots represent populations without (top) and with (bottom) antigen, respectively. The polygon gated populations represent double-positive yeast cells that were sorted (bottom). The percentages of antigen-positive cells are indicated in the top right corner of each plot.

FIG. 2A illustrates germline gene representation of unique IgGs from an initial round 4 output in the absence of a polyclonal mixture of antibodies, as described in the Examples and depicted in FIG. 1. FIG. 2B illustrates germline gene representation of the unique IgGs from round 4 selection outputs after employing the polyclonal antibody mixture blocking method as described in the Examples.

FIG. 4A illustrates epitope representation of unique clones from all eight germline libraries combined, as described in the Examples. FIG. 4B illustrates epitope representation of unique clones from individual germline libraries, as described in the Examples.

In FIG. 8A, epitopic coverage is depicted for all libraries combined, without the use of the polyclonal antibody mixtures (left column) and with the use of polyclonal antibody mixtures (right column), as described in the Examples. In FIG. 8B, epitopic coverage is depicted for each individual library, without the use of the polyclonal antibody mixtures (left columns) and with the use of polyclonal antibody mixtures (right columns), as described in the Examples. The results depicted in both FIG. 8A and FIG. 8B, demonstrate that re-interrogating libraries in the presence of polyclonal mixture of antibodies prepared from an initial selection employing those libraries, for example, reduces epitope bias towards dominant epitope(s), broadens epitopic coverage, normalizes epitopic coverage, reduces selection toward dominant epitopes, effects identification of rare epitope(s), enriches for antibodies having specificity to rare epitopes, and affords the identification of antibodies having specificity for rare epitopes.

FIG. 9A provides an epitopic representation based on the combined sequence outputs from all eight germline libraries tested as described in the Examples. FIG. 9B provides an epitopic representation based on sequence outputs from the eight tested libraries individually, as described in the Examples.

FIG. 11 provides the germline representation of the antibody heavy chain libraries and antibody light chain libraries employed in exemplary embodiments of the inventive methods, which exemplary embodiments are described in the Examples.

DETAILED DESCRIPTION OF EMBODIMENTS OF THE INVENTION

Figure 1B:
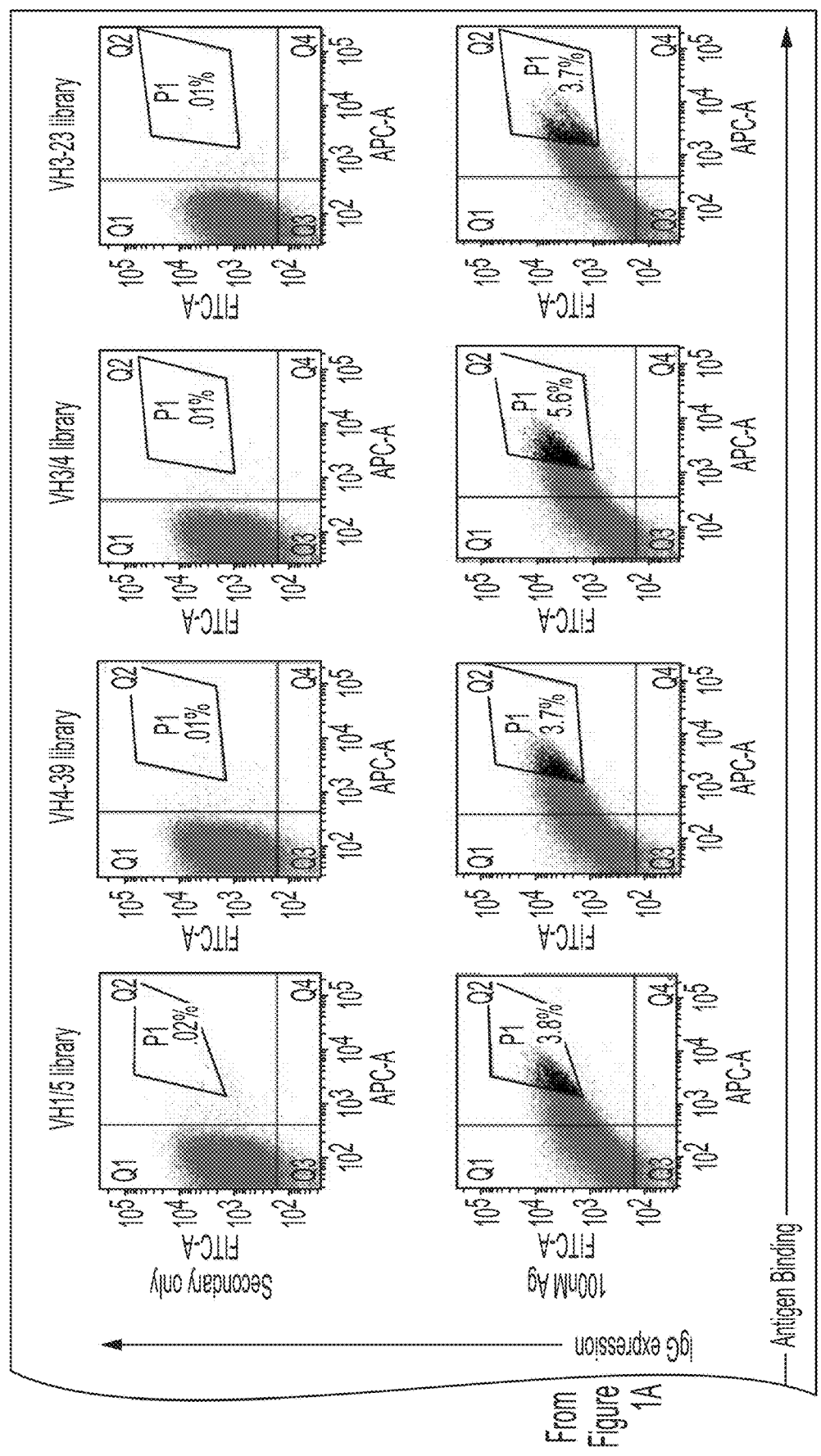

Applicants have now discovered, inter alia, reagents and methods that may be employed to more efficiently and more productively interrogate antibody libraries or repertoires for antibodies with specificity for antigens of interest. Importantly, the inventive reagents and methods disclosed herein, and the advantages that flow therefrom, for example, as disclosed throughout, may be realized without any prior knowledge concerning the epitopic nature or epitopic diversity of the antigen of interest.

The inventive reagents comprise compositions comprising polyclonal mixtures of antibodies that are prepared by contacting a first sample of an antigen of interest with a first library of antibodies, and then collecting antibodies from among the first library that bind to the antigen. Such compositions, or aliquots of such compositions, may then be contacted with a second sample of the antigen of interest along with a second library of antibodies, wherein the second library of antibodies may either: comprise the same antibodies as the first plurality of antibodies; comprise the same antibodies as the first plurality of antibodies in addition to antibodies that were not members of the first plurality of antibodies; comprise a subset of antibodies in the first plurality of antibodies; or comprise a subset of antibodies in the first plurality of antibodies in addition to antibodies that were not members of the first plurality of antibodies; and antibodies from among the second library of antibodies having specificity for the antigen of interest may then be collected. The antibodies collected, isolated, and/or identified by performing the methods disclosed throughout advantageously reflect, collectively, one or more of the following attributes: broadening of epitopic coverage of the antigen of interest, normalization of epitopic coverage of the antigen of interest; reduction of selection bias towards (a) dominant epitope(s) on the antigen of interest; blocking of (a) dominant epitope(s) of the antigen of interest; identification of (a) rare or under-represented epitope(s) of the antigen of interest; and enrichment for antibodies with specificity toward (a) rare or under-represented epitope(s) of the antigen of interest; when interrogating antibody libraries for antibodies with specificity for an antigen of interest. Accordingly, the inventive reagents and methods disclosed throughout afford, inter alia, broadened epitopic coverage, normalized epitopic coverage, reduction is selection bias towards (a) dominant epitope(s), blocking (a) dominant epitope(s), identification (a) rare or under-represented epitope(s), and enrichment for antibodies with specificity toward (a) rare or under-represented epitope(s), when interrogating antibody libraries for antibodies with specificity for an antigen of interest.

Without wishing to be bound by any theory, it is believed that compositions comprising polyclonal antibody mixtures produced early in a selection process comprising the interrogation of a first library of antibodies against an antigen of interest, as disclosed throughout, serve effectively as competitors of dominant epitopes and/or of antibodies that are over-represented in antibody libraries from which the polyclonal mixtures are derived. Consequently, a re-interrogation of a second library of antibodies that comprises contacting the second library with a sample of a composition comprising the polyclonal mixture of antibodies collected from the interrogation of the first library in the selection process, affords the recovery of antibodies having specificity for rare(r) or under-represented epitopes, and thus also affords, inter alia, the following: broadening of epitopic coverage, normalizing of epitopic coverage, reduction of selection bias towards (a) dominant epitope(s), blocking (a) dominant epitope(s), identification (a) rare or under-represented epitope(s), and enrichment for antibodies with specificity toward (a) rare or under-represented epitope(s).

As will be understood by the artisan and as disclosed throughout, "epitopic coverage", "epitope coverage", and like terms refer to the extent to which antibodies are collected, isolated, and/or identified when performing a selection or library interrogation process that collectively have specificities for number of epitopes that approximate the full repertoire, or diversity, of available epitopes of the antigen of interest. Accordingly, when one or more of the methods disclosed throughout are performed, which methods comprise preparation and use of polyclonal mixtures of antibodies, the methods advantageously result in the collection, isolation, and/or identification of antibodies that collectively have specificities for a greater number of epitopes available on an antigen of interest relative to methods that to not comprise the preparation and use of polyclonal mixtures of antibodies.

As will be understood by the artisan and as disclosed throughout, "plurality" and "pluralities" refer to, in the broadest sense, two or more members of a group of items. In certain embodiments of the invention some or all of the members of such a plurality may be essentially identical. In certain other embodiments of the invention, many, most, or all of the members of a plurality of items, while each possessing similar characteristics that merit their inclusion in the plurality, are nonetheless different in some discernible way and possess different properties.

As will be appreciated by the artisan, the terms "plurality" and "library" (and "pluralities" and "libraries") may be readily used interchangeably. However, in the context of the inventions disclosed throughout, whereas a "plurality" of items, such as antibodies, nucleic acid encoding antibodies, or host cells, may comprise many or most members that are essentially identical, a "library" of items, such as antibodies, nucleic acid encoding antibodies, or host cells comprise members many or most members that are unique.

In the context of antibodies that are employed in practicing the disclosed inventions, a library (or plurality) of such antibodies will comprise many or most members that each possess a unique primary acid sequence; however, such libraries (or pluralities) may also include members that have identical amino acid sequences. In certain embodiments, the variable regions of such members will comprise many of the differences in amino acid sequence between such members.

In the context of host cells that are employed in practicing the disclosed inventions, a plurality (or library) of such host cells will comprise host cell members, many of which that each express a unique antibody; however, such host cell pluralities (or libraries) may also include members that express identical antibody sequences. In certain embodiments, such host cells will also harbor nucleic acid that collectively encodes the antibody libraries that are collectively expressed by the host cells.

As will be understood by the artisan and as disclosed throughout, "diversity" refers to a variety or a noticeable heterogeneity. The term "sequence diversity" refers to a variety of sequences which are collectively representative of several possibilities of sequences, for example, those found in natural human antibodies. For example, heavy chain CDR3 (CDRH3) sequence diversity may refer to a variety of possibilities of combining the known human DH and H3-JH segments, including the N1 and N2 regions, to form heavy chain CDR3 sequences. The light chain CDR3 (CDRL3) sequence diversity may refer to a variety of possibilities of combining the naturally occurring light chain variable region contributing to CDRL3 (i.e., L3-VL) and joining (i.e., L3-JL) segments, to form light chain CDR3 sequences. As used herein, H3-JH refers to the portion of the IGHJ gene contributing to CDRH3. As used herein, L3-VL and L3-JL refer to the portions of the IGLV and IGLJ genes (kappa or lambda) contributing to CDRL3, respectively.

As used herein, the term "expression" includes any step involved in the production of a polypeptide including, but not limited to, transcription, post-transcriptional modification, translation, post-translational modification, and secretion.

In certain embodiments of the invention, antibody libraries are designed to be small enough to chemically synthesize and physically realize, but large enough to encode antibodies with the potential to recognize any antigen. In certain embodiments, an antibody library comprises about $10^7$ to about $10^{20}$ different antibodies and/or polynucleotide sequences encoding the antibodies of the library. In some embodiments, the libraries are designed to include $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, or $10^{20}$ different antibodies and/or polynucleotide sequences encoding the antibodies. In certain embodiments, the libraries may comprise or encode about $10^3$ to about $10^5$, about $10^5$ to about $10^7$, about $10^7$ to about $10^9$, about $10^9$ to about $10^{11}$, about $10^{11}$ to about $10^{13}$, about $10^{13}$ to about $10^{15}$, about $10^{15}$ to about $10^{17}$, or about $10^{17}$ to about $10^{20}$ different antibodies. In certain embodiments, the diversity of the libraries may be characterized as being greater than or less than one or more of the diversities enumerated above, for example greater than about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, or $10^{20}$ or less than about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, or $10^{20}$. In certain other embodiments of the invention, the probability of an antibody of interest being present in a physical realization of a library with a size as enumerated above is at least about 0.0001%, 0.001%, 0.01%, 0.1%, 1%, 5%, 10%, 20%, 30%, 40%, 50%, 60%, 70%, 80%, 85%, 90%, 95%, 99%, 99.5%, or 99.9% (see Library Sampling, in the Detailed Description, for more information on the probability of a particular sequence being present in a physical realization of a library).

As will be understood by the artisan and as disclosed throughout, "broadening epitopic coverage", "broadened epitopic coverage", and like terms refer to increasing the number (or increased numbers) of epitopes available on an antigen of interest for which antibodies having specificity for such epitopes may be collected, isolated, and/or identified in a selection or library interrogation process that comprises the preparation and use of polyclonal antibody mixtures as disclosed throughout. Accordingly, when one or more of the methods disclosed throughout are performed, which methods comprise preparation and use of polyclonal mixtures of antibodies, the methods advantageously result in an increase the number of epitopes of an antigen of interest for which one or more antibodies are collected, isolated, and/or identified relative to the methods that do not comprise the preparation and use of polyclonal mixtures of antibodies.

As will be understood by the artisan and as disclosed throughout, "normalizing epitopic coverage", "normalized epitopic coverage", and like terms refer to decreasing the disparity (or decreased disparity) between the number of antibodies that are collected, isolated, and/or identified in a selection or library interrogation process having specificity for the least represented epitope(s) of an antigen of interest relative to the number of antibodies with specificity for the most represented epitope(s) of an antigen of interest. Accordingly, when one or more of the methods disclosed throughout are performed, which methods comprise preparation and use of polyclonal mixtures of antibodies, the methods advantageously result in a relative increase in the number of antibodies collected, isolated, and/or identified having specificity for the least represented epitope(s) of an antigen of interest and/or a decrease in the number of antibodies collected, isolated, and/or identified having specificity for the most represented epitope(s) of an antigen of interest, thereby normalizing epitopic coverage of the antigen of interest relative to methods that do not comprise the preparation and use of polyclonal mixtures of antibodies.

As will be understood by the artisan and as disclosed throughout, "under-represented epitope(s)", "less represented epitope(s)", "least represented epitope(s), "rare epitope(s)" and like terms refer to (an) epitope(s) of an antigen of interest for which a relatively low amount of antibodies are typically collected, isolated, and/or identified when performing a given selection or library interrogation process, relative to (an) epitope(s) of the antigen of interest for which a greater number antibodies may be collected, isolated, and/or identified when performing the given selection and/or interrogation process. Similarly, as will be understood by the artisan and as disclosed throughout, "over-represented epitope(s)", "more represented epitope(s)", "most represented epitope(s), "dominant epitope(s)", and like terms refer to (an) epitope(s) of an antigen of interest for which a relatively high amount of antibodies are typically collected, isolated, and/or identified when performing a given selection or library interrogation process, relative to (an) epitope(s) of the antigen of interest for which a fewer number antibodies may be collected, isolated, and/or identified when performing the given selection and/or interrogation process.

As will be understood by the artisan and as disclosed throughout, epitopes of an antigen of interest that are observed to be under-represented epitopes (and like terms) in certain selection or library interrogation processes are often less antigenic, often sterically hindered or obscured either by other portions of the antigen of interest or by antibodies that bind to over-represented epitopes, and/or represent epitopes for which the antibody-epitope interaction is relatively energetically unfavorable. When performing the methods disclosed throughout are performed, which methods comprise preparation and use of polyclonal mixtures of antibodies, the methods advantageously compete with, or "block" antibodies having specificity for over-represented, or dominant, epitopes of the antigen of interest, thereby facilitating the collection, isolation, and/or identification of a greater number of antibodies having specificity for under-represented, or rare, epitopes of the antigen of interest than would otherwise be achieved when performing methods that do not comprise the preparation and use of polyclonal mixtures of antibodies as disclosed throughout.

As will be understood by the artisan and as disclosed throughout, "specificity" refers to the property of an antibody which enables to react with one or more antigenic determinants, such as one or more epitopes, of an antigen of interest, and not with other epitopes of the antigen of interest or with other antigens of interest. As understood in the art, antibody specificity is dependent on chemical composition, physical forces, energetic favorability, steric hindrance, and molecular structure or topology of the binding site of the epitope and/or the antibody.

As will be understood by the artisan and as disclosed throughout, "affinity" refers to the strength, or stability of an antibody-epitope interaction. Antibodies with better affinity for an epitope bind relatively tightly and/or stably with the epitope, whereas antibodies with poorer affinity for an epitope bind relatively weakly and or less stably.

As will be understood by the artisan and as disclosed throughout, "collecting" or "collected" antibodies having specificity for (an) epitope(s) of an antigen of interest refers to distinguishing (or distinguished) antibodies that have such specificity from those antibodies that do not have such specificity. Collecting antibodies or collected antibodies having specificity for (an) epitope(s) of an antigen of interest need not require physical separation of antibodies from those antibodies that do not have such specificity in order for them to be distinguished. However, in certain embodiments, collecting antibodies having specificity for (an) epitope(s) of an antigen of interest comprises physically separating such antibodies from those antibodies that do not have such specificity. Exemplary methods and means for collecting antibodies are known in the art, and include, for example, flow cytometry, florescence activated cell sorting (FACS), magnetic activated cell sorting (MACS), enzyme-linked immunosorbent assay (ELISA), and the like, and combinations thereof.

Any means for determining such specificity in the art may be employed for determining such specificity in accordance with the methods disclosed throughout, and include, for example, labelling such antibodies with a detectable label; detecting a detectable label; detecting a functional consequence of antibody binding to (an) epitope of an antigen, such as competition with another antibody known to have specificity for such epitope(s); modulation of protein-protein or protein-ligand interaction between the antigen of interest and a known protein interaction partner or ligand.

Accordingly, in certain embodiments the invention provides a method of broadening epitopic coverage of an antigen of interest, the method comprising:
  a) contacting a first sample of the antigen of interest with a first library of antibodies;
  b) collecting antibodies that bind to the antigen from among the first sample employed in step a);
  c) preparing a composition comprising a polyclonal mixture of antibodies collected in step b);
  d) contacting a second sample of the antigen of interest with an aliquot of the composition prepared in step c) and a second library of antibodies; and
  e) after performing step d), collecting antibodies that bind to the second sample of the antigen from among the second library of antibodies employed in the contacting step d);
  wherein an increase in the number of different epitopes collectively recognized by the antibodies collected in step e) relative to the number of different epitopes collectively recognized by the antibodies contained in the composition prepared in step b) indicates that epitopic coverage of the antigen has been broadened.

In other embodiments, the invention provides a method of normalizing epitopic coverage of an antigen of interest, the method comprising:
  a) contacting a first sample of the antigen of interest with a first library of antibodies;
  b) collecting antibodies that bind to the antigen from among the first library of antibodies employed in step a);
  c) preparing a composition comprising a polyclonal mixture of antibodies collected in step b);
  d) contacting a second sample of the antigen of interest with an aliquot of the composition prepared in step c) and a second library of antibodies;
  e) after performing step d), collecting antibodies that bind to the second sample of the antigen from among the second library of antibodies employed in the contacting step d),
  wherein either:
    i) an increase in the number of different antibodies collected in step e) that bind to at least one under-represented epitope relative to the number of different antibodies contained in the composition prepared in step c) that bind the at least one under-represented epitope;
    ii) a decrease in the number of different antibodies collected in step e) that bind to at least one over-represented epitope relative to the number of different antibodies contained in the composition prepared in step c) that bind the at least one over-represented epitope; or
    iii) both i) and ii);
  indicates that the epitopic coverage of the antigen of interest has been normalized.

In other embodiments, the invention provides a method of reducing selection bias towards at least one dominant epitope of an antigen of interest, the method comprising:
  a) contacting a first sample of the antigen of interest with a first library of antibodies;
  b) collecting antibodies that bind to the antigen from among the first library of antibodies employed in step a);
  c) preparing a composition comprising a polyclonal mixture of antibodies collected in step b), wherein the composition comprises at least one antibody that recognizes at least one epitope of the antigen;
  d) contacting a second sample of the antigen of interest with an aliquot of the composition prepared in step c) and a second library of antibodies;
  wherein the at least one epitope is made less available for binding by antibodies contained in the second plurality of antibodies as a result of contacting the second sample of the antigen of interest with the composition prepared in step c), thereby reducing bias towards the at least one epitope on the antigen.

As will be understood by the artisan and as disclosed throughout, "selection bias" refers to a tendency for a relatively high proportion of unique antibodies obtained from a selection or library interrogation process to have specificity for one or a small number of the full repertoire of available epitopes of an antigen of interest. Antigens of interest which will likely give rise to increase selection bias comprise those antigens that comprise one or more dominant epitopes. Whereas it is understood that many, if not most, antigens of interest possess at least one dominant epitope and thus would likely give rise to selection bias for such dominant epitope(s) when performing selection or library interrogation process that do not comprise the preparation and use of polyclonal mixtures of antibodies as disclosed throughout, the methods of the invention, which do comprise the preparation and use of such polyclonal mixtures of antibodies advantageously reduce selection bias when performing selection or library interrogation processes in accordance with the methods disclosed throughout.

In certain embodiments, the invention provides a method of blocking at least one dominant epitope of an antigen of interest, the method comprising:
  a) contacting a first sample of the antigen of interest with a first library of antibodies;
  b) collecting antibodies that bind to the antigen from among the first library of antibodies employed in step a);
  c) preparing a composition comprising a polyclonal mixture of antibodies collected in in step b), wherein the composition comprises at least one antibody that recognizes at least one dominant epitope on the antigen;

d) contacting a second sample of the antigen of interest with an aliquot of the composition prepared in step c) and a second library of antibodies;

wherein the at least one dominant epitope is blocked by the at least one antibody in the mixture prepared in step c). In such embodiments, the polyclonal mixture of antibodies effectively competes with, or "blocks" one or more dominant epitopes of an antigen of interest when contacted therewith, such that antibodies comprising the second library of antibodies are less able, or essentially unable, to bind to such one or more dominant epitopes. As a result, antibodies having specificity for one or more rare epitopes are more readily collected, isolated, and/or identified.

Accordingly, in certain embodiments, the invention provides for a method of identifying at least one antibody with specificity for a rare epitope on an antigen of interest, the method comprising:

a) contacting a first sample of the antigen of interest with a first library of antibodies;

b) collecting antibodies that bind to the antigen from among the first library of antibodies employed in step a);

c) preparing a composition comprising a polyclonal mixture of antibodies collected in step b), wherein the composition comprises at least one antibody that recognizes at least one dominant epitope on the antigen;

d) contacting a second sample of the antigen of interest with an aliquot of the composition prepared in step c) and a second library of antibodies;

e) after performing step d), collecting at least antibody from the second library of antibodies that binds to the rare epitope. In certain embodiments, the at least one antibody that is identified in step e) constitutes an antibody that has specificity toward a rare epitope on the antigen of interest.

In certain other embodiments the invention provides for a method of enriching for antibodies having specificity towards at least one rare epitope of an antigen in an antibody selection process, the method comprising:

a) contacting a first sample of the antigen of interest with a first library of antibodies;

b) collecting antibodies that bind to the antigen from among the first library of antibodies employed in step a);

c) preparing a composition comprising a polyclonal mixture of antibodies collected in step b), wherein the composition comprises at least one antibody that recognizes at least one dominant epitope on the antigen;

d) contacting a second sample of the antigen of interest with an aliquot of the composition prepared in step c) and a second library of antibodies, thereby blocking the at least one dominant epitope;

e) after performing step d), collecting antibodies from among the second library of antibodies with specificity to the at least one rare epitope;

wherein the number of different antibodies having specificity to the at least one rare epitope collected in step e) is greater than the number of antibodies having specificity to the at least one rare epitope collected in step b).

As will be understood by the artisan and as disclosed throughout, "enriching for antibodies" refers to increasing the proportion of antibodies that are collected, isolated, and/or identified having specificity for at least one rare epitope of an antigen of interest relative to the total number of antibodies collected, isolated, and/or identified having specificity for all available epitopes of the antigen of interest. Accordingly, when performing a selection or library interrogation process according to the methods disclosed throughout, which comprise the preparation and use of a polyclonal mixture of antibodies as disclosed throughout, such methods provide for increased enrichment of antibodies having specificity toward one or more rare epitopes relative to selection or library interrogation process that do not comprise the preparation and use of a polyclonal mixture of antibodies as disclosed throughout.

In certain embodiments, antibodies which comprise the libraries of antibodies suitable for use in accordance with the methods disclosed throughout can comprise, for example full length immunoglobulins; full length IgGs; full length IgMs; full length IgEs; full length IgAs; variable domains, antibody fragments; linear antibodies, single chain antibodies; scFvs, Fv fragments; Fab fragments, Fab' fragments, (Fab')$_2$ fragments; multispecific antibodies; bispecific antibodies; trispecific antibodies; tetraspecific antibodies; humanized antibodies; and combinations thereof.

The term "antibody" is used herein in the broadest sense and specifically encompasses at least monoclonal antibodies, polyclonal antibodies, multi-specific antibodies (e.g., bispecific antibodies), chimeric antibodies, humanized antibodies, human antibodies, and antibody fragments. An antibody is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes.

An "antibody" also refers to an immunoglobulin molecule, a fragment of an immunoglobulin molecule, or a derivative thereof, which has the ability to specifically bind to an antigen, which may be, for example: a protein; a polypeptide; peptide; a hormone; a cytokine; a chemokine; a growth factor; a neurotransmitter; a carbohydrate-containing biological molecule; a lipid or fatty acid-containing biological molecule; or other biological molecule; via an epitope present on such antigen.

"Antibodies" as used herein and throughout also refer to polypeptides comprising one or more variable regions or variable domains of an antibody, wherein such variable regions(s) or variable domain(s) are capable of engaging and binding to one or more epitopes of one or more antigens.

Antibodies (used interchangeably with "immunoglobulins, or "immunoglobulin molecules") can be monomeric, dimeric, trimeric, tetrameric, pentameric, etc., and may comprise a class of structurally related proteins consisting of two pairs of polypeptide chains: one pair of light chains (LC) and one pair of heavy chains (HC), all of which are inter-connected by disulfide bonds. The structure of immunoglobulins has been well characterized. See for instance Fundamental Immunology Ch. 7 (Paul, W., ed., 2nd ed. Raven Press, N.Y. (1989)).

Traditional natural antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. IgA has several subclasses, including but not limited to IgA1 and IgA2. Thus, "isotype" as used herein is meant any of the classes and subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE. The distinguishing features between these antibody classes are their constant regions, although subtler differences may exist in the variable region.

Each of the light and heavy chains is made up of two distinct regions, referred to as the variable and constant regions. The IgG heavy chain is composed of four immunoglobulin domains linked from N- to C-terminus in the order VH-CH1-CH2-CH3, referring to the "variable heavy domain" (also referred to as a "heavy chain variable domain", used interchangeably throughout), heavy chain constant domain 1, heavy chain constant domain 2, and heavy chain constant domain 3 respectively (also referred to as VH-Cγ1-Cγ2-Cγ3, referring to the variable heavy domain, constant gamma 1 domain, constant gamma 2 domain, and constant gamma 3 domain respectively). The IgG light chain is composed of two immunoglobulin domains linked from N- to C-terminus in the order VL-CL, referring to the "variable light domain" (also referred to as a "light chain variable domain", used interchangeably throughout) and the light chain constant domain respectively. The constant regions show less sequence diversity, and are responsible for binding a number of natural proteins to elicit important biochemical events. The structure that constitutes the natural biological form of an antibody, including the variable and constant regions, is referred to herein as a "full length antibody". In most mammals, including humans and mice, the full length antibody of the IgG isotype is a tetramer and consists of two identical pairs of two immunoglobulin chains, each pair having one light chain and one heavy chain, each light chain comprising a VL and a CL, and each heavy chain comprising a VH, CH1, a CH2, and a CH3. In some mammals, for example in camels and llamas, IgG antibodies may consist of only two heavy chains, each heavy chain comprising a variable domain attached to the Fc region.

The heavy chain constant region typically is comprised of three domains, CH1, CH2, and CH3, and the CH1 and CH2 domains are connected by a hinge region. Each light chain typically is comprised of a light chain variable domain (abbreviated herein as "VL" or "VL") and a light chain constant domain. The VH and VL domains may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4. Typically, the numbering of amino acid residues in this region is performed by the method described in Kabat (see, e.g., Kabat et al, in "Sequences of Proteins of Immunological Interest," 5$^{th}$ Edition, U.S. Department of Health and Human Services, 1992). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of VH CDR2 and inserted residues (for instance residues 82a, 82b, and 82c, etc. according to Kabat) after heavy chain FR residue 82.

The Kabat numbering of residues may be determined for a given antibody by alignment at regions of homology of the sequence of the antibody with a "standard" Kabat numbered sequence.

The term "variable", "variable domain", or "variable region" each interchangeably refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable" regions or "complementarity determining regions" (CDRs). The more conserved (i.e., non-hypervariable) portions of the variable domains are called the "framework" regions (FRM). The variable domains of naturally occurring heavy and light chains each comprise four FRM regions, largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding site (see Kabat et al. Sequences of Proteins of Immunological Interest, 5th Ed. Public Health Service, National Institutes of Health, Bethesda, Md., 1991, incorporated by reference in its entirety). The constant domains are not directly involved in antigen binding, but exhibit various effector functions, such as, for example, antibody-dependent, cell-mediated cytotoxicity and complement activation.

The term "framework region" refers to the art-recognized portions of an antibody variable region that exist between the more divergent (i.e., hypervariable) CDRs. Such framework regions are typically referred to as frameworks 1 through 4 (FRM1, FRM2, FRM3, and FRM4) and provide a scaffold for the presentation of the six CDRs (three from the heavy chain and three from the light chain) in three dimensional space, to form an antigen-binding surface. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. MoI. Biol., 1987, 196: 901; Chothia et al, Nature, 1989, 342: 877; Martin and Thornton, J. MoI. Biol, 1996, 263: 800. Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

The term "canonical structure" may also include considerations as to the linear sequence of the antibody, for example, as catalogued by Kabat (Kabat et al, in "Sequences of Proteins of Immunological Interest," 5$^{th}$ Edition, U.S. Department of Health and Human Services, 1992). The Kabat numbering scheme is a widely adopted standard for numbering the amino acid residues of an antibody variable domain in a consistent manner. Additional structural considerations can also be used to determine the canonical structure of an antibody. For example, those differences not fully reflected by Kabat numbering can be described by the numbering system of Chothia et al and/or revealed by other techniques, for example, crystallography and two or three-dimensional computational modeling. Accordingly, a given antibody sequence may be placed into a canonical class which allows for, among other things, identifying appropriate chassis sequences (e.g., based on a desire to include a variety of canonical structures in a library). Kabat numbering of antibody amino acid sequences and structural considerations as described by Chothia et al., and their implications for construing canonical aspects of antibody structure, are described in the literature.

By "Fc" or "Fc region", as used herein is meant the polypeptide comprising the constant region of an antibody excluding the first constant region immunoglobulin domain. Thus "Fc region" refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Accordingly, and without departing from the above, "Fc region" may also be defined as comprising a "CH2 domain or a variant thereof" and a "CH3 domain or a variant thereof". Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, for example an antibody. By "Fc polypeptide" as used herein is meant a polypeptide that comprises all or part of an Fc region. Fc polypeptides include antibodies, Fc fusions, isolated Fcs, and Fc fragments.

A variable light chain (VL) and corresponding variable heavy domain (VH) of the inventive multivalent antibody analogs comprise a binding domain, also referred to interchangeably throughout as an "antigen binding site" that interacts with an antigen. Thus, a "first variable light domain" and a "first variable heavy domain" of the inventive multivalent antibody analogs together form a "first antigen binding site". Similarly, a "second variable light domain" and a "second variable heavy domain" of the inventive multivalent antibody analogs together form a "second antigen binding site". A "third variable light domain" and a "third variable heavy domain" of the inventive multivalent antibody analogs together form a "third antigen binding site", and so on.

The antigen binding sites for use in accordance with the invention, including the VHs, VLs, and/or CDRs that comprise such, may be obtained or derived from any source of such, as will be understood by the artisan. Accordingly, such antigen binding sites, VHs, VLs, and/or CDRs may be obtained or derived from hybridoma cells that express antibodies against a target recognized by such; from B cells from immunized donors, which express antibodies against a target recognized by such; from B-cells that have been stimulated to express antibodies against a target recognized by such; and or from identification of antibodies or antibody fragments that have been identified by screening a library comprising a plurality of polynucleotides or polypeptides for antigen binding antibodies (or antigen binding fragments thereof).

"Antibody fragments" comprise a portion of an intact antibody, for example, one or more portions of the antigen-binding region thereof. Examples of antibody fragments include Fab, Fab', F(ab')2, and Fv fragments, diabodies, linear antibodies, single-chain antibodies, and multi-specific antibodies formed from intact antibodies and antibody fragments.

"Humanized antibodies" generally refer to non-human antibodies that have had the variable-domain framework regions swapped for sequences found in human antibodies. Generally in a humanized antibody the entire antibody, except the CDRs, is encoded by a polynucleotide of human origin or is identical to such an antibody except within its CDRs. The CDRs, one, some, or all of which are encoded by nucleic acids originating in a non-human organism, are grafted into the framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239: 1534-1536. "Back mutation" of selected acceptor framework residues to the corresponding donor residues is often required to regain affinity that is lost in the initial grafted construct (see, e.g., U.S. Pat. No. 5,693,762). The humanized antibody optimally also will comprise at least a portion of an immunoglobulin constant region, typically that of a human immunoglobulin, and thus will typically comprise a human Fc region. A variety of techniques and methods for humanizing, reshaping, and resurfacing non-human antibodies are well known in the art (See Tsurushita & Vasquez, 2004, Humanization of Monoclonal Antibodies, Molecular Biology of B Cells, 533-545, Elsevier Science (USA), and references cited therein). In certain variations, the immunogenicity of the antibody is reduced using a method described in Lazar et al., 2007, Mol Immunol 44:1986-1998 and U.S. Ser. No. 11/004,590, entitled "Methods of Generating Variant Proteins with Increased Host String Content and Compositions Thereof", filed on Dec. 3, 2004.

An "intact antibody" is one comprising full-length heavy- and light-chains and an Fc region. An intact antibody is also referred to as a "full-length, heterodimeric" antibody or immunoglobulin.

The term "variable" refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable" regions or "complementarity determining regions" (CDRs). The more conserved (i.e., non-hypervariable) portions of the variable domains are called the "framework" regions (FRM). The variable domains of naturally occurring heavy and light chains each comprise four FRM regions, largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding site (see Kabat et al. Sequences of Proteins of Immunological Interest, 5th Ed. Public Health Service, National Institutes of Health, Bethesda, Md., 1991, incorporated by reference in its entirety). The constant domains are not directly involved in antigen binding, but exhibit various effector functions, such as, for example, antibody-dependent, cell-mediated cytotoxicity and complement activation.

The "chassis" of the invention represent a portion of the antibody heavy chain variable (IGHV) or light chain variable (IGLV) domains that are not part of CDRH3 or CDRL3, respectively. The chassis of the invention is defined as the portion of the variable region of an antibody beginning with the first amino acid of FRM1 and ending with the last amino acid of FRM3. In the case of the heavy chain, the chassis includes the amino acids including from about Kabat position 1 to about Kabat position 94. In the case of the light chains (kappa and lambda), the chassis are defined as including from about Kabat position 1 to about Kabat position 88. The chassis of the invention may contain certain modifications relative to the corresponding germline variable domain sequences presented herein or available in public databases. These modifications may be engineered (e.g., to remove N-linked glycosylation sites) or naturally occurring (e.g., to account for allelic variation). For example, it is known in the art that the immunoglobulin gene repertoire is polymorphic (Wang et al., Immunol. Cell. Biol, 2008, 86: 111; Collins et al, Immunogenetics, 2008, DOI 10.1007/s00251-008-0325-z, published online, each incorporated by reference in its entirety); chassis, CDRs (e.g., CDRH3) and constant regions representative of these allelic variants are also encompassed by the invention. In some embodiments, the allelic variant(s) used in a particular embodiment of the invention may be selected based on the allelic variation present in different patient populations, for example, to identify antibodies that are non-immunogenic in these patient populations. In certain embodiments, the immunogenicity of an antibody of the invention may depend on allelic variation in the major histocompatibility complex (MEW) genes of a patient population. Such allelic variation may also be considered in the design of libraries of the invention. In certain embodiments of the invention, the chassis and constant regions are contained on a vector, and a CDR3 region is introduced between them via homologous recombination. In some embodiments, one, two or three nucleotides may follow the heavy chain chassis, forming either a partial (if one or two) or a complete (if three) codon. When a full codon is present, these nucleotides encode an amino acid residue that is referred to as the "tail," and occupies position 95.

As will be understood by the artisan and as disclosed throughout antibody libraries suitable for use in accordance with the disclosed methods may be designed and prepared by any method available in the art as disclosed, for example, in WO2009036379; WO2012009568; WO2010105256; U.S. Pat. Nos. 8,258,082; 6,300,064; 6,696,248; 6,165,718; 6,500,644; 6,291,158; 6,291,159; 6,096,551; 6,368,805; 6,500,644; and the like.

For instance, libraries may be designed and prepared so as to reflect or mimic the pre-immune repertoire, and/or may be designed and prepared based on rational design informed by the collection of human V, D, and J genes, and other large databases of human heavy and light chain sequences (e.g., publicly known germline sequences; sequences from Jackson et al, J. Immunol Methods, 2007, 324: 26, incorporated by reference in its entirety; sequences from Lee et al., Immunogenetics, 2006, 57: 917, incorporated by reference in its entirety; and sequences compiled for rearranged VK and Vλ—see Appendices A and B filed herewith). Additional information may be found, for example, in Scaviner et al., Exp. Clin. Immunogenet., 1999, 16: 234; Tomlinson et al, J. Mol. Biol, 1992, 227: 799; and Matsuda et al, J. Exp. Med., 1998, 188: 2151 each incorporated by reference in its entirety. In certain embodiments of the invention, cassettes representing the possible V, D, and J diversity found in the human repertoire, as well as junctional diversity (i.e., N1 and N2), are synthesized de novo as single or double-stranded DNA oligonucleotides. In certain embodiments of the invention, oligonucleotide cassettes encoding CDR sequences are introduced into yeast along with one or more acceptor vectors containing heavy or light chain chassis sequences. No primer-based PCR amplification or template-directed cloning steps from mammalian cDNA or mRNA are employed. Through standard homologous recombination, the recipient yeast recombines the cassettes (e.g., CDR3s) with the acceptor vector(s) containing the chassis sequence (s) and constant regions, to create a properly ordered synthetic, full-length human heavy chain and/or light chain immunoglobulin library that can be genetically propagated, expressed, displayed, and screened. One of ordinary skill in the art will readily recognize that the chassis contained in the acceptor vector can be designed so as to produce constructs other than full-length human heavy chains and/or light chains. For example, in certain embodiments of the invention, the chassis may be designed to encode portions of a polypeptide encoding an antibody fragment or subunit of an antibody fragment, so that a sequence encoding an antibody fragment, or subunit thereof, is produced when the oligonucleotide cassette containing the CDR is recombined with the acceptor vector. In certain embodiments, the invention provides a synthetic, preimmune human antibody repertoire comprising about $10^1$ to about $10^{20}$ antibody members, wherein the repertoire comprises:

(a) selected human antibody heavy chain chassis (i.e., amino acids 1 to 94 of the heavy chain variable region, using Kabat's definition); (b) a CDRH3 repertoire, designed based on the human IGHD and IGHJ germline sequences, the CDRH3 repertoire comprising the following: (i) optionally, one or more tail regions;
(ii) one or more N1 regions, comprising about 0 to about 10 amino acids selected from the group consisting of fewer than 20 of the amino acid types preferentially encoded by the action of terminal deoxynucleotidyl transferase
(TdT) and functionally expressed by human B cells;
(iii) one or DH segments, based on one or more selected IGHD segments, and one or more N- or C-terminal truncations thereof;
(iv) one or more N2 regions, comprising about 0 to about 10 amino acids selected from the group consisting of fewer than 20 of the amino acids preferentially encoded by the activity of TdT and functionally expressed by human B cells; and
(v) one or more H3-JH segments, based on one or more IGHJ segments, and one or more N-terminal truncations thereof (e.g., down to XXWG); (c) one or more selected human antibody kappa and/or lambda light chain chassis; and
(d) a CDRL3 repertoire designed based on the human IGLV and IGLJ germline sequences, wherein "L" may be a kappa or lambda light chain.

The heavy chain chassis may be any sequence with homology to Kabat residues 1 to 94 of an immunoglobulin heavy chain variable domain. Non-limiting examples of heavy chain chassis are included in the Examples, and one of ordinary skill in the art will readily recognize that the principles presented therein, and throughout the specification, may be used to derive additional heavy chain chassis. As described above, the heavy chain chassis region is followed, optionally, by a "tail" region. The tail region comprises zero, one, or more amino acids that may or may not be selected on the basis of comparing naturally occurring heavy chain sequences. For example, in certain embodiments of the invention, heavy chain sequences available in the art may be compared, and the residues occurring most frequently in the tail position in the naturally occurring sequences included in the library (e.g., to produce sequences that most closely resemble human sequences). In other embodiments, amino acids that are used less frequently may be used. In still other embodiments, amino acids selected from any group of amino acids may be used. In certain embodiments of the invention, the length of the tail is zero (no residue) or one (e.g., G/D/E) amino acid. For the purposes of clarity, and without being bound by theory, in the naturally occurring human repertoire, the first ⅔ of the codon encoding the tail residue is provided by the FRM3 region of the VH gene. The amino acid at this position in naturally occurring heavy chain sequences may thus be considered to be partially encoded by the IGHV gene (⅔) and partially encoded by the CDRH3 (⅓). However, for the purposes of clearly illustrating certain aspects of the invention, the entire codon encoding the tail residue (and, therefore, the amino acid derived from it) is described herein as being part of the CDRH3 sequence.

As described above, there are two peptide segments derived from nucleotides which are added by TdT in the naturally occurring human antibody repertoire. These segments are designated N1 and N2 (referred to herein as N1 and N2 segments, domains, regions or sequences). In certain embodiments of the invention, N1 and N2 are about 0, 1, 2, or 3 amino acids in length. Without being bound by theory, it is thought that these lengths most closely mimic the N1 and N2 lengths found in the human repertoire. In other embodiments of the invention, N1 and N2 may be about 4, 5, 6, 7, 8, 9, or 10 amino acids in length. Similarly, the composition of the amino acid residues utilized to produce the N1 and N2 segments may also vary. In certain embodiments of the invention, the amino acids used to produce N1 and N2 segments may be selected from amongst the eight most frequently occurring amino acids in the N1 and N2 domains of the human repertoire (e.g., G, R, S, P, L, A, V, and T). In other embodiments of the invention, the amino acids used to produce the N1 and N2 segments may be selected from the group consisting of fewer than about 20, 19, 18, 17, 16, 15, 14, 13, 12, 11, 10, 9, 8, 7, 6, 5, 4, or 3 of the amino acids preferentially encoded by the activity of TdT and functionally expressed by human B cells. Alternatively, N1 and N2 may comprise amino acids selected from any group of amino acids. It is not required that N1 and N2 be of a similar length or composition, and independent variation of the length and composition of N1 and N2 is one method by which additional diversity may be introduced into the library.

The DH segments of the libraries are based on the peptides encoded by the naturally occurring IGHD gene repertoire, with progressive deletion of residues at the N- and C-termini. IGHD genes may be read in multiple reading frames, and peptides representing these reading frames, and their N- and C-terminal deletions are also included in the libraries of the invention. In certain embodiments of the invention, DH segments as short as three amino acid residues may be included in the libraries. In other embodiments of the invention, DH segments as short as about 1, 2, 4, 5, 6, 7, or 8 amino acids may be included in the libraries.

The H3-JH segments of the libraries are based on the peptides encoded by the naturally occurring IGHJ gene repertoire, with progressive deletion of residues at the N-terminus. The N-terminal portion of the IGHJ segment that makes up part of the CDRH3 is referred to herein as H3-JH. In certain embodiments of the invention, the H3-JH segment may be represented by progressive N-terminal deletions of one or more H3-JH residues, down to two H3-JH residues. In other embodiments of the invention, the H3-JH segments of the library may contain N-terminal deletions (or no deletions) down to about 6, 5, 4, 3, 2, 1, or 0 H3-JH residues.

The light chain chassis of the libraries may be any sequence with homology to Kabat residues 1 to 88 of naturally occurring light chain (κ or λ) sequences. In certain embodiments of the invention, the light chain chassis of the invention are synthesized in combinatorial fashion, utilizing VL and JL segments, to produce one or more libraries of light chain sequences with diversity in the chassis and CDR3 sequences. In other embodiments of the invention, the light chain CDR3 sequences are synthesized using degenerate oligonucleotides or trinucleotides and recombined with the light chain chassis and light chain constant region, to form full-length light chains. The instant invention also provides methods for producing and using such libraries, as well as libraries comprising one or more immunoglobulin domains or antibody fragments. Design and synthesis of each component of the claimed antibody libraries is provided in more detail below.

One step in building certain libraries of the invention is the selection of chassis sequences, which are based on naturally occurring variable domain sequences (e.g., IGHV and IGLV). This selection can be done arbitrarily, or by the selection of chassis that meet certain criteria. For example, the Kabat database, an electronic database containing non-redundant rearranged antibody sequences, can be queried for those heavy and light chain germline sequences that are most frequently represented. The BLAST search algorithm, or more specialized tools such as SoDA (Volpe et al., Bioinformatics, 2006, 22: 438-44, incorporated by reference in its entirety), can be used to compare rearranged antibody sequences with germline sequences, using the V BASE2 database (Retter et al, Nucleic Acids Res., 2005, 33: D671-D674), or similar collections of human V, D, and J genes, to identify the germline families that are most frequently used to generate functional antibodies. Several criteria can be utilized for the selection of chassis for inclusion in the libraries of the invention. For example, sequences that are known (or have been determined) to express poorly in yeast, or other organisms used in the invention (e.g., bacteria, mammalian cells, fungi, or plants) can be excluded from the libraries. Chassis may also be chosen based on their representation in the peripheral blood of humans. In certain embodiments of the invention, it may be desirable to select chassis that correspond to germline sequences that are highly represented in the peripheral blood of humans. In other embodiments, it may be desirable to select chassis that correspond to germline sequences that are less frequently represented, for example, to increase the canonical diversity of the library. Therefore, chassis may be selected to produce libraries that represent the largest and most structurally diverse group of functional human antibodies. In other embodiments of the invention, less diverse chassis may be utilized, for example, if it is desirable to produce a smaller, more focused library with less chassis variability and greater CDR variability. In some embodiments of the invention, chassis may be selected based on both their expression in a cell of the invention (e.g., a yeast cell) and the diversity of canonical structures represented by the selected sequences.

One may therefore produce a library with a diversity of canonical structures that express well in a cell of the invention.

In certain embodiments of the invention, the antibody library comprises variable heavy domains and variable light domains, or portions thereof. Each of these domains is built from certain components, which will be more fully described in the examples provided herein. In certain embodiments, the libraries described herein may be used to isolate fully human antibodies that can be used as diagnostics and/or therapeutics. Without being bound by theory, antibodies with sequences most similar or identical to those most frequently found in peripheral blood (for example, in humans) may be less likely to be immunogenic when administered as therapeutic agents. Without being bound by theory, and for the purposes of illustrating certain embodiments of the invention, the VH domains of the library may be considered to comprise three primary components: (1) a VH "chassis", which includes amino acids 1 to 94 (using Kabat numbering), (2) the CDRH3, which is defined herein to include the Kabat CDRH3 proper (positions 95-102), and (3) the FRM4 region, including amino acids 103 to 113 (Kabat numbering). The overall VH structure may therefore be depicted schematically (not to scale) as:

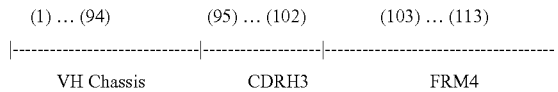

The selection and design of VH chassis sequences based on the human IGHV germline repertoire will become more apparent upon review of the examples provided herein. In certain embodiments of the invention, the VH chassis sequences selected for use in the library may correspond to all functionally expressed human IGHV germline sequences. Alternatively, IGHV germline sequences may be selected for representation in a library according to one or more criteria. For example, in certain embodiments of the invention, the selected IGHV germline sequences may be among those that are most highly represented among antibody molecules isolated from the peripheral blood of healthy adults, children, or fetuses.

In certain embodiments, it may be desirable to base the design of the VH chassis on the utilization of IGHV germline sequences in adults, children, or fetuses with a disease, for example, an autoimmune disease. Without being bound by theory, it is possible that analysis of germline sequence usage in the antibody molecules isolated from the peripheral blood of individuals with autoimmune disease may provide information useful for the design of antibodies recognizing human antigens. In some embodiments, the selection of IGHV germline sequences for representation in a library of the invention may be based on their frequency of occurrence in the peripheral blood. For the purposes of illustration, four IGHV1 germline sequences (IGHV1-2, IGHV1-18, IGHV1-46, and IGHV1-69) comprise about 80% of the IGHV1 family repertoire in peripheral blood. Thus, the specific IGHV1 germline sequences selected for representation in the library may include those that are most frequently occurring and that cumulatively comprise at least about 80% of the IGHV1 family repertoire found in peripheral blood. An analogous approach can be used to select specific IGHV germline sequences from any other IGHV family (i.e., IGHV1, IGHV2, IGHV3, IGHV4, IGHV5, IGHV6, and IGHV7). The specific germline sequences chosen for representation of a particular IGHV family in a library of the invention may therefore comprise at least about 100%, 99%, 98%, 97%, 96% 95%, 94%, 93%, 92%, 91% 90%, 89%, 88%, 87%, 86%, 85%, 84%, 83%, 82%, 81%, 80%, 75%, 70%, 65%, 60%, 55%, 50%, 45%, 40%, 35%, 30%, 25%, 20%, 15%, 10%, 5%, or 0% of the particular IGHV family member repertoire found in peripheral blood.

In some embodiments, the selected IGHV germline sequences may be chosen to maximize the structural diversity of the VH chassis library. Structural diversity may be evaluated by, for example, comparing the lengths, compositions, and canonical structures of CDRH1 and CDRH2 in the IGHV germline sequences. In human IGHV sequences, the CDRH1 (Kabat definition) may have a length of 5, 6 or 7 amino acids, while CDRH2 (Kabat definition) may have length of 16, 17, 18 or 19 amino acids. The amino acid compositions of the IGHV germline sequences and, in particular, the CDR domains, may be evaluated by sequence alignments, as presented in the Examples. Canonical structure may be assigned, for example, according to the methods described by Chothia et ah, J. Mol. Biol, 1992, 227: 799, incorporated by reference in its entirety. In certain embodiments of the invention, it may be advantageous to design VH chassis based on IGHV germline sequences that may maximize the probability of isolating an antibody with particular characteristics. For example, without being bound by theory, in some embodiments it may be advantageous to restrict the IGHV germline sequences to include only those germline sequences that are utilized in antibodies undergoing clinical development, or antibodies that have been approved as therapeutics. On the other hand, in some embodiments, it may be advantageous to produce libraries containing VH chassis that are not represented amongst clinically utilized antibodies. Such libraries may be capable of yielding antibodies with novel properties that are advantageous over those obtained with the use of "typical" IGHV germline sequences, or enabling studies of the structures and properties of "atypical" IGHV germline sequences or canonical structures.

One of ordinary skill in the art will readily recognize that a variety of other criteria can be used to select IGHV germline sequences for representation in a library of the invention. Any of the criteria described herein may also be combined with any other criteria. Further exemplary criteria include the ability to be expressed at sufficient levels in certain cell culture systems, solubility in particular antibody formats (e.g., whole immunoglobulins and antibody fragments), and the thermodynamic stability of the individual domains, whole immunoglobulins, or antibody fragments. The methods of the invention may be applied to select any IGHV germline sequence that has utility in an antibody library of the instant invention.

In certain embodiments of the invention, the VH chassis of the libraries may comprise from about Kabat residue 1 to about Kabat residue 94 of one or more of the following IGHV germline sequences: IGHV1-2, IGHV1-3, IGHV1-8, IGHV1-18, IGHV1-24, IGHV1-45, IGHV1-46, IGHV1-58, IGHV1-69, IGHV2-5, IGHV2-26, IGHV2-70, IGHV3-7, IGHV3-9, IGHV3-11, IGHV3-13, IGHV3-15, IGHV3-20, IGHV3-21, IGHV3-23, IGHV3-30, IGHV3-33, IGHV3-43, IGHV3-48, IGHV3-49, IGHV3-53, IGHV3-64, IGHV3-66, IGHV3-72, IGHV3-73, IGHV3-74, IGHV4-4, IGHV4-28, IGHV4-31, IGHV4-34, IGHV4-39, IGHV4-59, IGHV4-61, IGHV4-B, IGHV5-51, IGHV6-1, and IGHV7-4-1. In some embodiments of the invention, a library may contain one or more of these sequences, one or more allelic variants of these sequences, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65% 60%, 55%, or 50% identical to one or more of these sequences.

In other embodiments, the VH chassis of the libraries may comprise from about Kabat residue 1 to about Kabat residue 94 of the following IGHV germline sequences: IGHV1-2, IGHV1-18, IGHV1-46, IGHV1-69, IGHV3-7, IGHV3-15, IGHV3-23, IGHV3-30, IGHV3-33, IGHV3-48, IGHV4-31, IGHV4-34, IGHV4-39, IGHV4-59, IGHV4-61, IGHV4-B, and IGHV5-51. In some embodiments of the invention, a library may contain one or more of these sequences, one or more allelic variants of these sequences, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 55%, or 50% identical to one or more of these sequences.

While the selection of the VH chassis with sequences based on the IGHV germline sequences is expected to support a large diversity of CDRH3 sequences, further diversity in the VH chassis may be generated by altering the amino acid residues comprising the CDRH1 and/or CDRH2 regions of each chassis selected for inclusion in the library.

In certain embodiments of the invention, the alterations or mutations in the amino acid residues comprising the CDRH1 and CDRH2 regions, or other regions, of the IGHV germline sequences are made after analyzing the sequence identity within data sets of rearranged human heavy chain sequences that have been classified according to the identity of the original IGHV germline sequence from which the rearranged sequences are derived. For example, from a set of rearranged antibody sequences, the IGHV germline sequence of each antibody is determined, and the rearranged sequences are classified according to the IGHV germline sequence. This determination is made on the basis of sequence identity.

Next, the occurrence of any of the 20 amino acid residues at each position in these sequences is determined. In certain embodiments of the invention, one may be particularly interested in the occurrence of different amino acid residues at the positions within CDRH1 and CDRH2, for example if increasing the diversity of the antigen-binding portion of the VH chassis is desired. In other embodiments of the invention, it may be desirable to evaluate the occurrence of different amino acid residues in the framework regions. Without being bound by theory, alterations in the framework regions may impact antigen binding by altering the spatial orientation of the CDRs. After the occurrence of amino acids at each position of interest has been identified, alterations may be made in the VH chassis sequence, according to certain criteria. In some embodiments, the objective may be to produce additional VH chassis with sequence variability that mimics the variability observed in the heavy chain domains of rearranged human antibody sequences (derived from respective IGHV germline sequences) as closely as possible, thereby potentially obtaining sequences that are most human in nature (i.e., sequences that most closely mimic the composition and length of human sequences). In this case, one may synthesize additional VH chassis sequences that include mutations naturally found at a particular position and include one or more of these VH chassis sequences in a library of the invention, for example at a frequency that mimics the frequency found in nature. In another embodiment of the invention, one may wish to include VH chassis that represent only mutations that most frequently occur at a given position in rearranged human antibody sequences. For example, rather than mimicking the human variability precisely, as described above, one may choose to include only top 19, 18, 17, 16, 15, 14, 13, 12, 11, 10, 9, 8, 7, 6, 5, 4, 3, 2, or 1, amino acid residues that most frequently occur at each position. For the purposes of illustration, if one wished to include the top four most frequently occurring amino acid residues at position 31 of the VH 1-69 sequence, then position 31 in the VH 1-69 sequence would be varied to include S, N, T, and R. Without being bound by theory, it is thought that the introduction of diversity by mimicking the naturally occurring composition of the rearranged heavy chain sequences is likely to produce antibodies that are most human in composition. However, the libraries of the invention are not limited to heavy chain sequences that are diversified by this method, and any criteria can be used to introduce diversity into the heavy chain chassis, including random or rational mutagenesis. For example, in certain embodiments of the invention, it may be preferable to substitute neutral and/or smaller amino acid residues for those residues that occur in the IGHV germline sequence. Without being bound by theory, neutral and/or smaller amino acid residues may provide a more flexible and less sterically hindered context for the display of a diversity of CDR sequences.

One of ordinary skill in the art will readily recognize that this method can be applied to any germline sequence, and can be used to generate at least about 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 1000, $10^4$, $10^5$, $10^6$, or more variants of each heavy chain chassis.

The light chain chassis of the invention may be based on kappa and/or lambda light chain sequences. The principles underlying the selection of light chain variable (IGLV) germline sequences for representation in the library are analogous to those employed for the selection of the heavy chain. Similarly, the methods used to introduce variability into the selected heavy chain chassis may also be used to introduce variability into the light chain chassis.

Without being bound by theory, and for the purposes of illustrating certain embodiments of the invention, the VL domains of the library may be considered to comprise three primary components: (1) a VL "chassis", which includes amino acids 1 to 88 (using Kabat numbering), (2) the VLCDR3, which is defined herein to include the Kabat CDRL3 proper (positions 89-97), and (3) the FRM4 region, including amino acids 98 to 107 (Kabat numbering). The overall VL structure may therefore be depicted schematically (not to scale) as:

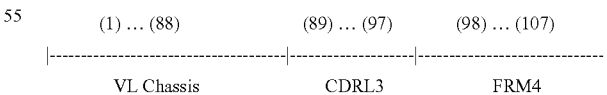

In certain embodiments of the invention, the VL chassis of the libraries include one or more chassis based on IGKV germline sequences. In certain embodiments of the invention, the VL chassis of the libraries may comprise from about Kabat residue 1 to about Kabat residue 88 of one or more of the following IGKV germline sequences: IGKV1-05, IGKV1-06, IGKV1-08, IGKV1-09, IGKV1-12, IGKV1-13, IGKV1-16, IGKV1-17, IGKV1-27, IGKV1-33, IGKV1-

37, IGKV1-39, IGKV1D-16, IGKV1D-17, IGKV1D-43, IGKV1D-8, IGKV2-24, IGKV2-28, IGKV2-29, IGKV2-30, IGKV2-40, IGKV2D-26, IGKV2D-29, IGKV2D-30, IGKV3-11, IGKV3-15, IGKV3-20, IGKV3D-07, IGKV3D-11, IGKV3D-20, IGKV4-1, IGKV5-2, IGKV6-21, and IGKV6D-41. In some embodiments of the invention, a library may contain one or more of these sequences, one or more allelic variants of these sequences, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 55%, or 50% identical to one or more of these sequences.

In other embodiments, the VL chassis of the libraries may comprise from about Kabat residue 1 to about Kabat residue 88 of the following IGKV germline sequences: IGKV1-05, IGKV1-12, IGKV1-27, IGKV1-33, IGKV1-39, IGKV2-28, IGKV3-11, IGKV3-15, IGKV3-20, and IGKV4-1. In some embodiments of the invention, a library may contain one or more of these sequences, one or more allelic variants of these sequences, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 55%, or 50% identical to one or more of these sequences.

In certain embodiments of the invention, the VL chassis of the libraries include one or more chassis based on IGλV germline sequences. In certain embodiments of the invention, the VL chassis of the libraries may comprise from about Kabat residue 1 to about Kabat residue 88 of one or more of the following IGλV germline sequences: IGλV3-1, IGλV3-21, IGλV2-14, IGW1-40, IGW3-19, IGW1-51, IGW1-44, IGW6-57, IGW2-8, IGW3-25, IGλV2-23, IGW3-10, IGW4-69, IGW1-47, IGλV2-11, IGW7-43, IGW7-46, IGW5-45, IGW4-60, IGW10-54, IGW8-61, IGW3-9, IGW1-36, 18, IGW3-16, IGW3-27, IGW5-39, IGW9-49, and IGW3-12. In some embodiments of the invention, a library may contain one or more of these sequences, one or more allelic variants of these sequences, or encode an amino acid sequence at least about 99.9%, 99.5%, 99%, 98%, 97%, 96%, 95%, 94%, 93%, 92%, 91%, 90%, 85%, 80%, 75%, 70%, 65%, 60%, 55%, or 50% identical to one or more of these sequences.

In other embodiments, the VL chassis of the libraries may comprise from about Kabat residue 1 to about Kabat residue 88 of the following IGλV germline sequences: IGλV3-1, IGW3-21, IGλV2-14, IGW1-40, IGW3-19, IGW1-51, IGλV1-44, IGW6-57, IGW4-69, IGW7-43, and IGW5-45. In some embodiments of the invention, a library may contain one or more of these sequences, one or more allelic variants of these sequences, or encode an amino acid sequence at least about 99.9%, 99.5%, 99%, 98%, 97%, 96%, 95%, 94%, 93%, 92%, 91%, 90%, 85%, 80%, 75%, 70%, 65%, 60%, 55%, or 50% identical to one or more of these sequences.

It is known in the art that diversity in the CDR3 region of the heavy chain is sufficient for most antibody specificities (Xu and Davis, Immunity, 2000, 13: 27-45, incorporated by reference in its entirety) and that existing successful libraries have been created using CDRH3 as the major source of diversification (Hoogenboom et ah, J. Mol. Biol, 1992, 227: 381; Lee et ah, J. Mol. Biol, 2004, 340: 1073 each of which is incorporated by reference in its entirety). It is also known that both the DH region and the N1/N2 regions contribute to the CDRH3 functional diversity (Schroeder et ah, J. Immunol, 2005, 174: 7773 and Mathis et ah, Eur J Immunol, 1995, 25: 3115, each of which is incorporated by reference in its entirety). For the purposes of the present invention, the CDHR3 region of naturally occurring human antibodies can be divided into five segments: (1) the tail segment, (2) the N1 segment, (3) the DH segment, (4) the N2 segment, and (5) the JH segment. As exemplified below, the tail, N1 and N2 segments may or may not be present. In certain embodiments of the invention, the method for selecting amino acid sequences for the synthetic CDRH3 libraries includes a frequency analysis and the generation of the corresponding variability profiles of existing rearranged antibody sequences. In this process, which is described in more detail in the Examples section, the frequency of occurrence of a particular amino acid residue at a particular position within rearranged CDRH3s (or any other heavy or light chain region) is determined.

Amino acids that are used more frequently in nature may then be chosen for inclusion in a library of the invention.

In certain embodiments of the invention, the libraries contain CDRH3 regions comprising one or more segments designed based on the IGHD gene germline repertoire. In some embodiments of the invention, DH segments selected for inclusion in the library are selected and designed based on the most frequent usage of human IGHD genes, and progressive N-terminal and C-terminal deletions thereof, to mimic the in vivo processing of the IGHD gene segments. In some embodiments of the invention, the DH segments of the library are about 3 to about 10 amino acids in length. In some embodiments of the invention, the DH segments of the library are about 0, 1, 2, 3, 4, 5, 6, 7, 8, 9, or 10 amino acids in length, or a combination thereof. In certain embodiments, the libraries of the invention may contain DH segments with a wide distribution of lengths (e.g., about 0 to about 10 amino acids). In other embodiments, the length distribution of the DH may be restricted (e.g., about 1 to about 5 amino acids, about 3 amino acids, about 3 and about 5 amino acids, and so on). In certain embodiments of the library, the shortest DH segments may be about 0, 1, 2, 3, 4, 5, 6, 7, 8, 9, or 10 amino acids.

In certain embodiments of the invention, libraries may contain DH segments representative of any reading frame of any IGHD germline sequence. In certain embodiments of the invention, the DH segments selected for inclusion in a library include one or more of the following IGHD sequences, or their derivatives (i.e., any reading frame and any degree of N-terminal and C-terminal truncation): IGHD3-10, IGHD3-22, IGHD6-19, IGHD6-13, IGHD3-3, IGHD2-2, IGHD4-17, IGHD1-26, IGHD5-5/5-18, IGHD2-15, IGHD6-6, IGHD3-9, IGHD5-12, IGHD5-24, IGHD2-21, IGHD3-16, IGHD4-23, IGHD1-I, IGHD1-7, IGHD4-4/4-11, IGHD1-20, IGHD7-27, IGHD2-8, and IGHD6-25. In some embodiments of the invention, a library may contain one or more of these sequences, allelic variants thereof, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 55%, or 50% identical to one or more of these sequences.

N-terminal and C-terminal deletions of other IGHD sequences and reading frames are also encompassed by the invention, and one of ordinary skill in the art can readily determine these sequences using, for example, the methods outlined above In certain embodiments of the invention, the DH segments selected for inclusion in a library include one or more of the following IGHD sequences, or their derivatives (i.e., any reading frame and any degree N-terminal and C-terminal truncation): IGHD3-10, IGHD3-22, IGHD6-19, IGHD6-13, IGHD3-03, IGHD2-02, IGHD4-17, IGHD1-26, IGHD5-5/5-18, and IGHD2-15. In some embodiments of the invention, a library may contain one or more of these sequences, allelic variants thereof, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 55%, or 50% identical to one or more of these sequences.

In certain embodiments of the invention, the DH segments selected for inclusion in a library include one or more of the following IGHD sequences, wherein the notation "_x" denotes the reading frame of the gene, or their derivatives (i.e., any degree of N-terminal or C-terminal truncation): IGHD1-26_1, IGHD1-26_3, IGHD2-2_2, IGHD2-2_3, IGHD2-15_2, IGHD3-3_3, IGHD3-10_1, IGHD3-10_2, IGHD3-10_3, IGHD3-22_2, IGHD4-17_2, IGHD5-5_3, IGHD6-13_1, IGHD6-13_2, IGHD6-19_1, and IGHD6-19_2. In some embodiments of the invention, a library may contain one or more of these sequences, allelic variants thereof, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 55%, or 50% identical to one or more of these sequences.

In certain embodiments of the invention, the libraries are designed to reflect a pre-determined length distribution of N- and C-terminal deleted IGHD segments. For example, in certain embodiments of the library, the DH segments of the library may be designed to mimic the natural length distribution of DH segments found in the human repertoire. For example, the relative occurrence of different IGHD segments in rearranged human antibody heavy chain domains from Lee et al. (Immunogenetics, 2006, 57: 917, incorporated by reference in its entirety).

In certain embodiments, the relative occurrence of IGHD Gene Usage as taught by Lee et al., for example, may be used to design a library with DH prevalence that is similar to the IGHD usage found in peripheral blood. In other embodiments of the invention, it may be preferable to bias the library toward longer or shorter DH segments, or DH segments of a particular composition. In other embodiments, it may be desirable to use all DH segments selected for the library in equal proportion. In certain embodiments of the invention, the most commonly used reading-frames of the ten most frequently occurring IGHD sequences are utilized, and progressive N-terminal and C-terminal deletions of these sequences are made, thus providing a total of 278 non-redundant DH segments that are used to create a CDRH3 repertoire. In some embodiments of the invention, the methods described above can be applied to produce libraries comprising the top 1, 2, 3, 4, 5, 6, 7, 8, 9, 10, 11, 12, 13, 14, 15, 16, 17, 18, 19, 20, 21, 22, 23, 24, or 25 expressed IGHD sequences, and progressive N-terminal and C-terminal deletions thereof. As with all other components of the library, while the DH segments may be selected from among those that are commonly expressed, it is also within the scope of the invention to select these gene segments based on the fact that they are less commonly expressed. This may be advantageous, for example, in obtaining antibodies toward self-antigens or in further expanding the diversity of the library. Alternatively, DH segments can be used to add compositional diversity in a manner that is strictly relative to their occurrence in actual human heavy chain sequences.

In certain embodiments of the invention, the progressive deletion of IGHD genes containing disulfide loop encoding segments may be limited, so as to leave the loop intact and to avoid the presence of unpaired cysteine residues. In other embodiments of the invention, the presence of the loop can be ignored and the progressive deletion of the IGHD gene segments can occur as for any other segments, regardless of the presence of unpaired cysteine residues. In still other embodiments of the invention, the cysteine residues can be mutated to any other amino acid.

There are six IGHJ (Joining) segments, IGHJ1, IGHJ2, IGHJ3, IGHJ4, IGHJ5, and IGHJ6. Similar to the N- and C-terminal deletions that the IGHD genes undergo, natural variation is introduced into the IGHJ genes by N-terminal "nibbling", or progressive deletion, of one or more codons by exonuclease activity.

The H3-JH segment refers to the portion of the IGHJ segment that is part of CDRH3. In certain embodiments of the invention, the H3-JH segment of a library comprises one or more of the following sequences: AEYFQH (SEQ ID NO:), EYFQH (SEQ ID NO:), YFQH (SEQ ID NO:), FQH (SEQ ID NO:), QH (SEQ ID NO:), H (SEQ ID NO:), YWYFDL (SEQ ID NO:), WYFDL (SEQ ID NO:), YFDL (SEQ ID NO:), FDL (SEQ ID NO:), DL (SEQ ID NO:), L (SEQ ID NO:), AFDV (SEQ ID NO:), FDV (SEQ ID NO:), DV (SEQ ID NO:), V (SEQ ID NO:), YFDY (SEQ ID NO:), FDY (SEQ ID NO:), DY (SEQ ID NO:), Y (SEQ ID NO:), NWFDS (SEQ ID NO:), WFDS (SEQ ID NO:), FDS (SEQ ID NO:), DS (SEQ ID NO:), S (SEQ ID NO:), YYYYYGMDV (SEQ ID NO:), YYYYGMDV (SEQ ID NO:), YYYGMDV (SEQ ID NO:), YYGMDV (SEQ ID NO:), YGMDV (SEQ ID NO:), GMDV (SEQ ID NO:), MDV (SEQ ID NO:), and DV (SEQ ID NO:). In some embodiments of the invention, a library may contain one or more of these sequences, allelic variations thereof, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 60%, 55%, or 50% identical to one or more of these sequences.

In other embodiments of the invention, the H3-JH segment may comprise about 0, 1, 2, 3, 4, 5, 6, 7, 8, 9, or more amino acids. For example, the H3-JH segment of JH 1 4 has a length of three residues, while non-deleted JH6 has an H3-JH segment length of nine residues. The FRM4-JH region of the IGHJ segment begins with the sequence WG(Q/R)G (SEQ ID NO:) and corresponds to the portion of the IGHJ segment that makes up part of framework 4. In certain embodiments of the invention, there are 28 H3-JH segments that are included in a library. In certain other embodiments, libraries may be produced by utilizing about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the IGHJ segments enumerated above.

Design and selection of the N1 and N2 segment repertoires may be performed by employing the use of Terminal deoxynucleotidyl transferase (TdT). Terminal deoxynucleotidyl transferase (TdT) is a highly conserved enzyme from vertebrates that catalyzes the attachment of 5' triphosphates to the 3' hydroxyl group of single- or double-stranded DNA. Hence, the enzyme acts as a template-independent polymerase (Koiwai et ah, Nucleic Acids Res., 1986, 14: 5777; Basu et al., Biochem. Biophys. Res. Comm., 1983, 111: 1105, each incorporated by reference in its entirety). In vivo, TdT is responsible for the addition of nucleotides to the V-D and D-J junctions of antibody heavy chains (Alt and Baltimore, PNAS, 1982, 79: 4118; Collins et al, J. Immunol., 2004, 172: 340, each incorporated by reference in its entirety). Specifically, TdT is responsible for creating the N1 and N2 (non-templated) segments that flank the D (diversity) region.

In certain embodiments of the invention, the length and composition of the N1 and N2 segments are designed rationally, according to statistical biases in amino acid usage found in naturally occurring N1 and N2 segments in human antibodies. One embodiment of a library produced via this method is described in Example 5. According to data compiled from human databases (Jackson et al, J. Immunol Methods, 2007, 324: 26, incorporated by reference in its entirety), there are an average of 3.02 amino acid insertions for N1 and 2.4 amino acid insertions for N2, not taking into account insertions of two nucleotides or less. In certain embodiments of the invention, N1 and N2 segments are restricted to lengths of zero to three amino acids. In other embodiments of the invention, N1 and N2 may be restricted to lengths of less than about 4, 5, 6, 7, 8, 9, or 10 amino acids.

In some embodiments of the invention, the composition of these sequences may be chosen according to the frequency of occurrence of particular amino acids in the N1 and N2 sequences of natural human antibodies. In certain embodiments of the invention, the eight most commonly occurring amino acids in these regions (i.e., G, R, S, P, L, A, T, and V) are used to design the synthetic N1 and N2 segments. In other embodiments of the invention about the most 1, 2, 3, 4, 5, 6, 7, 8, 9, 10, 11, 12, 13, 14, 15, 16, 17, 18, or 19 most commonly occurring amino acids may be used in the design of the synthetic N1 and N2 segments. In still other embodiments, all 20 amino acids may be used in these segments. Finally, while it is possible to base the designed composition of the N1 and N2 segments of the invention on the composition of naturally occurring N1 and N2 segments, this is not a requirement. The N1 and N2 segments may comprise amino acids selected from any group of amino acids, or designed according to other criteria considered for the design of a library of the invention. A person of ordinary skill in the art would readily recognize that the criteria used to design any portion of a library of the invention may vary depending on the application of the particular library. It is an object of the invention that it may be possible to produce a functional library through the use of N1 and N2 segments selected from any group of amino acids, no N1 or N2 segments, or the use of N1 and N2 segments with compositions other than those described herein.

One important difference between the libraries of the current invention and other libraries known in the art is the consideration of the composition of naturally occurring duplet and triplet amino acid sequences during the design of the library. Many of these can be represented by the general formula (G/P)(G/R/S/P/L/A/V/T) (SEQ ID NO:) or (R/S/L/A/V/T)(G/P) (SEQ ID NO:). In certain embodiments of the invention, the synthetic N1 and N2 regions may comprise all of these duplets. In other embodiments, the library may comprise the top 2, 3, 4, 5, 6, 7, 8, 9, 10, 11, 12, 13, 14, 15, 16, 17, 18, 19, 20, 21, 22, 23, 24, or 25 most common naturally occurring N1 and/or N2 duplets. In other embodiments of the invention, the libraries may include duplets that are less frequently occurring (i.e., outside of the top 25). The composition of these additional duplets or triplets could readily be determined, given the methods taught herein.

Finally, the data from the naturally occurring triplet N1 and N2 regions demonstrates that the naturally occurring N1 and N2 triplet sequences can often be represented by the formulas (G)(G)(G/R/S/P/L/A/V/T) (SEQ ID NO:), (G)(R/S/P/L/A/V/T)(G) (SEQ ID NO:), or (R/S/P/L/A/V/T)(G)(G) (SEQ ID NO:). In certain embodiments of the invention, the library may comprise the top 2, 3, 4, 5, 6, 7, 8, 9, 10, 11, 12, 13, 14, 15, 16, 17, 18, 19, 20, 21, 22, 23, 24, or 25 most commonly occurring N1 and/or N2 triplets. In other embodiments of the invention, the libraries may include triplets that are less frequently occurring (i.e., outside of the top 25). The composition of these additional duplets or triplets could readily be determined, given the methods taught herein.

In certain embodiments of the invention, there are about 59 total N1 segments and about 59 total N2 segments used to create a library of CDRH3s. In other embodiments of the invention, the number of N1 segments, N2 segments, or both is increased to about 141. In other embodiments of the invention, one may select a total of about 0, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 1000, $10^4$, or more N1 and/or N2 segments for inclusion in a library of the invention.

One of ordinary skill in the art will readily recognize that, given the teachings of the instant specification, it is well within the realm of normal experimentation to extend the analysis detailed herein, for example, to generate additional rankings of naturally occurring duplet and triplet (or higher order) N regions that extend beyond those presented herein (e.g., using sequence alignment, the SoDA algorithm, and any database of human sequences (Volpe et al, Bioinformatics, 2006, 22: 438-44, incorporated by reference in its entirety). An ordinarily skilled artisan would also recognize that, based on the information taught herein, it is now possible to produce libraries that are more diverse or less diverse (i.e., more focused) by varying the number of distinct amino acid sequences used in the N1 pool and/or N2 pool.

As described above, many alternative embodiments are envisioned, in which the compositions and lengths of the N1 and N2 segments vary from those presented in the Examples herein. In some embodiments, sub-stoichiometric synthesis of trinucleotides may be used for the synthesis of N1 and N2 segments. Sub-stoichiometric synthesis with trinucleotides is described in Knappik et al (U.S. Pat. No. 6,300,064, incorporated by reference in its entirety). The use of sub-stoichiometric synthesis would enable synthesis with consideration of the length variation in the N1 and N2 sequences. In addition to the embodiments described above, a model of the activity of TdT may also be used to determine the composition of the N1 and N2 sequences in a library of the invention. For example, it has been proposed that the probability of incorporating a particular nucleotide base (A, C, G, T) on a polynucleotide, by the activity of TdT, is dependent on the type of base and the base that occurs on the strand directly preceding the base to be added. Jackson et al, (J. Immunol. Methods, 2007, 324: 26, incorporated by reference in its entirety) have constructed a Markov model describing this process. In certain embodiments of the invention, this model may be used to determine the composition of the N1 and/or N2 segments used in libraries of the invention. Alternatively, the parameters presented in Jackson et al could be further refined to produce sequences that more closely mimic human sequences.

Design of a CDRH3 Library Using the N1, DH, N2, and H3-JH Segments

The CDRH3 libraries of the invention comprise an initial amino acid (in certain exemplary embodiments, G, D, E) or lack thereof (designated herein as position 95), followed by the N1, DH, N2, and H3-JH segments. Thus, in certain embodiments of the invention, the overall design of the CDRH3 libraries can be represented by the following formula:

[G/D/E/-]-[N1]-[DH]-[N2]-[H3-JH]. While the compositions of each portion of a CDRH3 of a library of the invention are more fully described above, the composition of the tail presented above (G/D/E/-) is non-limiting, and that any amino acid (or no amino acid) can be used in this position. Thus, certain embodiments of the invention may be represented by the following formula:

[X]-[N1]-[DH]-[N2]-[H3-JH], wherein [X] is any amino acid residue or no residue.

In certain embodiments of the invention, a synthetic CDRH3 repertoire is combined with selected VH chassis sequences and heavy chain constant regions, via homologous recombination. Therefore, in certain embodiments of the invention, it may be necessary to include DNA sequences flanking the 5' and 3' ends of the synthetic CDRH3 libraries, to facilitate homologous recombination between the synthetic CDRH3 libraries and vectors containing the selected chassis and constant regions. In certain embodiments, the vectors also contain a sequence encoding at least a portion of the non-nibbled region of the IGHJ gene (i.e., FRM4-JH). Thus, a polynucleotide encoding an N-terminal sequence (e.g., CA(K/R/T)) may be added to the synthetic CDRH3 sequences, wherein the N-terminal polynucleotide is homologous with FRM3 of the chassis, while a polynucleotide encoding a C-terminal sequence (e.g., WG(Q/R)G) may be added to the synthetic CDRH3, wherein the C-terminal polynucleotide is homologous with FRM4-JH. Although the sequence WG(Q/R)G is presented in this exemplary embodiment, additional amino acids, C-terminal to this sequence in FRM4-JH may also be included in the polynucleotide encoding the C-terminal sequence. The purpose of the polynucleotides encoding the N-terminal and C-terminal sequences, in this case, is to facilitate homologous recombination, and one of ordinary skill in the art would recognize that these sequences may be longer or shorter than depicted below.

Accordingly, in certain embodiments of the invention, the overall design of the CDRH3 repertoire, including the sequences required to facilitate homologous recombination with the selected chassis, can be represented by the following formula (regions homologous with vector underlined):
CA[R/K/T]-[X]-[N1]-[DH]-[N2]-[H3-JH]-[WG(Q/R)G].

In other embodiments of the invention, the CDRH3 repertoire can be represented by the following formula, which excludes the T residue presented in the schematic above: CA[R/K]-[X]-[1]-[DH]-[N2]-[H3-H]-[WG(Q/R)G].

References describing collections of V, D, and J genes include Scaviner et al., Exp. Clin, Immunogenet., 1999, 16: 243 and Ruiz et ah, Exp. Clin. Immunogenet, 1999, 16: 173, each incorporated by reference in its entirety.

CDRH3 Length Distributions

As described throughout this application, in addition to accounting for the composition of naturally occurring CDRH3 segments, the instant invention also takes into account the length distribution of naturally occurring CDRH3 segments. Surveys by Zemlin et al. (JMB, 2003, 334: 733, incorporated by reference in its entirety) and Lee et al. (Immunogenetics, 2006, 57: 917, incorporated by reference in its entirety) provide analyses of the naturally occurring CDRH3 lengths. These data show that about 95% of naturally occurring CDRH3 sequences have a length from about 7 to about 23 amino acids. In certain embodiments, the instant invention provides rationally designed antibody libraries with CDRH3 segments which directly mimic the size distribution of naturally occurring CDRH3 sequences. In certain embodiments of the invention, the length of the CDRH3s may be about 2 to about 30, about 3 to about 35, about 7 to about 23, about 3 to about 28, about 5 to about 28, about 5 to about 26, about 5 to about 24, about 7 to about 24, about 7 to about 22, about 8 to about 19, about 9 to about 22, about 9 to about 20, about 10 to about 18, about 11 to about 20, about 11 to about 18, about 13 to about 18, or about 13 to about 16 residues in length.

In certain embodiments of the invention, the length distribution of a CDRH3 library of the invention may be defined based on the percentage of sequences within a certain length range. For example, in certain embodiments of the invention, CDRFBs with a length of about 10 to about 18 amino acid residues comprise about 84% to about 94% of the sequences of a the library. In some embodiments, sequences within this length range comprise about 89% of the sequences of a library.

In other embodiments of the invention, CDRFBs with a length of about 11 to about 17 amino acid residues comprise about 74% to about 84% of the sequences of a library. In some embodiments, sequences within this length range comprise about 79% of the sequences of a library.

In still other embodiments of the invention, CDRFBs with a length of about 12 to about 16 residues comprise about 57% to about 67% of the sequences of a library. In some embodiments, sequences within this length range comprise about 62% of the sequences of a library.

In certain embodiments of the invention, CDRH3s with a length of about 13 to about 15 residues comprise about 35% to about 45% of the sequences of a library. In some embodiments, sequences within this length range comprise about 40% of the sequences of a library.

Design of the Antibody Library CDRL3 Components

The CDRL3 libraries of the invention can be generated by one of several approaches. The actual version of the CDRL3 library made and used in a particular embodiment of the invention will depend on objectives for the use of the library. More than one CDRL3 library may be used in a particular embodiment; for example, a library containing CDRH3 diversity, with kappa and lambda light chains is within the scope of the invention. In certain embodiments of the invention, a CDRL3 library is a VKCDR3 (kappa) library and/or a VλCDR3 (lambda) library. The CDRL3 libraries described herein differ significantly from CDRL3 libraries in the art. First, they consider length variation that is consistent with what is observed in actual human sequences. Second, they take into consideration the fact that a significant portion of the CDRL3 is encoded by the IGLV gene. Third, the patterns of amino acid variation within the IGLV gene-encoded CDRL3 portions are not stochastic and are selected based on depending on the identity of the IGLV gene. Taken together, the second and third distinctions mean that CDRL3 libraries that faithfully mimic observed patterns in human sequences cannot use a generic design that is independent of the chassis sequences in FRM1 to FRM3. Fourth, the contribution of JL to CDRL3 is also considered explicitly, and enumeration of each amino acid residue at the relevant positions is based on the compositions and natural variations of the JL genes themselves.

As indicated above, and throughout the application, a unique aspect of the design of the libraries of the invention is the germline or "chassis-based" aspect, which is meant to preserve more of the integrity and variability of actual human sequences. This is in contrast to other codon-based synthesis or degenerate oligonucleotide synthesis approaches that have been described in the literature and that aim to produce "one-size-fits-all" (e.g., consensus) libraries (e.g., Knappik, et al, J Mol Biol, 2000, 296: 57; Akamatsu et ah, J Immunol, 1993, 151: 4651, each incorporated by reference in its entirety).

In certain embodiments of the invention, patterns of occurrence of particular amino acids at defined positions within VL sequences are determined by analyzing data available in public or other databases, for example, the NCBI database (see, for example, GI numbers in Appendices A and B filed herewith). In certain embodiments of the invention, these sequences are compared on the basis of identity and assigned to families on the basis of the germline genes from which they are derived. The amino acid composition at each position of the sequence, in each germline family, may then be determined. This process is illustrated in the Examples provided herein.

Minimalist VKCDR3 Libraries

In certain embodiments of the invention, the light chain CDR3 library is a VKCDR3 library. Certain embodiments of the invention may use only the most common VKCDR3 length, nine residues; this length occurs in a dominant proportion (greater than about 70%) of human VKCDR3 sequences. In human VKCDR3 sequences of length nine, positions 89-95 are encoded by the IGKV gene and positions 96-97 are encoded by the IGKJ gene. Analysis of human kappa light chain sequences indicates that there are not strong biases in the usage of the IGKJ genes. Therefore, in certain embodiments of the invention, each of the five the IGKJ genes can be represented in equal proportions to create a combinatorial library of (M VK chassis)×(5 JK genes), or a library of size M×5. However, in other embodiments of the invention, it may be desirable to bias IGKJ gene representation, for example to restrict the size of the library or to weight the library toward IGKJ genes known to have particular properties. As described in Example 6.1, examination of the first amino acid encoded by the IGKJ gene (position 96) indicated that the seven most common residues found at this position are L, Y, R, W, F, P, and I. These residues cumulatively account for about 85% of the residues found in position 96 in naturally occurring kappa light chain sequences. In certain embodiments of the invention, the amino acid residue at position 96 may be one of these seven residues. In other embodiments of the invention, the amino acid at this position may be chosen from amongst any of the other 13 amino acid residues. In still other embodiments of the invention, the amino acid residue at position 96 may be chosen from amongst the top 1, 2, 3, 4, 5, 6, 7, 8, 9, 10, 11, 12, 13, 14, 15, 16, 17, 18, 19, or 20 amino acids that occur at position 96, or even residues that never occur at position 96. Similarly, the occurrence of the amino acids selected to occupy position 96 may be equivalent or weighted. In certain embodiments of the invention, it may be desirable to include each of the amino acids selected for inclusion in position 96 at equivalent amounts. In other embodiments of the invention, it may be desirable to bias the composition of position 96 to include particular residues more or less frequently than others. For example, as presented in Example 6.1, arginine occurs at position 96 most frequently when the IGKJ1 germline sequence is used. Therefore, in certain embodiments of the invention, it may be desirable to bias amino acid usage at position 96 according to the origin of the IGKJ germline sequence(s) and/or the IGKV germline sequence(s) selected for representation in a library.

Therefore, in certain embodiments of the invention, a minimalist VKCDR3 library may be represented by one or more of the following amino acid sequences:

[VK Chassis]-[L3-VK]-[F/L/I/R/W/Y/P]-[JK*]
[VK Chassis]-[L3-VK]-[X]-[JK*]

In these schematic exemplary sequences, VK Chassis represents any VK chassis selected for inclusion in a library of the invention. Specifically, VK Chassis comprises about Kabat residues 1 to 88 of a selected IGKV sequence. L3-VK represents the portion of the VKCDR3 encoded by the chosen IGKV gene (in this embodiment, Kabat residues 89-95). F, L, I, R, W, Y, and P are the seven most commonly occurring amino acids at position 96 of VKCDR3s with length nine, X is any amino acid, and JK* is an IGKJ amino acid sequence without the N-terminal residue (i.e., the N-terminal residue is substituted with F, L, I, R, W, Y, P, or X). Thus, in one possible embodiment of the minimalist VKCDR3 library, 70 members could be produced by utilizing 10 VK chassis, each paired with its respective L3-VK, 7 amino acids at position 96 (i.e., X), and one JK* sequence. Another embodiment of the library may have 350 members, produced by combining 10 VK chassis, each paired with its respective L3-VK, with 7 amino acids at position 96, and all 5 JK* genes. Still another embodiment of the library may have 1,125 members, produced by combining 15 VK chassis, each paired with its respective H3-JK, with 15 amino acids at position 96 and all 5 JK* genes, and so on. A person of ordinary skill in the art will readily recognize that many other combinations are possible. Moreover, while it is believed that maintaining the pairing between the VK chassis and the L3-VK results in libraries that are more similar to human kappa light chain sequences in composition, the L3-VK regions may also be combinatorially varied with different VK chassis regions, to create additional diversity.

VKCDR3 Libraries of about $10^5$ Complexity

While the dominant length of VKCDR3 sequences in humans is about nine amino acids, other lengths appear at measurable frequencies that cumulatively approach almost about 30% of VKCDR3 sequences. In particular, VKCDR3 of lengths 8 and 10 represent about 8.5% and about 16%, respectively, of VKCDR3 lengths in representative samples. Thus, more complex VKCDR3 libraries may include CDR lengths of 8, 10, and 11 amino acids. Such libraries could account for a greater percentage of the length distribution observed in collections of human VKCDR3 sequences, or even introduce VKCDR3 lengths that do not occur frequently in human VKCDR3 sequences (e.g., less than eight residues or greater than 11 residues).

The inclusion of a diversity of kappa light chain length variations in a library of the invention also enables one to include sequence variability that occurs outside of the amino acid at the VK-JK junction (i.e., position 96, described above). In certain embodiments of the invention, the patterns of sequence variation within the VK, and/or JK segments can be determined by aligning collections of sequences derived from particular germline sequences. In certain embodiments of the invention, the frequency of occurrence of amino acid residues within VKCDR3 can be determined by sequence alignments. In some embodiments of the invention, this frequency of occurrence may be used to introduce variability into the VK Chassis, L3-VK and/or JK segments that are used to synthesize the VKCDR3 libraries. In certain embodiments of the invention, the top 1, 2, 3, 4, 5, 6, 7, 8, 9, 10, 11, 12, 13, 14, 15, 16, 17, 18, 19, or 20 amino acids that occur at any particular position in a naturally occurring repertoire may be included at that position in a VKCDR3 library of the invention. In certain embodiments of the invention, the percent occurrence of any amino acid at any particular position within the VKCDR3 or a VK light chain may be about 0%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100%. In certain embodiments of the invention, the percent occurrence of any amino acid at any position within a VKCDR3 or kappa light chain library of the invention may be within at least about 1%, 2%, 3%, 4%, 5%, 6%, 7%, 8%, 9% 10%, 15%, 20%, 30%, 40%, 50%, 60%, 70%, 80%, 90%, 100%, 120%, 140%, 160%, 180%, or 200% of the percent occurrence of any amino acid at any position within a naturally occurring VKCDR3 or kappa light chain domain.

In some embodiments of the invention, a VKCDR3 library may be synthesized using degenerate oligonucleotides. In some embodiments of the invention, the limits of oligonucleotide synthesis and the genetic code may require the inclusion of more or fewer amino acids at a particular position in the VKCDR3 sequences.

More Complex VKCDR3 Libraries

The limitations inherent in using the genetic code and degenerate oligonucleotide synthesis may, in some cases, require the inclusion of more or fewer amino acids at a particular position within VKCDR3, in comparison to those amino acids found at that position in nature. This limitation can be overcome through the use of a codon-based synthesis approach (Virnekas et al. Nucleic Acids Res., 1994, 22: 5600, incorporated by reference in its entirety), which enables precise synthesis of oligonucleotides encoding particular amino acids and a finer degree of control over the proportion of any particular amino acid incorporated at any position.

In some embodiments of the invention, a codon-based synthesis approach may be used to vary the percent occurrence of any amino acid at any particular position within the VKCDR3 or kappa light chain. In certain embodiments, the percent occurrence of any amino acid at any position in a VKCDR3 or kappa light chain sequence of the library may be about 0%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100%. In some embodiments of the invention, the percent occurrence of any amino acid at any position may be about 1%, 2%, 3%, or 4%. In certain embodiments of the invention, the percent occurrence of any amino acid at any position within a VKCDR3 or kappa light chain library of the invention may be within at least about 1%, 2%, 3%, 4%, 5%, 6%, 7%, 8%, 9%, 10%, 15%, 20%, 30%, 40%, 50%, 60%, 70%, 80%, 90%, 100%, 120%, 140%, 160%, 180%, or 200% of the percent occurrence of any amino acid at any position within a naturally occurring VKCDR3 or kappa light chain domain.

In certain embodiments of the invention, the VKCDR3 (and any other sequence used in the library, regardless of whether or not it is part of VKCDR3) may be altered to remove undesirable amino acid motifs. For example, peptide sequences with the pattern N-X-(S or T)-Z, where X and Z are different from P, will undergo post-translational modification (N-linked glycosylation) in a number of expression systems, including yeast and mammalian cells. In certain embodiments of the invention, the introduction of N residues at certain positions may be avoided, so as to avoid the introduction of N-linked glycosylation sites. In some embodiments of the invention, these modifications may not be necessary, depending on the organism used to express the library and the culture conditions. However, even in the event that the organism used to express libraries with potential N-linked glycosylation sites is incapable of N-linked glycosylation (e.g., bacteria), it may still be desirable to avoid N-X-(SAT) sequences, as the antibodies isolated from such libraries may be expressed in different systems (e.g., yeast, mammalian cells) later (e.g., toward clinical development), and the presence of carbohydrate moieties in the variable domains, and the CDRs in particular, may lead to unwanted modifications of activity.

In certain embodiments of the invention, it may be preferable to create the individual sub-libraries of different lengths (e.g., one or more of lengths 5, 6, 7, 8, 9, 10, 11, or more) separately, and then mix the sub-libraries in proportions that reflect the length distribution of VKCDR3 in human sequences; for example, in ratios approximating the 1:9:2 distribution that occurs in natural VKCDR3 sequences of lengths 8, 9, and 10. In other embodiments, it may be desirable to mix these sub-libraries at ratios that are different from the distribution of lengths in natural VKCDR3 sequences, for example, to produce more focused libraries or libraries with particular properties.

VλCDR3 Libraries

The principles used to design the minimalist VλCDR3 libraries of the invention are similar to those enumerated above, for the VKCDR3 libraries, and are explained in more detail in the Examples. One difference between the VλCDR3 libraries of the invention and the VKCDR3 libraries of the invention is that, unlike the IGKV genes, the contribution of the IGVλ genes to CDRL3 (i.e., L3-Vλ) is not constrained to a fixed number of amino acid residues. Therefore, while the combination of the VK (including L3-VK) and JK segments, with inclusion of position 96, yields CDRL3 with a length of only 9 residues, length variation may be obtained within a VλCDR3 library even when only the Vλ (including L3-Vλ) and Jλ segments are considered. As for the VKCDR3 sequences, additional variability may be introduced into the VλCDR3 sequences via the same methods outlined above, namely determining the frequency of occurrence of particular residues within VλCDR3 sequences and synthesizing the oligonucleotides encoding the desired compositions via degenerate oligonucleotide synthesis or trinucleotides-based synthesis.

Synthetic Antibody Libraries

In certain embodiments of the invention, both the heavy and light chain chassis sequences and the heavy and light chain CDR3 sequences are synthetic. The polynucleotide sequences of the instant invention can be synthesized by various methods. For example, sequences can be synthesized by split pool DNA synthesis as described in Feldhaus et al., Nucleic Acids Research, 2000, 28: 534; Omstein et ah, Biopolymers, 1978, 17: 2341; and Brenner and Lerner, PNAS, 1992, 87: 6378 (each of which is incorporated by reference in its entirety).

In some embodiments of the invention, cassettes representing the possible V, D, and J diversity found in the human repertoire, as well as junctional diversity, are synthesized de novo either as double-stranded DNA oligonucleotides, single-stranded DNA oligonucleotides representative of the coding strand, or single-stranded DNA oligonucleotides representative of the non-coding strand. These sequences can then be introduced into a host cell along with an acceptor vector containing a chassis sequence and, in some cases a portion of FRM4 and a constant region. No primer-based PCR amplification from mammalian cDNA or mRNA or template-directed cloning steps from mammalian cDNA or mRNA need be employed.

Construction of Libraries by Yeast Homologous Recombination

In certain embodiments, the present invention exploits the inherent ability of yeast cells to facilitate homologous recombination at high efficiency. The mechanism of homologous recombination in yeast and its applications are briefly described below. As an illustrative embodiment, homologous recombination can be carried out in, for example, *Saccharomyces cerevisiae*, which has genetic machinery designed to carry out homologous recombination with high efficiency. Exemplary *S. cerevisiae* strains include EM93, CEN.PK2, RM11-1a, YJM789, and BJ5465. This mechanism is believed to have evolved for the purpose of chromosomal repair, and is also called "gap repair" or "gap filling". By exploiting this mechanism, mutations can be introduced into specific loci of the yeast genome. For example, a vector carrying a mutant gene can contain two sequence segments that are homologous to the 5' and 3' open reading frame (ORF) sequences of a gene that is intended to be interrupted or mutated. The vector may also encode a positive selection marker, such as a nutritional enzyme allele (e.g., URA3) and/or an antibiotic resistant marker (e.g., Geneticin/G418), flanked by the two homologous DNA segments. Other selection markers and antibiotic resistance markers are known to one of ordinary skill in the art. In some embodiments of the invention, this vector (e.g., a plasmid) is linearized and transformed into the yeast cells. Through homologous recombination between the plasmid and the yeast genome, at the two homologous recombination sites, a reciprocal exchange of the DNA content occurs between the wild type gene in the yeast genome and the mutant gene (including the selection marker gene(s)) that is flanked by the two homologous sequence segments. By selecting for the one or more selection markers, the surviving yeast cells will be those cells in which the wild-type gene has been replaced by the mutant gene (Pearson et al., Yeast, 1998, 14: 391, incorporated by reference in its entirety). This mechanism has been used to make systematic mutations in all 6,000 yeast genes, or open reading frames (ORFs) for functional genomics studies. Because the exchange is reciprocal, a similar approach has also been used successfully to clone yeast genomic DNA fragments into a plasmid vector (Iwasaki et al, Gene, 1991, 109: 81, incorporated by reference in its entirety).

By utilizing the endogenous homologous recombination machinery present in yeast, gene fragments or synthetic oligonucleotides can also be cloned into a plasmid vector without a ligation step. In this application of homologous recombination, a target gene fragment (i.e., the fragment to be inserted into a plasmid vector, e.g., a CDR3) is obtained (e.g., by oligonucleotides synthesis, PCR amplification, restriction digestion out of another vector, etc.). DNA sequences that are homologous to selected regions of the plasmid vector are added to the 5' and 3' ends of the target gene fragment. These homologous regions may be fully synthetic, or added via PCR amplification of a target gene fragment with primers that incorporate the homologous sequences. The plasmid vector may include a positive selection marker, such as a nutritional enzyme allele (e.g., URA3), or an antibiotic resistance marker (e.g., Geneticin/G418). The plasmid vector is then linearized by a unique restriction cut located in-between the regions of sequence homology shared with the target gene fragment, thereby creating an artificial gap at the cleavage site. The linearized plasmid vector and the target gene fragment flanked by sequences homologous to the plasmid vector are co-transformed into a yeast host strain. The yeast is then able to recognize the two stretches of sequence homology between the vector and target gene fragment and facilitate a reciprocal exchange of DNA content through homologous recombination at the gap. As a consequence, the target gene fragment is inserted into the vector without ligation.

The method described above has also been demonstrated to work when the target gene fragments are in the form of single stranded DNA, for example, as a circular M 13 phage derived form, or as single stranded oligonucleotides (Simon and Moore, MoI. Cell Biol, 1987, 7: 2329; Ivanov et al, Genetics, 1996, 142: 693; and DeMarini et al, 2001, 30: 520, each incorporated by reference in its entirety). Thus, the form of the target that can be recombined into the gapped vector can be double stranded or single stranded, and derived from chemical synthesis, PCR, restriction digestion, or other methods.

Several factors may influence the efficiency of homologous recombination in yeast. For example, the efficiency of the gap repair is correlated with the length of the homologous sequences flanking both the linearized vector and the target gene. In certain embodiments, about 20 or more base pairs may be used for the length of the homologous sequence, and about 80 base pairs may give a near-optimized result (Hua et al, Plasmid, 1997, 38: 91; Raymond et al, Genome Res., 2002, 12: 190, each incorporated by reference in its entirety). In certain embodiments of the invention, at least about 5, 10, 15, 20, 21, 22, 23, 24, 25, 26, 27, 28, 29, 30, 31, 32, 33, 34 35, 36, 37, 38, 39, 40, 45, 50, 55, 60, 65, 70, 75, 80, 85, 90, 95, 100, 110, 120, 130, 140, 150, 160, 170, 180, 187, 190, or 200 homologous base pairs may be used to facilitate recombination. In other embodiments, between about 20 and about 40 base pairs are utilized. In addition, the reciprocal exchange between the vector and gene fragment is strictly sequence-dependent, i.e. it does not cause a frame shift. Therefore, gap-repair cloning assures the insertion of gene fragments with both high efficiency and precision. The high efficiency makes it possible to clone two, three, or more targeted gene fragments simultaneously into the same vector in one transformation attempt (Raymond et al, Biotechniques, 1999, 26: 134, incorporated by reference in its entirety). Moreover, the nature of precision sequence conservation through homologous recombination makes it possible to clone selected genes or gene fragments into expression or fusion vectors for direct functional examination (El-Deiry et al, Nature Genetics, 1992, 1: 4549; Ishioka et al., PNAS, 1997, 94: 2449, each incorporated by reference in its entirety).

Libraries of gene fragments have also been constructed in yeast using homologous recombination. For example, a human brain cDNA library was constructed as a two-hybrid fusion library in vector pJG4-5 (Guidotti and Zervos, Yeast, 1999, 15: 715, incorporated by reference in its entirety). It has also been reported that a total of 6,000 pairs of PCR primers were used for amplification of 6,000 known yeast ORFs for a study of yeast genomic protein interactions (Hudson et al., Genome Res., 1997, 7: 1169, incorporated by reference in its entirety). In 2000, Uetz et al. conducted a comprehensive analysis of protein-protein interactions in *Saccharomyces cerevisiae* (Uetz et al, Nature, 2000, 403: 623, incorporated by reference in its entirety). The protein-protein interaction map of the budding yeast was studied by using a comprehensive system to examine two-hybrid interactions in all possible combinations between the yeast proteins (Ito et al, PNAS, 2000, 97: 1143, incorporated by reference in its entirety), and the genomic protein linkage map of Vaccinia virus was studied using this system (McCraith et al, PNAS, 2000, 97: 4879, incorporated by reference in its entirety).

In certain embodiments of the invention, a synthetic CDR3 (heavy or light chain) may be joined by homologous recombination with a vector encoding a heavy or light chain chassis, a portion of FRM4, and a constant region, to form a full-length heavy or light chain. In certain embodiments of the invention, the homologous recombination is performed directly in yeast cells. In some embodiments, the method comprises: (a) transforming into yeast cells: (i) a linearized vector encoding a heavy or light chain chassis, a portion of FRM4, and a constant region, wherein the site of linearization is between the end of FRM3 of the chassis and the beginning of the constant region; and (ii) a library of CDR3 insert nucleotide sequences that are linear and double stranded, wherein each of the CDR3 insert sequences comprises a nucleotide sequence encoding CDR3 and 5'- and 3'-flanking sequences that are sufficiently homologous to the termini of the vector of (i) at the site of linearization to enable homologous recombination to occur between the vector and the library of CDR3 insert sequences; and (b) allowing homologous recombination to occur between the vector and the CDR3 insert sequences in the transformed yeast cells, such that the CDR3 insert sequences are incorporated into the vector, to produce a vector encoding full-length heavy chain or light chain. As specified above, the CDR3 inserts may have a 5' flanking sequence and a 3' flanking sequence that are homologous to the termini of the linearized vector. When the CDR3 inserts and the linearized vectors are introduced into a host cell, for example, a yeast cell, the "gap" (the linearization site) created by linearization of the vector is filled by the CDR3 fragment insert through recombination of the homologous sequences at the 5' and 3' termini of these two linear double-stranded DNAs (i.e., the vector and the insert). Through this event of homologous recombination, libraries of circular vectors encoding full-length heavy or light chains comprising variable CDR3 inserts is generated. Particular instances of these methods are presented in the Examples.

Subsequent analysis may be carried out to determine the efficiency of homologous recombination that results in correct insertion of the CDR3 sequences into the vectors. For example, PCR amplification of the CDR3 inserts directly from selected yeast clones may reveal how many clones are recombinant. In certain embodiments, libraries with minimum of about 90% recombinant clones are utilized. In certain other embodiments libraries with a minimum of about 1%, 5% 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% recombinant clones are utilized. The same PCR amplification of selected clones may also reveal the insert size. To verify the sequence diversity of the inserts in the selected clones, a PCR amplification product with the correct size of insert may be "fingerprinted" with restriction enzymes known to cut or not cut within the amplified region. From a gel electrophoresis pattern, it may be determined whether the clones analyzed are of the same identity or of the distinct or diversified identity. The PCR products may also be sequenced directly to reveal the identity of inserts and the fidelity of the cloning procedure, and to prove the independence and diversity of the clones.

In certain embodiments, the methods disclosed throughout may comprise the use of pluralities of host cells, members of which collectively harbor nucleic acids that collectively encode the libraries of antibodies, wherein such host cells collectively express the libraries of antibodies that are interrogated for binders to the antigen of interest. When such pluralities of host cells are prepared and employed in accordance with the methods disclosed throughout, either: those host cells that express antibodies with specificity toward an antigen of interest are be collected from amongst the plurality of host cells host cells that are interrogated; or the antibodies that are encoded by such host cells may be collected. In certain embodiments, the antibodies are collected after the host cells express and secrete them.

In accordance with the use of host cells in the methods disclosed throughout libraries of polynucleotides generated by any of the techniques described herein, or other suitable techniques, may be introduced into such host cells and thereby expressed and screened to identify antibodies having desired structure and/or activity. Expression of the antibodies can be carried out, for example, using cell-free extracts (and e.g., ribosome display), phage display, prokaryotic host cells (e.g., bacterial display), or eukaryotic host cells (e.g., yeast display, mammalian cell display). In certain embodiments of the invention, the antibody libraries are expressed and/or encoded by yeast. In certain embodiments, the yeast are *Saccharomyces cerevesaie*. In other embodiments, the yeast are *Pichia pastoris*.

In other embodiments, the polynucleotides are engineered to serve as templates that can be expressed in a cell-free extract. Vectors and extracts as described, for example in U.S. Pat. Nos. 5,324,637; 5,492,817; 5,665,563, (each incorporated by reference in its entirety) can be used and many are commercially available. Ribosome display and other cell-free techniques for linking a polynucleotide (i.e., a genotype) to a polypeptide (i.e., a phenotype) can be used, e.g., Profusion™ (see, e.g., U.S. Pat. Nos. 6,348,315; 6,261, 804; 6,258,558; and 6,214,553, each incorporated by reference in its entirety).

Alternatively, the polynucleotides of the invention can be expressed in an *E. coli* expression system, such as that described by Pluckthun and Skerra. (Meth. Enzymol., 1989, 178: 476; Biotechnology, 1991, 9: 273, each incorporated by reference in its entirety). The mutant proteins can be expressed for secretion in the medium and/or in the cytoplasm of the bacteria, as described by Better and Horwitz, Meth. Enzymol., 1989, 178: 476, incorporated by reference in its entirety. In some embodiments, the single domains encoding VH and VL are each attached to the 3' end of a sequence encoding a signal sequence, such as the ompA, phoA or pelB signal sequence (Lei et al, J. BacterioL, 1987, 169: 4379, incorporated by reference in its entirety). These gene fusions are assembled in a dicistronic construct, so that they can be expressed from a single vector, and secreted into the periplasmic space of *E. coli* where they will refold and can be recovered in active form. (Skerra et al, Biotechnology, 1991, 9: 273, incorporated by reference in its entirety). For example, antibody heavy chain genes can be concurrently expressed with antibody light chain genes to produce antibodies or antibody fragments.

In other embodiments of the invention, the antibody sequences are expressed on the membrane surface of a prokaryote, e.g., *E. coli*, using a secretion signal and lipidation moiety as described, e.g., in US20040072740; US20030100023; and US20030036092 (each incorporated by reference in its entirety).

Higher eukaryotic cells, such as mammalian cells, for example myeloma cells (e.g., NS/0 cells), hybridoma cells, Chinese hamster ovary (CHO), and human embryonic kidney (HEK) cells, can also be used for expression of the antibodies of the invention. Typically, antibodies expressed in mammalian cells are designed to be secreted into the culture medium, or expressed on the surface of the cell. The antibody or antibody fragments can be produced, for example, as intact antibody molecules or as individual VH and VL fragments, Fab fragments, single domains, or as single chains (scFv) (Huston et al, PNAS, 1988, 85: 5879, incorporated by reference in its entirety).

Alternatively, antibodies can be expressed and screened by anchored periplasmic expression (APEx 2-hybrid surface display), as described, for example, in Jeong et al, PNAS, 2007, 104: 8247 (incorporated by reference in its entirety) or by other anchoring methods as described, for example, in Mazor et al., Nature Biotechnology, 2007, 25: 563 (incorporated by reference in its entirety).

In other embodiments of the invention, antibodies can be selected using mammalian cell display (Ho et al, PNAS, 2006, 103: 9637, incorporated by reference in its entirety).

The screening of the antibodies derived from the libraries of the invention can be carried out by any appropriate means. For example, binding activity can be evaluated by standard immunoassay and/or affinity chromatography. Screening of the antibodies of the invention for catalytic function, e.g., proteolytic function can be accomplished using a standard assays, e.g., the hemoglobin plaque assay as described in U.S. Pat. No. 5,798,208 (incorporated by reference in its entirety). Determining the ability of candidate antibodies to bind therapeutic targets can be assayed in vitro using, e.g., a BIACORE™ instrument, which measures binding rates of an antibody to a given target or antigen based on surface plasmon resonance. In vivo assays can be conducted using any of a number of animal models and then subsequently tested, as appropriate, in humans. Cell-based biological assays are also contemplated.

One aspect of the instant invention is the speed at which the antibodies of the library can be expressed and screened. In certain embodiments of the invention, the antibody library can be expressed in yeast, which have a doubling time of less than about 3, 4, 5, 6, 7, 8, 9, 10, 11, 12, 13, 14, 15, 16, 17, 18, 19, 20, 21, 22, 23, or 24 hours. In some embodiments, the doubling times are about 1 to about 3 hours, about 2 to about 4, about 3 to about 8 hours, about 3 to about 24, about 5 to about 24, about 4 to about 6 about 5 to about 22, about 6 to about 8, about 7 to about 22, about 8 to about 10 hours, about 7 to about 20, about 9 to about 20, about 9 to about 18, about 11 to about 18, about 11 to about 16, about 13 to about 16, about 16 to about 20, or about 20 to about 30 hours. In certain embodiments of the invention, the antibody library is expressed in yeast with a doubling time of about 16 to about 20 hours, about 8 to about 16 hours, or about 4 to about 8 hours. Thus, the antibody library of the instant invention can be expressed and screened in a matter of hours, as compared to previously known techniques which take several days to express and screen antibody libraries. A limiting step in the throughput of such screening processes in mammalian cells is simply the time required to iteratively regrow populations of isolated cells, which, in some cases, have doubling times greater than the doubling times of the yeast used in the current invention. In certain embodiments of the invention, the composition of a library may be defined after one or more enrichment steps (for example by screening for antigen binding, or other properties). For example, a library with a composition comprising about x % sequences or libraries of the invention may be enriched to contain about 2x %, 3x %, 4x %, 5x %, 6x %, 7x %, 8x %, 9x %, 10x %, 20x %, 25x %, 40x %, 50x %, 60x % 75x %, 80x %, 90x %, 95x %, or 99x % sequences or libraries of the invention, after one or more screening steps. In other embodiments of the invention, the sequences or libraries of the invention may be enriched about 2-fold, 3-fold, 4-fold, 5-fold, 6-fold, 7-fold, 8-fold, 9-fold, 10-fold, 100-fold, 1,000-fold, or more, relative to their occurrence prior to the one or more enrichment steps. In certain embodiments of the invention, a library may contain at least a certain number of a particular type of sequence(s), such as CDRH3 s, CDRL3 s, heavy chains, light chains, or whole antibodies (e.g., at least about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, or $10^{20}$). In certain embodiments, these sequences may be enriched during one or more enrichment steps, to provide libraries comprising at least about $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, or $10^{19}$ of the respective sequence(s).

As described above, antibody leads can be identified through a selection process that involves screening the antibodies of a library of the invention for binding to one or more antigens, or for a biological activity. The coding sequences of these antibody leads may be further mutagenized in vitro or in vivo to generate secondary libraries with diversity introduced in the context of the initial antibody leads. The mutagenized antibody leads can then be further screened for binding to target antigens or biological activity, in vitro or in vivo, following procedures similar to those used for the selection of the initial antibody lead from the primary library. Such mutagenesis and selection of primary antibody leads effectively mimics the affinity maturation process naturally occurring in a mammal that produces antibodies with progressive increases in the affinity to an antigen. In one embodiment of the invention, only the CDRH3 region is mutagenized. In another embodiment of the invention, the whole variable region is mutagenized. In other embodiments of the invention one or more of CDRH1, CDRH2, CDRH3, CDRL1, CDRL2, and/CDRL3 may be mutagenized. In some embodiments of the invention, "light chain shuffling" may be used as part of the affinity maturation protocol. In certain embodiments, this may involve pairing one or more heavy chains with a number of light chains, to select light chains that enhance the affinity and/or biological activity of an antibody. In certain embodiments of the invention, the number of light chains to which the one or more heavy chains can be paired is at least about 2, 5, 10, 100, 1000, $10^4$, $10^5$, $10^6$, $10^7$, $10^8$, $10^9$, or $10^{10}$. In certain embodiments of the invention, these light chains are encoded by plasmids. In other embodiments of the invention, the light chains may be integrated into the genome of the host cell.

The coding sequences of the antibody leads may be mutagenized by a wide variety of methods. Examples of methods of mutagenesis include, but are not limited to site-directed mutagenesis, error-prone PCR mutagenesis, cassette mutagenesis, and random PCR mutagenesis. Alternatively, oligonucleotides encoding regions with the desired mutations can be synthesized and introduced into the sequence to be mutagenized, for example, via recombination or ligation. Site-directed mutagenesis or point mutagenesis may be used to gradually change the CDR sequences in specific regions. This may be accomplished by using oligonucleotide-directed mutagenesis or PCR. For example, a short sequence of an antibody lead may be replaced with a synthetically mutagenized oligonucleotide in either the heavy chain or light chain region, or both. The method may not be efficient for mutagenizing large numbers of CDR sequences, but may be used for fine tuning of a particular lead to achieve higher affinity toward a specific target protein.

Cassette mutagenesis may also be used to mutagenize the CDR sequences in specific regions. In a typical cassette mutagenesis, a sequence block, or a region, of a single template is replaced by a completely or partially randomized sequence. However, the maximum information content that can be obtained may be statistically limited by the number of random sequences of the oligonucleotides. Similar to point mutagenesis, this method may also be used for fine tuning of a particular lead to achieve higher affinity towards a specific target protein.

Error-prone PCR, or "poison" PCR, may be used to mutagenize the CDR sequences by following protocols described in Caldwell and Joyce, PCR Methods and Applications, 1992, 2: 28; Leung et al, Technique, 1989, 1: 11; Shafikhani et al, Biotechniques, 1997, 23: 304; and Stemmer et al, PNAS, 1994, 91: 10747 (each of which is incorporated by reference in its entirety).

Conditions for error prone PCR may include (a) high concentrations OfMn$^{2+}$ (e.g., about 0.4 to about 0.6 mM) that efficiently induces malfunction of Taq DNA polymerase; and (b) a disproportionally high concentration of one nucleotide substrate (e.g., dGTP) in the PCR reaction that causes incorrect incorporation of this high concentration substrate into the template and produces mutations. Additionally, other factors such as, the number of PCR cycles, the species of DNA polymerase used, and the length of the template, may affect the rate of misincorporation of "wrong" nucleotides into the PCR product. Commercially available kits may be utilized for the mutagenesis of the selected antibody library, such as the "Diversity PCR random mutagenesis kit" (CLONTECH™). The primer pairs used in PCR-based mutagenesis may, in certain embodiments, include regions matched with the homologous recombination sites in the expression vectors. This design allows facile re-introduction of the PCR products back into the heavy or light chain chassis vectors, after mutagenesis, via homologous recombination. Other PCR-based mutagenesis methods can also be used, alone or in conjunction with the error prone PCR described above. For example, the PCR amplified CDR segments may be digested with DNase to create nicks in the double stranded DNA. These nicks can be expanded into gaps by other exonucleases such as Bal 31. The gaps may then be filled by random sequences by using DNA Klenow polymerase at a low concentration of regular substrates dGTP, dATP, dTTP, and dCTP with one substrate (e.g., dGTP) at a disproportionately high concentration. This fill-in reaction should produce high frequency mutations in the filled gap regions. These method of DNase digestion may be used in conjunction with error prone PCR to create a high frequency of mutations in the desired CDR segments. The CDR or antibody segments amplified from the primary antibody leads may also be mutagenized in vivo by exploiting the inherent ability of mutation in pre-B cells. The Ig genes in pre-B cells are specifically susceptible to a high-rate of mutation. The Ig promoter and enhancer facilitate such high rate mutations in a pre-B cell environment while the pre-B cells proliferate. Accordingly, CDR gene segments may be cloned into a mammalian expression vector that contains a human Ig enhancer and promoter. This construct may be introduced into a pre-B cell line, such as 38B9, which allows the mutation of the VH and VL gene segments naturally in the pre-B cells (Liu and Van Ness, Mol. Immunol., 1999, 36: 461, incorporated by reference in its entirety). The mutagenized CDR segments can be amplified from the cultured pre-B cell line and re-introduced back into the chassis-containing vector(s) via, for example, homologous recombination.

In some embodiments, a CDR "hit" isolated from screening the library can be re-synthesized, using degenerate codons or trinucleotides, and re-cloned into the heavy or light chain vector using gap repair.

In certain embodiments of the invention, a library of the invention comprises a designed, non-random repertoire wherein the theoretical diversity of particular components of the library (for example, CDRH3), but not necessarily all components or the entire library, can be over-sampled in a physical realization of the library, at a level where there is a certain degree of statistical confidence (e.g., 95%) that any given member of the theoretical library is present in the physical realization of the library at least at a certain frequency (e.g., at least once, twice, three times, four times, five times, or more) in the library.

In a library, it is generally assumed that the number of copies of a given clone obeys a Poisson probability distribution (see Feller, W. An Introduction to Probability Theory and Its Applications, 1968, Wiley New York, incorporated by reference in its entirety). The probability of a Poisson random number being zero, corresponding to the probability of missing a given component member in an instance of a library (see below), is $e^{-N}$, where N is the average of the random number. For example, if there are $10^6$ possible theoretical members of a library and a physical realization of the library has $10^7$ members, with an equal probability of each member of the theoretical library being sampled, then the average number of times that each member occurs in the physical realization of the library is $10^7/10^6=10$, and the probability that the number of copies of a given member is zero is $e^{-N}=e^{-10}=0.000045$; or a 99.9955% chance that there is at least one copy of any of the $10^6$ theoretical members in this 10× oversampled library. For a 2.3× oversampled library one is 90% confident that a given component is present. For a 3× oversampled library one is 95% confident that a given component is present. For a 4.6× oversampled library one is 99% confident a given clone is present, and so on.

Therefore, if M is the maximum number of theoretical library members that can be feasibly physically realized, then Mβ is the maximum theoretical repertoire size for which one can be 95% confident that any given member of the theoretical library will be sampled. It is important to note that there is a difference between a 95% chance that a given member is represented and a 95% chance that every possible member is represented. In certain embodiments, the instant invention provides a rationally designed library with diversity so that any given member is 95% likely to be represented in a physical realization of the library. In other embodiments of the invention, the library is designed so that any given member is at least about 0.0001%, 0.001%, 0.01%, 0.1%, 1%, 5%, 10%, 20%, 30%, 40%, 50%, 60%, 70%, 80%, 85%, 90%, 95%, 99%, 99.5%, or 99.9% likely to be represented in a physical realization of the library. For a review, see, e.g., Firth and Patrick, Biomol. Eng., 2005, 22: 105, and Patrick et al, Protein Engineering, 2003, 16: 451, each of which is incorporated by reference in its entirety. In certain embodiments of the invention, a library may have a theoretical total diversity of X unique members and the physical realization of the theoretical total diversity may contain at least about 1×, 2×, 3×, 4×, 5×, 6×, 7×, 8× 9×, 10×, or more members. In some embodiments, the physical realization of the theoretical total diversity may contain about 1× to about 2×, about 2× to about 3×, about 3× to about 4×, about 4× to about 5×, about 5× to about 6× members. In other embodiments, the physical realization of the theoretical total diversity may contain about 1× to about 3×, or about 3× to about 5× total members.

An assumption underlying all directed evolution experiments is that the amount of molecular diversity theoretically possible is enormous compared with the ability to synthesize it, physically realize it, and screen it. The likelihood of finding a variant with improved properties in a given library is maximized when that library is maximally diverse. Patrick et al. used simple statistics to derive a series of equations and computer algorithms for estimating the number of unique sequence variants in libraries constructed by randomized oligonucleotide mutagenesis, error-prone PCR and in vitro recombination. They have written a suite of programs for calculating library statistics, such as GLUE, GLUE-IT, PEDEL, PEDEL-AA, and DRIVeR. These programs are described, with instructions on how to access them, in Patrick et al, Protein Engineering, 2003, 16: 451 and Firth et al, Nucleic Acids Res., 2008, 36: W281 (each of which is incorporated by reference in its entirety).

It is possible to construct a physical realization of a library in which some components of the theoretical diversity (such as CDRH3) are oversampled, while other aspects (VH/VL pairings) are not. For example, consider a library in which $10^8$ CDRH3 segments are designed to be present in a single VH chassis, and then paired with $10^5$ VL genes to produce $10^{13}$ ($=10^8*10^5$) possible full heterodimeric antibodies. If a physical realization of this library is constructed with a diversity of $10^9$ transformant clones, then the CDRH3 diversity is oversampled ten-fold ($=10^9/10^8$), however the possible VH/VL pairings are undersampled by $10^{-4}$ ($=10^9/10^{13}$). In this example, on average, each CDRH3 is paired only with 10 samples of the VL from the possible $10^5$ partners. In certain embodiments of the invention, it is the CDRH3 diversity that is preferably oversampled.

In certain embodiments, the invention relates to a polynucleotide that hybridizes with a polynucleotide taught herein, or that hybridizes with the complement of a polynucleotide taught herein. For example, an isolated polynucleotide that remains hybridized after hybridization and washing under low, medium, or high stringency conditions to a polynucleotide taught herein or the complement of a polynucleotide taught herein is encompassed by the present invention.

Exemplary low stringency conditions include hybridization with a buffer solution of about 30% to about 35% formamide, about 1 M NaCl, about 1% SDS (sodium dodecyl sulphate) at about 37° C., and a wash in about 1× to about 2×SSC (20×SSC=3.0 M NaCl/0.3 M trisodium citrate) at about 50° C. to about 55° C.

Exemplary moderate stringency conditions include hybridization in about 40% to about 45% formamide, about 1 M NaCl, about 1% SDS at about 37° C., and a wash in about 0.5× to about 1×SSC at abut 55° C. to about 60° C.

Exemplary high stringency conditions include hybridization in about 50% formamide, about 1 M NaCl, about 1% SDS at about 37° C., and a wash in about 0.1×SSC at about 60° C. to about 65° C.

Optionally, wash buffers may comprise about 0.1% to about 1% SDS. The duration of hybridization is generally less than about 24 hours, usually about 4 to about 12 hours.

As described throughout the application, the libraries for use of the current invention are distinguished, in certain embodiments, by their human-like sequence composition and length, and the ability to generate a physical realization of the library which contains all members of (or, in some cases, even oversamples) a particular component of the library. Use of libraries comprising combinations of the libraries described herein (e.g., CDRH3 and CDRL3 libraries) are encompassed by the invention. Sub-libraries comprising portions of the libraries described herein are also encompassed by the invention (e.g., a CDRH3 library in a particular heavy chain chassis or a sub-set of the CDRH3 libraries). One of ordinary skill in the art will readily recognize that each of the libraries described herein has several components (e.g., CDRH3, VH, CDRL3, VL, etc.), and that the diversity of these components can be varied to produce sub-libraries that fall within the scope of the invention.

Moreover, libraries containing one of the libraries or sub-libraries of the invention also fall within the scope of the invention. For example, in certain embodiments of the invention, one or more libraries or sub-libraries of the invention may be contained within a larger library, which may include sequences derived by other means, for example, non-human or human sequence derived by stochastic or semi-stochastic synthesis. In certain embodiments of the invention, at least about 1% of the sequences in a polynucleotide library may be those of the invention (e.g., CDRH3 sequences, CDRL3 sequences, VH sequences, VL sequences), regardless of the composition of the other 99% of sequences. In other embodiments of the invention, at least about 0.001%, 0.01%, 0.1%, 2%, 5%, 10%, 20%, 30%, 40%, 50%, 60%, 70%, 80%, 81%, 82%, 83%, 84%, 85%, 86%, 87%, 88%, 89%, 90%, 91,%, 92%, 93%, 94%, 95%, 96%, 97%, 98% or 99% of the sequences in any polynucleotide library may be those of the invention, regardless of the composition of the other sequences. In some embodiments, the sequences of the invention may comprise about 0.001% to about 1%, about 1% to about 2%, about 2% to about 5%, about 5% to about 10%, about 10% to about 15%, about 15% to about 20%, about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 99% of the sequences in any polynucleotide library, regardless of the composition of the other sequences. Thus, libraries more diverse than one or more libraries or sub-libraries of the invention, but yet still comprising one or more libraries or sub-libraries of the invention, in an amount in which the one or more libraries or sub-libraries of the invention can be effectively screened and from which sequences encoded by the one or more libraries or sub-libraries of the invention can be isolated, also fall within the scope of the invention.

In certain embodiments of the invention, the amino acid products of a library of the invention (e.g., a CDRH3 or CDRL3) may be displayed on an alternative scaffold. Several of these scaffolds have been shown to yield molecules with specificities and affinities that rival those of antibodies. Exemplary alternative scaffolds include those derived from fibronectin (e.g., AdNectin), the β-sandwich (e.g., iMab), lipocalin (e.g., Anticalin), EETI-II/AGRP, BPTI/LACI-D1/ITI-D2 (e.g., Kunitz domain), thioredoxin (e.g., peptide aptamer), protein A (e.g., Affibody), ankyrin repeats (e.g., DARPin), γB-crystallin/ubiquitin (e.g., Affilin), CTLD3 (e.g., Tetranectin), and (LDLR-A moduleˆ (e.g., Avimers). Additional information on alternative scaffolds are provided in Binz et ah, Nat. BiotechnoL, 2005 23: 1257 and Skerra, Current Opin. in Biotech., 2007 18: 295-304, each of which is incorporated by reference in its entirety.

Additional exemplary, non-limiting embodiments of the invention are set forth below:

Embodiment 1. A method of broadening epitopic coverage of an antigen of interest, the method comprising:
- a) contacting a first sample of the antigen of interest with a first plurality of host cells collectively expressing a first library of antibodies;
- b) collecting host cells expressing antibodies that bind to the antigen from among the first plurality of host cells employed in step a);
- c) preparing a composition comprising a polyclonal mixture of antibodies expressed by host cells collected in step b);
- d) contacting a second sample of the antigen of interest with an aliquot of the composition prepared in step c) and a second plurality of host cells collectively expressing a second library of antibodies; and
- e) after performing step d), collecting host cells from among the second plurality of host cells expressing antibodies that bind to the second sample of the antigen from among the second plurality of host cells;
- wherein an increase in the number of different epitopes collectively recognized by the antibodies expressed by the host cells collected in step e) relative to the number of different epitopes collectively recognized by the antibodies contained in the composition prepared in step b) indicates that epitopic coverage of the antigen has been broadened.

Embodiment 2. A method of normalizing epitopic coverage of an antigen of interest, the method comprising:
- a) contacting a first sample of the antigen of interest with a first plurality of host cells collectively expressing a first library of antibodies;
- b) collecting host cells expressing antibodies that bind to the antigen from among the first plurality of cells employed in step a);
- c) preparing a composition comprising a polyclonal mixture of antibodies expressed by host cells collected in step b);
- d) contacting a second sample of the antigen of interest with an aliquot of the composition prepared in step c) and a second plurality of host cells collectively expressing a second library of antibodies;
- e) after performing step d), collecting host cells from among the second plurality of host cells expressing antibodies that bind to the second sample of the antigen from among the second plurality of host cells,
- wherein either:
  - i) an increase in the number of different antibodies expressed by the host cells collected in step e) that bind to at least one under-represented epitope relative to the number of different antibodies contained in the composition prepared in step c) that bind the at least one under-represented epitope;
  - ii) a decrease in the number of different antibodies expressed by the host cells collected in step e) that bind to at least one over-represented epitope relative to the number of different antibodies contained in the composition prepared in step c) that bind the at least one over-represented epitope; or
  - iii) both i) and ii);
- indicates that the epitopic coverage of the antigen of interest has been normalized.

Embodiment 3. A method of reducing selection bias towards at least one dominant epitope of an antigen of interest, the method comprising:
- a) contacting a first sample of the antigen of interest with a first plurality of host cells collectively expressing a first library of antibodies;
- b) collecting host cells expressing antibodies that bind to the antigen from among the first plurality of cells employed in step a);
- c) preparing a composition comprising a polyclonal mixture of antibodies expressed by host cells collected in step b), wherein the composition comprises at least one antibody that recognizes at least one epitope on the antigen;
- d) contacting a second sample of the antigen of interest with an aliquot of the composition prepared in step c) and a second plurality of host cells collectively expressing a second library of antibodies;
- wherein the at least one epitope is made less available for binding by antibodies contained in the second plurality of antibodies as a result of contacting the second sample of the antigen of interest with the composition prepared in step c), thereby reducing bias towards the at least one epitope on the antigen.

Embodiment 4. A method of blocking at least one dominant epitope of an antigen of interest, the method comprising:
- a) contacting a first sample of the antigen of interest with a first plurality of host cells collectively expressing a first library of antibodies;
- b) collecting host cells expressing antibodies that bind to the antigen from among the first plurality of cells employed in step a);
- c) preparing a composition comprising a polyclonal mixture of antibodies expressed by host cells collected in in step b), wherein the composition comprises at least one antibody that recognizes at least one dominant epitope on the antigen;
- d) contacting a second sample of the antigen of interest with an aliquot of the composition prepared in step c) and a second plurality of host cells collectively expressing a second library of antibodies;
- wherein the at least one dominant epitope is blocked by the at least one antibody in the mixture prepared in step c).

Embodiment 5. A method of identifying at least one host cell that expresses an antibody with specificity for a rare epitope on an antigen of interest, the method comprising:
- a) contacting a first sample of the antigen of interest with a first plurality of host cells collectively expressing a first library of antibodies;
- b) collecting host cells expressing antibodies that bind to the antigen from among the first plurality of cells employed in step a);
- c) preparing a composition comprising a polyclonal mixture of antibodies expressed by host cells collected in step b), wherein the composition comprises at least one antibody that recognizes at least one dominant epitope on the antigen;
- d) contacting a second sample of the antigen of interest with an aliquot of the composition prepared in step c) and a second plurality of host cells collectively expressing a second library of antibodies;
- e) after performing step d), collecting at least one host cell from among the second plurality of host cells that expresses an antibody that binds to the rare epitope, thereby identifying the at least one host cell that expresses the antibody with specificity for the rare epitope.

Embodiment 6. A method of identifying at least one antibody with specificity for a rare epitope on an antigen, the method comprising:
a) contacting a first sample of the antigen of interest with a first plurality of host cells collectively expressing a first library of antibodies;
b) collecting host cells expressing antibodies that bind to the antigen from among the first plurality of cells employed in step a);
c) preparing a composition comprising a polyclonal mixture of antibodies expressed by host cells collected in step b), wherein the composition comprises at least one antibody that recognizes at least one dominant epitope on the antigen;
d) contacting a second sample of the antigen of interest with an aliquot of the composition prepared in step c) and a second plurality of host cells collectively expressing a second library of antibodies;
e) after performing step d), identifying at least one antibody expressed by at least one host cell from among the second plurality of host cells having specificity for an epitope that is under-represented in the composition prepared in step c).

Embodiment 7. The method according to embodiment 6, wherein the at least one antibody that is identified in step e) constitutes an antibody that has specificity toward a rare epitope on the antigen of interest.

Embodiment 8. A method of enriching for antibodies having specificity towards at least one rare epitope of an antigen in an antibody selection process, the method comprising:
a) contacting a first sample of the antigen of interest with a first plurality of host cells collectively expressing a first library of antibodies;
b) collecting host cells expressing antibodies that bind to the antigen from among the first plurality of cells employed in step a);
c) preparing a composition comprising a polyclonal mixture of antibodies expressed by host cells collected in step b), wherein the composition comprises at least one antibody that recognizes at least one dominant epitope on the antigen;
d) contacting a second sample of the antigen of interest with an aliquot of the composition prepared in step c) and a second plurality of host cells collectively expressing a second library of antibodies, thereby blocking the at least one dominant epitope;
e) after performing step d), collecting host cells from among the second plurality of host cells that express antibodies with specificity to the at least one rare epitope;
wherein the number of different antibodies having specificity to the at least one rare epitope expressed from host cells collected in step e) is greater than the number of antibodies having specificity to the at least one rare epitope expressed from host cells collected in step b).

Embodiment 9. A method of broadening epitopic coverage of an antigen of interest, the method comprising:
a) contacting a first sample of the antigen of interest with a first library of antibodies;
b) collecting antibodies that bind to the antigen from among the first sample employed in step a);
c) preparing a composition comprising a polyclonal mixture of antibodies collected in step b);
d) contacting a second sample of the antigen of interest with an aliquot of the composition prepared in step c) and a second library of antibodies; and
e) after performing step d), collecting antibodies that bind to the second sample of the antigen from among the second library of antibodies employed in the contacting step d);
wherein an increase in the number of different epitopes collectively recognized by the antibodies collected in step e) relative to the number of different epitopes collectively recognized by the antibodies contained in the composition prepared in step b) indicates that epitopic coverage of the antigen has been broadened.

Embodiment 10. A method of normalizing epitopic coverage of an antigen of interest, the method comprising:
a) contacting a first sample of the antigen of interest with a first library of antibodies;
b) collecting antibodies that bind to the antigen from among the first library of antibodies employed in step a);
c) preparing a composition comprising a polyclonal mixture of antibodies collected in step b);
d) contacting a second sample of the antigen of interest with an aliquot of the composition prepared in step c) and a second library of antibodies;
e) after performing step d), collecting antibodies that bind to the second sample of the antigen from among the second library of antibodies employed in the contacting step d),
wherein either:
i) an increase in the number of different antibodies collected in step e) that bind to at least one under-represented epitope relative to the number of different antibodies contained in the composition prepared in step c) that bind the at least one under-represented epitope;
ii) a decrease in the number of different antibodies collected in step e) that bind to at least one over-represented epitope relative to the number of different antibodies contained in the composition prepared in step c) that bind the at least one over-represented epitope; or
iii) both i) and ii);
indicates that the epitopic coverage of the antigen of interest has been normalized.

Embodiment 11. A method of reducing selection bias towards at least one dominant epitope of an antigen of interest, the method comprising:
a) contacting a first sample of the antigen of interest with a first library of antibodies;
b) collecting antibodies that bind to the antigen from among the first library of antibodies employed in step a);
c) preparing a composition comprising a polyclonal mixture of antibodies collected in step b), wherein the composition comprises at least one antibody that recognizes at least one epitope of the antigen;
d) contacting a second sample of the antigen of interest with an aliquot of the composition prepared in step c) and a second library of antibodies;
wherein the at least one epitope is made less available for binding by antibodies contained in the second plurality of antibodies as a result of contacting the second sample of the antigen of interest with the composition prepared in step c), thereby reducing bias towards the at least one epitope on the antigen.

Embodiment 12. A method of blocking at least one dominant epitope of an antigen of interest, the method comprising:
- a) contacting a first sample of the antigen of interest with a first library of antibodies;
- b) collecting antibodies that bind to the antigen from among the first library of antibodies employed in step a);
- c) preparing a composition comprising a polyclonal mixture of antibodies collected in in step b), wherein the composition comprises at least one antibody that recognizes at least one dominant epitope on the antigen;
- d) contacting a second sample of the antigen of interest with an aliquot of the composition prepared in step c) and a second library of antibodies;
- wherein the at least one dominant epitope is blocked by the at least one antibody in the mixture prepared in step c).

Embodiment 13. A method of identifying at least one antibody with specificity for a rare epitope on an antigen of interest, the method comprising:
- a) contacting a first sample of the antigen of interest with a first library of antibodies;
- b) collecting antibodies that bind to the antigen from among the first library of antibodies employed in step a);
- c) preparing a composition comprising a polyclonal mixture of antibodies collected in step b), wherein the composition comprises at least one antibody that recognizes at least one dominant epitope on the antigen;
- d) contacting a second sample of the antigen of interest with an aliquot of the composition prepared in step c) and a second library of antibodies;
- e) after performing step d), collecting at least antibody from the second library of antibodies that binds to the rare epitope.

Embodiment 14. A method of identifying at least one antibody with specificity for a rare epitope on an antigen, the method comprising:
- a) contacting a first sample of the antigen of interest with a first library of antibodies;
- b) collecting antibodies that bind to the antigen from among the first library of antibodies employed in step a);
- c) preparing a composition comprising a polyclonal mixture of antibodies collected in step b), wherein the composition comprises at least one antibody that recognizes at least one dominant epitope on the antigen;
- d) contacting a second sample of the antigen of interest with an aliquot of the composition prepared in step c) and a second library of antibodies;
- e) after performing step d), identifying at least one antibody from among the second sample of antibodies having specificity for an epitope that is under-represented in the composition prepared in step c).

Embodiment 15. The method according to embodiment 14, wherein the at least one antibody that is identified in step e) constitutes an antibody that has specificity toward a rare epitope on the antigen of interest.

Embodiment 16. A method of enriching for antibodies having specificity towards at least one rare epitope of an antigen in an antibody selection process, the method comprising:
- a) contacting a first sample of the antigen of interest with a first library of antibodies;
- b) collecting antibodies that bind to the antigen from among the first library of antibodies employed in step a);
- c) preparing a composition comprising a polyclonal mixture of antibodies collected in step b), wherein the composition comprises at least one antibody that recognizes at least one dominant epitope on the antigen;
- d) contacting a second sample of the antigen of interest with an aliquot of the composition prepared in step c) and a second library of antibodies, thereby blocking the at least one dominant epitope;
- e) after performing step d), collecting antibodies from among the second library of antibodies with specificity to the at least one rare epitope;
- wherein the number of different antibodies having specificity to the at least one rare epitope collected in step e) is greater than the number of antibodies having specificity to the at least one rare epitope collected in step b).

Embodiment 17. The method according to any one of embodiments 1 through 16, wherein the first and second libraries of antibodies of antibodies comprise the same antibodies.

Embodiment 18. The method according to any one of embodiments 1 through 17, wherein the first and second samples consist essentially of the same antibodies.

Embodiment 19. The method according to any one of embodiments 1 through 18, wherein the first and second samples consist of the same antibodies.

Embodiment 20. The method according to any one of embodiments 1 through 16, wherein the second library of antibodies comprises a subset of antibodies contained in the first library of antibodies.

Embodiment 21. The method according to any of embodiments 1 through 17 and 20, wherein the second library of antibodies comprises antibodies that are contained in the first library of antibodies as well as antibodies that are not contained in the first library of antibodies.

Embodiment 23. The method according to according to any one of embodiments 1 through 21, wherein one or both of the first and second libraries of antibodies each comprise one or more sub-libraries.

Embodiment 24. The method according to embodiment 22, wherein the one or more sub-libraries are physically are separated from one another.

Embodiment 25. The method according to any one of embodiments 1 through 23, wherein the antibodies comprise: full length immunoglobulins; full length IgGs; full length IgMs; full length IgEs; full length IgAs; variable domains, antibody fragments; linear antibodies, single chain antibodies; scFvs, Fv fragments; Fab fragments, Fab' fragments, (Fab')$_2$ fragments; multispecific antibodies; bispecific antibodies; trispecific antibodies; tetraspecific antibodies; humanized antibodies; and combinations thereof.

Embodiment 26. The method according to any one of embodiments 1 through 25, wherein at least one of the collecting or identifying steps comprises employing flow cytometry.

Embodiment 27. The method according to any one of embodiments 1 through 25, wherein at least one of the collecting or identifying steps comprises employing florescence-activated cell sorting (FACS).

Embodiment 28. The method according to any one of embodiments 1 through 26, wherein at least one of the collecting or identifying steps comprises employing magnetic assisted cell sorting (MACS).

Embodiment 29. The method according to any one of embodiments 1 through 8, wherein the host cells are prokaryotic cells.

Embodiment 30. The method according to any one of embodiments 1 through 9 and 28, wherein the host cells are bacterial cells.

Embodiment 31. The method according to any one of embodiments 1 through 9, 28, and 29, wherein the host cells are *E. coli* cells.

Embodiment 32. The method according to any one of embodiments 1 through 9, wherein the host cells are eukaryotic cells.

Embodiment 33. The method according to any one of embodiments 1 through 9 and 31, wherein the host cells are yeast cells.

Embodiment 34. The method according to any one of embodiments 1 through 9, 31, and 32 wherein the host cells are *Saccharomyces cerevisiae* cells.

Embodiment 35. The method according to any one of embodiments 1 through 9, 31, and 32 wherein the host cells are *Pichia pastoris* cells.

Embodiment 36. The method according to any one of embodiments 1 through 30 wherein either: the first library of antibodies; the second library of antibodies; or the first library of antibodies and the second library of antibodies; comprises a phage library.

Embodiment 37. The method according to any one of embodiments 1 through 9 and 17 through 35, wherein the first plurality of host cells and the second plurality of host cells are each transformed with a first library of polynucleotides and a second library of polynucleotides, each of which collectively encode the first library of antibodies and the second library of antibodies, respectively.

Embodiment 38. The method according to any one of embodiments 1 through 9 and 17 through 36, wherein the host cells collectively express the library of antibodies and present the antibodies on their cell surfaces.

Embodiment 39. A collection of antibodies obtained by performing a method according to any one of embodiments 1 through 37.

Embodiment 40. An antibody obtained by performing a method according to any one of embodiments 1 through 37.

Embodiment 41. A polyclonal mixture of antibodies prepared by a method comprising:
a) contacting an antigen of interest with a plurality of host cells collectively expressing a first library of antibodies;
b) collecting host cells expressing antibodies that bind to the antigen from among the plurality of host cells employed in step a);
c) preparing a composition comprising a polyclonal mixture of antibodies expressed by host cells collected in step b).

Embodiment 42. A polyclonal mixture of antibodies prepared by a method comprising:
a) contacting an antigen of interest with a library of antibodies;
b) collecting antibodies that bind to the antigen from among the library of antibodies employed in step a);
c) preparing a composition comprising a polyclonal mixture of antibodies from the antibodies collected in step b).

Embodiment 43. A polyclonal mixture of antibodies for use in a method according to any one of embodiments 1 through 37.

Embodiment 44. Use of a polyclonal mixture of antibodies in a method according to any one of embodiments 1 through 37.

Embodiment 44. A library of antibody heavy chains comprising antibodies representing heavy chain germlines VH3-23, VH1-69, VH1-46, VH4-39, VH4-34, VH3-9, VH3-30, VH3-33, VH3-07, VH3-48, VH3-21, VH3-72, VH1-2, VH1-18, VH5-51, VH3-66, VH4-31, VH4-61, VH4-59, and VH4-b.

Embodiment 45. A library of antibody light chains comprising antibodies representing light chain germlines Vk1-05, Vk1-12 Vk1-33, Vk1-39, Vk2-28, Vk3-11. Vk3-15, and VK3-20.

Embodiment 46. A library of antibody heavy chains comprising antibodies representing:
heavy chain germlines VH3-23, VH1-69, VH1-46, VH4-39, VH4-34, VH3-9, VH3-30, VH3-33, VH3-07, VH3-48, VH3-21, VH3-72, VH1-2, VH1-18, VH5-51, VH3-66, VH4-31, VH4-61, VH4-59, and VH4-b; and
light chain germlines Vk1-05, Vk1-12 Vk1-33, Vk1-39, Vk2-28, Vk3-11. Vk3-15, and VK3-20.

Embodiment 47. A library according to any one of embodiments 44 through 46 for use in preparing a polyclonal mixture of antibodies.

Embodiment 28. A library according to any one of embodiments 44 through 47 for use in preparing a polyclonal mixture of antibodies for use in a method according to any one of embodiments 1 through 37.

Examples

Materials and Methods

Antigens were biotinylated using the EZ-Link Sulfo-NHS-Biotinylation Kit from Pierce. Goat anti-human F(ab')$_2$ kappa-FITC (LC-FITC), Extravidin-PE (EA-PE) and streptavidin-633 (SA-633) were obtained from Southern Biotech, Sigma and Molecular Probes, respectively. Streptavidin MicroBeads and MACS LC separation columns were purchased from Miltenyi Biotec.

FACS Selections

Eight naïve human synthetic yeast libraries each of ~$10^9$ diversity were propagated as described previously (see, e.g., Xu et al, *Prot. Eng. Des. Sel.*, VOl. 26(10), pp. 663-670; 2013; WO2009036379; WO2010105256; WO2012009568). For the first two rounds of selection, a magnetic bead sorting technique utilizing the Miltenyi MACs system was performed, as described (Siegel et al., 2004). Briefly, yeast cells (~$10^{10}$ cells/library) were incubated with 3 ml of 100 nM biotinylated antigen for 10 min at room temperature in FACS wash buffer (phosphate-buffered saline (PBS)/0.1% bovine serum albumin (BSA)). After washing once with 50 ml ice-cold wash buffer, the cell pellet was resuspended in 40 mL wash buffer, and Streptavidin MicroBeads (500 µl) were added to the yeast and incubated for 15 min at 4° C. Next, the yeast were pelleted, resuspended in 5 mL wash buffer, and loaded onto a Miltenyi LS column. After the 5 mL was loaded, the column was washed 3 times with 3 ml FACS wash buffer. The column was then removed from the magnetic field, and the yeast were eluted with 5 mL of growth media and then grown overnight. The following two rounds of sorting were performed using flow cytometry. Approximately 1×$10^8$ yeast were pelleted, washed three times with wash buffer, and incubated with 100 nM biotinylated antigen for 10 min at room temperature. Yeast were then washed twice and stained with LC-FITC (diluted 1:100) and either SA-633 (diluted 1:500) or EA-PE (diluted 1:50) secondary reagents for 15 min at 4° C. After washing twice with ice-cold wash buffer, the cell pellets were resuspended in 0.4 mL wash buffer and transferred to strainer-capped sort tubes. Sorting was performed using a FACS ARIA sorter (BD Biosciences) and sort gates were determined to select only antigen binding clones. After the final round of sorting, yeast were plated and individual colonies were picked for characterization.

For selections that involved antigen blocking with polyclonal antibodies, the same procedure was followed except that 100 nM antigen was pre-incubated with 1 µM polyclonal antibody for 10 min at 30° C. before adding to the yeast libraries.

Polyclonal Antibody Production and Purification

Round 4 selection outputs were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over KappaSelect (GE Healthcare LifeSciences).

MSD-SET $K_D$ measurements

Equilibrium affinity measurements performed as previously described (Estep et al., *MAbs*, Vol. 5(2), pp. 270-278, (2013)). Solution equilibrium titrations (SET) were performed in PBS+0.1% IgG-Free BSA (PBSF) with antigen held constant at 100 pM or 200 pM and incubated with 3- to 5-fold serial dilutions of antibody starting at 300-500 nM. Antibodies (20 nM in PBS) were coated onto standard bind MSD-ECL plates overnight at 4° C. or at room temperature for 30 min. Plates were then blocked for 30 min with shaking at 700 rpm, followed by three washes with wash buffer (PBSF+0.05% Tween 20). SET samples were applied and incubated on the plates for 150s with shaking at 700 rpm followed by one wash. Antigen captured on a plate was detected with 250 ng/mL sulfotag-labeled streptavidin in PBSF by incubation on the plate for 3 min. The plates were washed three times with wash buffer and then read on the MSD Sector Imager 2400 instrument using 1× Read Buffer T with surfactant. The percent free antigen was plotted as a function of titrated antibody in Prism and fit to a quadratic equation to extract the $K_D$. To improve throughput, liquid handling robots were used throughout MSD-SET experiments, including SET sample preparation.

Octet Red384 Epitope Binning

Epitope binning was performed using a standard sandwich format binning assay. A first anti-target IgG was loaded onto AHQ sensors and unoccupied Fc-binding sites on the sensor were blocked with a non-relevant human IgG1 antibody. The sensors were then exposed to 100 nM target antigen followed by a second anti-target antibody. Data was processed using ForteBio's Data Analysis Software 7.0. Additional binding by the second antibody after antigen association indicates an unoccupied epitope (non-competitor), while no binding indicates epitope blocking (competitor). This process was iterated such that the highest affinity antibodies that had yet to show competitive binding were selected as the first IgG on sensors for successive experiments.

Results

Yeast Display Library Selections

Figure 2A:
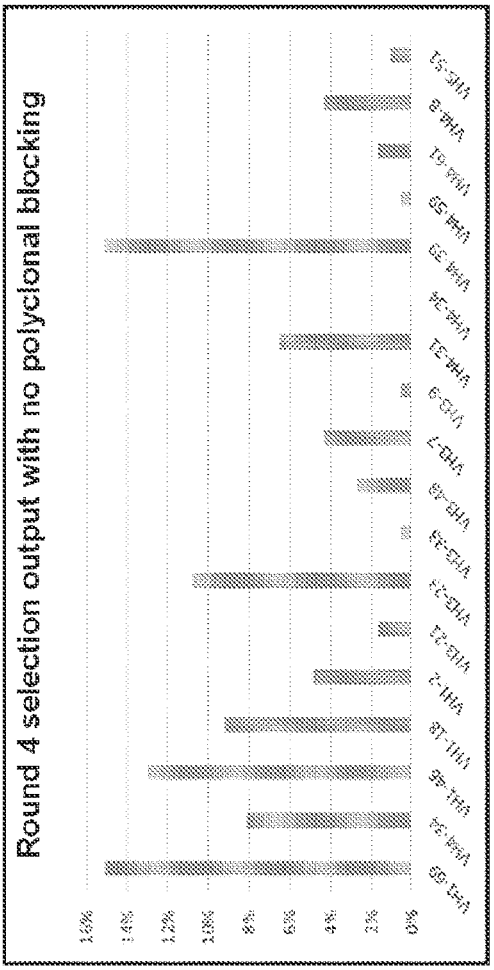
FIGS. 2A and 2B illustrate germline gene representation of unique IgGs from selection output in the presence and absence, respectively, of a polyclonal mixture of antibodies prepared as disclosed throughout and in the Examples.

Eight antibody libraries presented on the surface of yeast, each representing a different germline gene family or a combination of germline gene families (FIG. 11), were subject to multiple rounds of selection against a 53 kDa monomeric model antigen. Four rounds of selection, as described above, were performed to effect full enrichment for antigen-specific clones (FIG. 1). In the final round of selection, the entire antigen-binding population was sorted, plated, and 256 individual colonies were picked for sequence analysis and subsequent antibody production and characterization. Based on sequence analysis of the third complementarity-determining region of the heavy chain (CDR H3), 153 unique clones representing 17 different germline gene families were recovered (FIG. 2A).

Figure 4A:
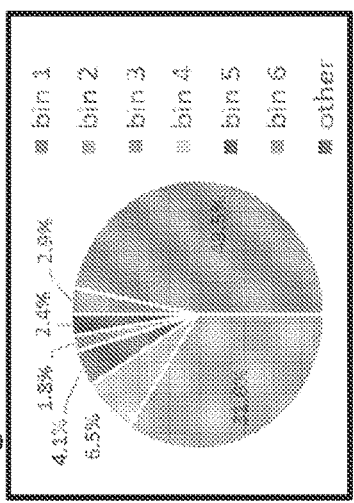
FIGS. 4A and 4B depict an epitope coverage analysis of the round 4 selection output as described in the Examples and depicted in FIG. 1. One hundred fifty-three (153) unique clones were recovered from the round 4 selections and produced as soluble IgGs for epitope binning analysis. Epitope binning was performed using a typical sandwich format, as described in the Examples.
Figure 4B:
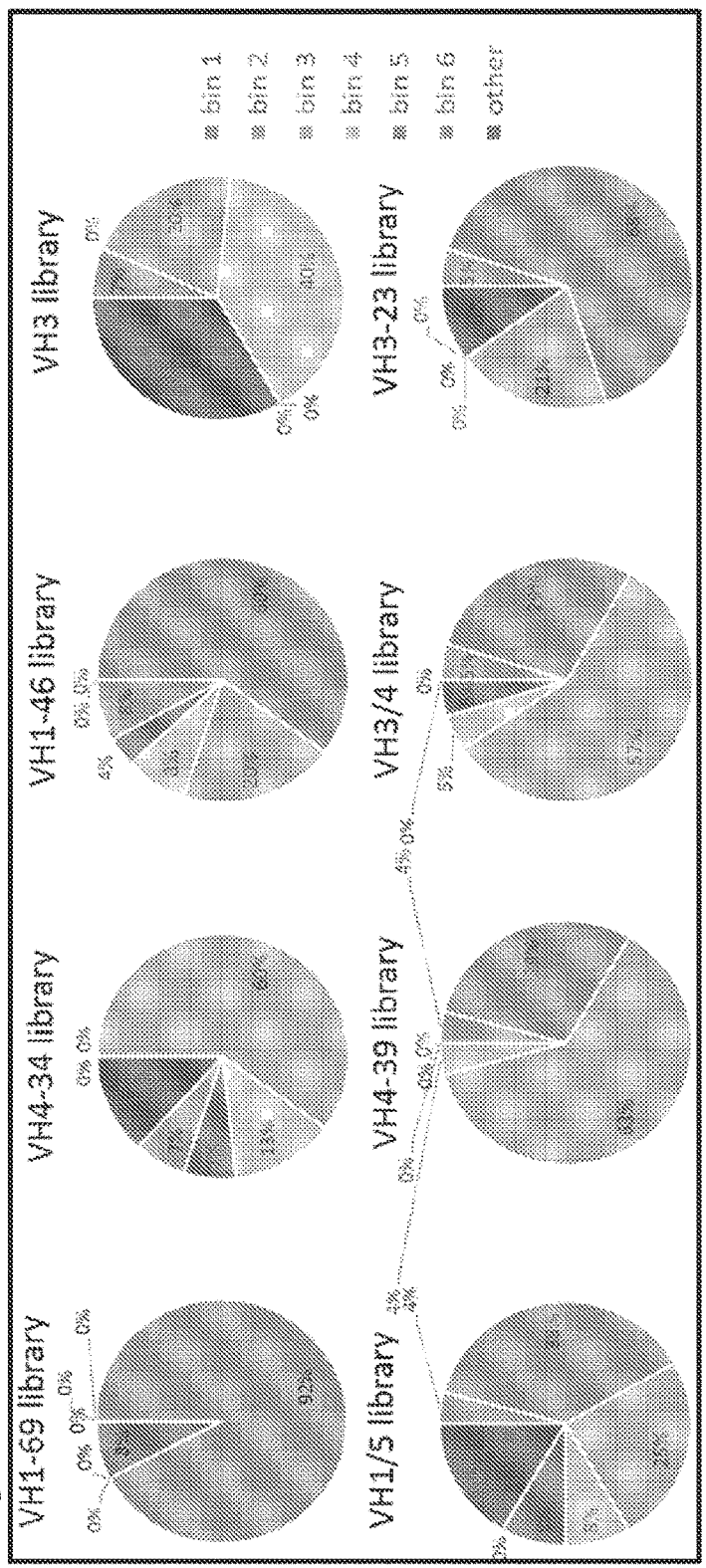

Antibody cross-competition assays were performed to determine the epitopic distribution of the selected clones (FIG. 4A). Based on these experiments, the majority of clones were assigned to one of six distinct epitope bins, and a small number of clones were grouped into an undefined rare bin category. Analysis of the results from all unique clones isolated from the eight libraries revealed that antibodies in bins 2 and 3 dominated the overall selection output (FIG. 1A). Interestingly, however, a strong germline-dependent preference for certain epitopes was observed when the cross-competition results were analyzed for each of the eight individual libraries separately (FIG. 4B). For example, the VH1-69 library yielded almost exclusively bin 2 clones, whereas the VH3 library output was skewed toward clones in bin 4 and undefined rare bins.

Figure 5:
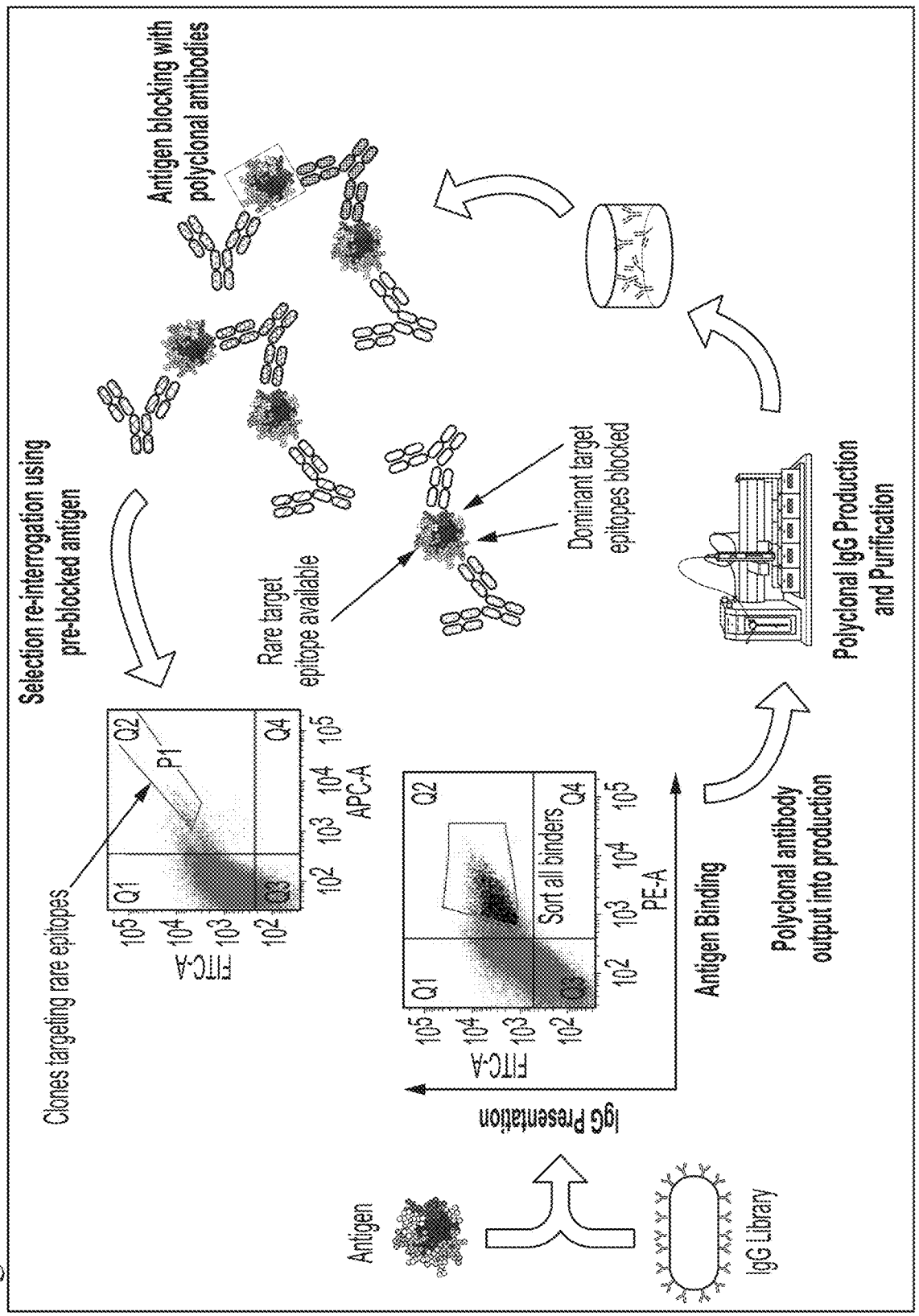
FIG. 5 illustrates an exemplary embodiment of an antibody selection scheme in which a polyclonal mixture of antibodies is employed. In the exemplary embodiment depicted in this Figure, the entire antigen-binding yeast host cell population was sorted and induced to secrete soluble IgGs. The polyclonal mixture of antibodies was then collected, and then contacted with the antigen and host cells during re-interrogation of the libraries as described in the Examples. Dominant epitopes are effectively blocked by antibodies in the polyclonal antibody mixture, and therefore unavailable for binding by libraries upon re-interrogation.
Figure 6:
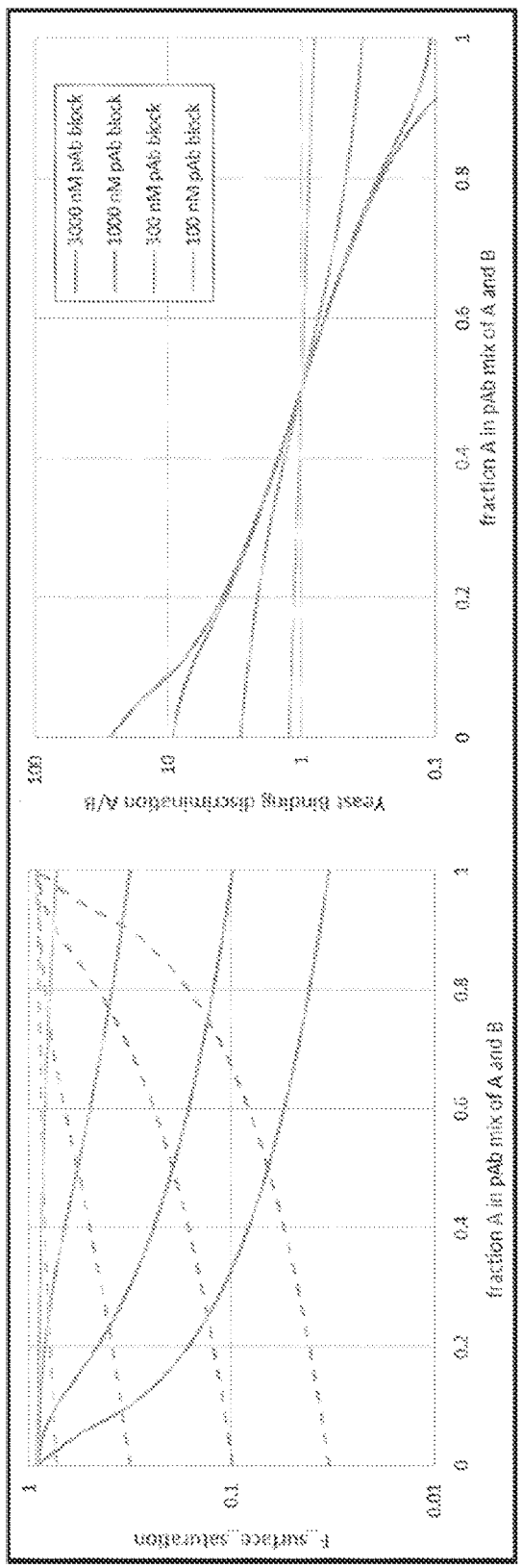
FIG. 6 illustrates a two-antibody two-epitope pre-blocking model, as described in the Examples. Two antibodies (labeled A and B on the x-axis of the Figure) of equal affinity ($K_D$) bind to independent epitopes on an antigen (Ag). A mixture of A and B (pAb block) is first equilibrated with Ag and the amount of free Ag still able to bind yeast containing monoclonal antibody (mAb) A or B is calculated. Assuming excess free Ag to surface mAb, the fractional yeast surface saturation (F_sat) of each mAb can be calculated by [Ag free]/([$K_D$]+[Ag free]). All calculations assume 100 nM Ag and 10 nM $K_D$ affinity of the clones. Left panel, F_sat for mAb A (solid lines) and mAb B (dashed lines) as a function of various ratios of A and B. Different colors represent varying amounts of polyclonal blocking antibodies. Right panel, the ratio of F_sat A to F_sat B as a function of various ratios of A and B. The discrimination of surface binding increases as the amount of polyclonal block increases and as the mixture of A and B becomes more unequally weighted.

Compositions Comprising Polyclonal Antibody Mixtures can be Used as Competitors in Selections To test whether epitopic distribution of antibodies having specificity for the antigen as reflected in, e.g., FIG. 4A and FIG. 4B could be normalized and/or antibodies that were under-represented in the initial selections could be enriched, polyclonal antibody mixtures from each of the round 4 library selection outputs were prepared to use as antigen-blocking reagents during re-interrogation of the round 4 selections, depicted graphically in FIG. 5. Without wishing to be bound by any theory, it was believed that clones targeting dominant epitopes would be present in this polyclonal mixture in higher proportions than clones targeting rarer epitopes, and should preferentially block those dominant epitopes from binding to yeast library clones. Indeed, theoretical calculations based on a simplified two antibody-two epitope model system support this belief (FIG. 6). Based on this model, the ability to discriminate between clones on the surface of yeast increases as the disparity in representation increases (level of domination), and when the ratio of blocking antibody to antigen increases.

Figure 2B:
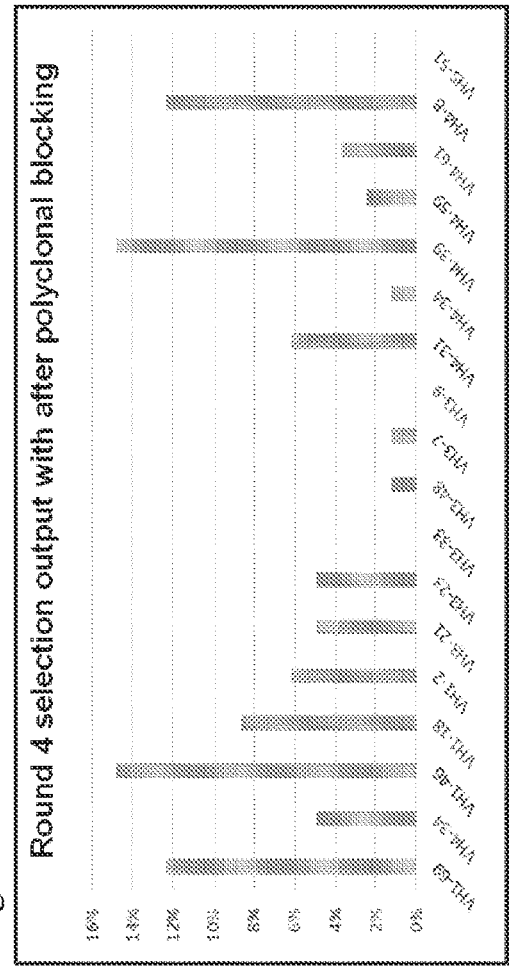
Figure 3A:
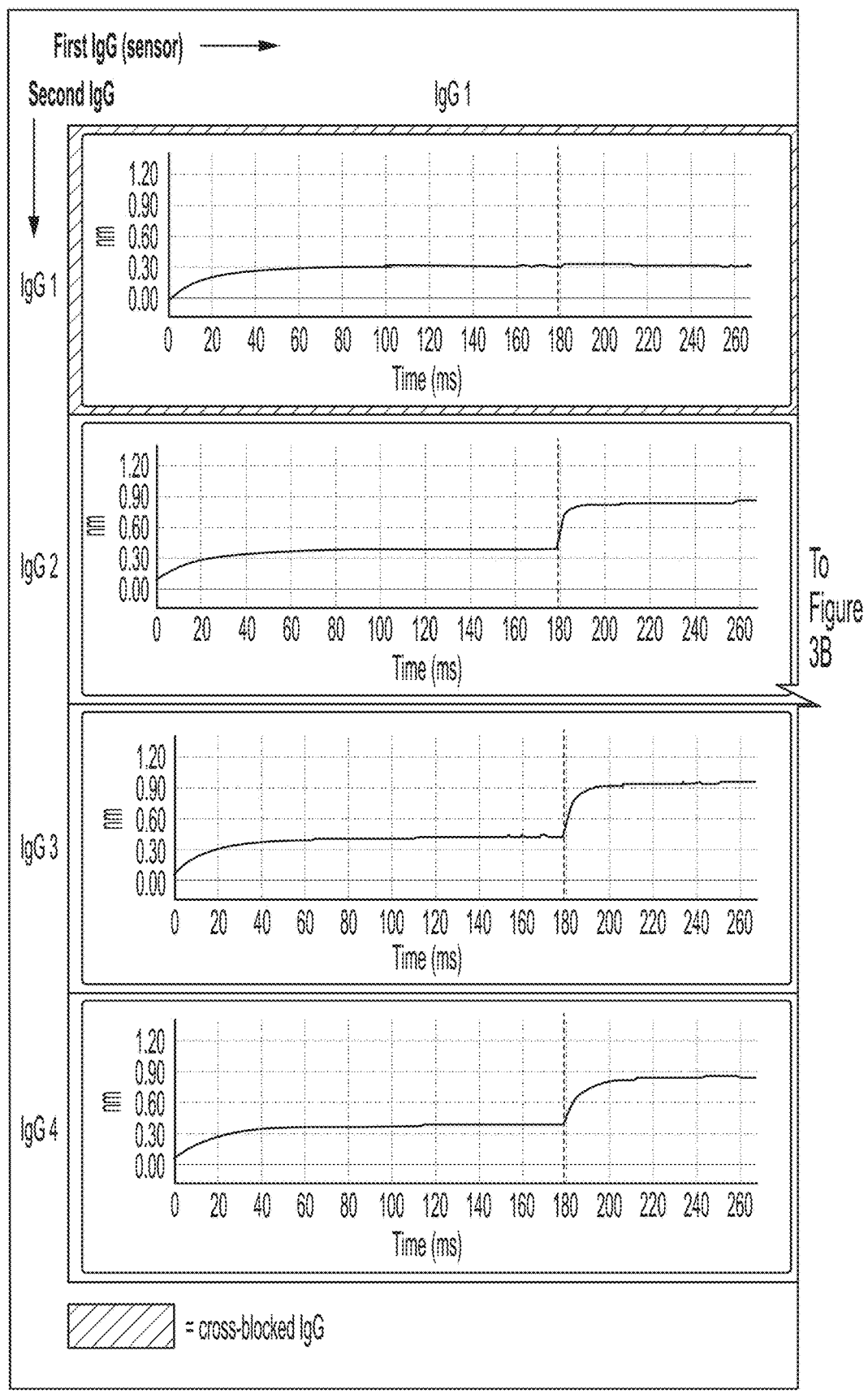
FIG. 3A, FIG. 3B, FIG. 3C, and FIG. 3D depict results of an exemplary cross-binning experiment as described, e.g., in the Examples. A first anti-target antibody (e.g., "IgG 1") was loaded onto AHQ sensors and allowed to associate with the target antigen, followed by the loading of a second anti-target antibody (e.g., IgG 2"). Additional binding by the second anti-target antibody indicates that the second antibody is not a competitor of the first antibody (indicated in non-shaded plots in the Figure). Lack of binding by the second anti-target antibody indicates that the second antibody is a competitor of the first antibody (depicted as "cross-blocked IgG" and shaded in the Figures).
Figure 3B:
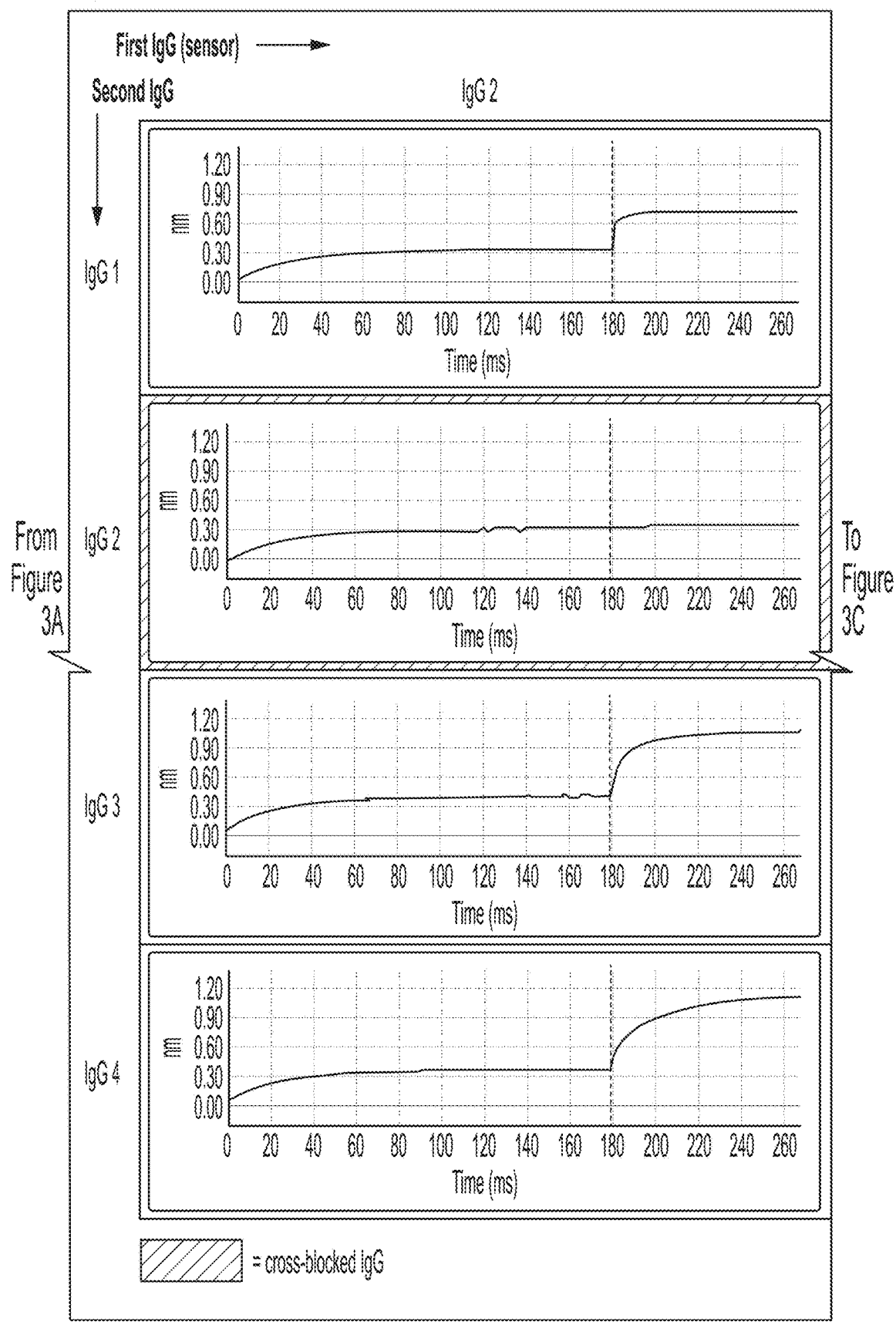
Figure 3C:
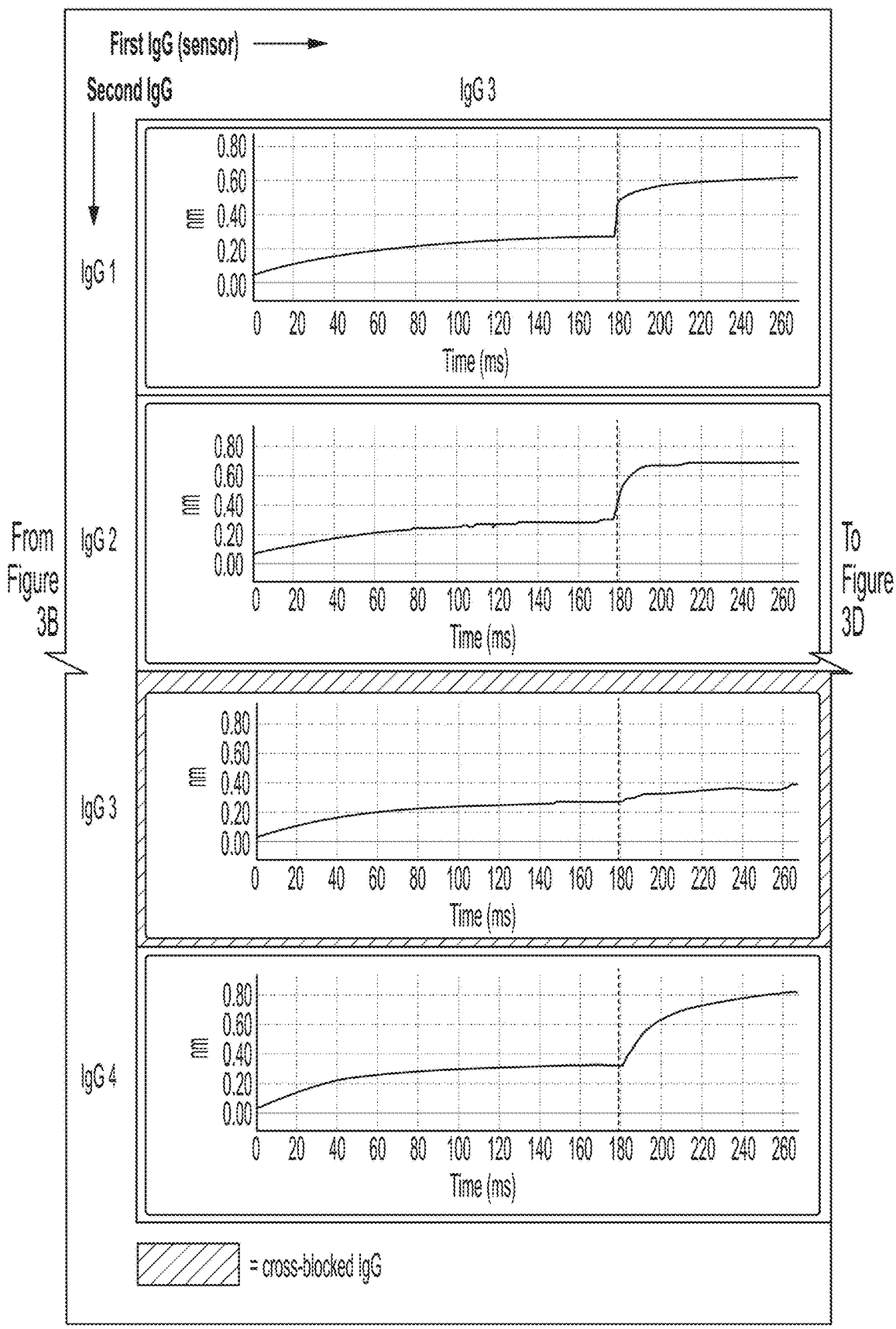
Figure 3D:
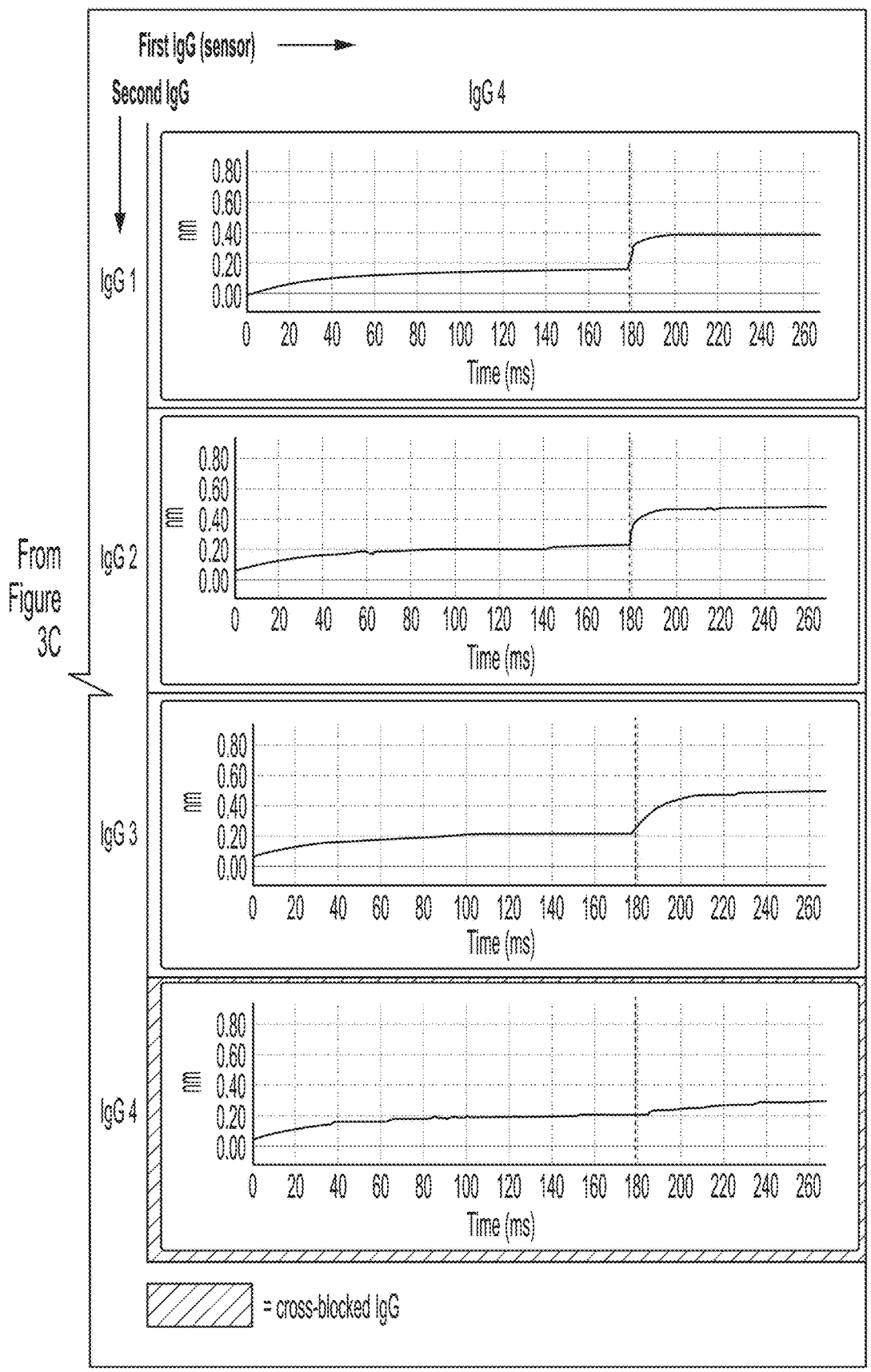
Figure 7A:
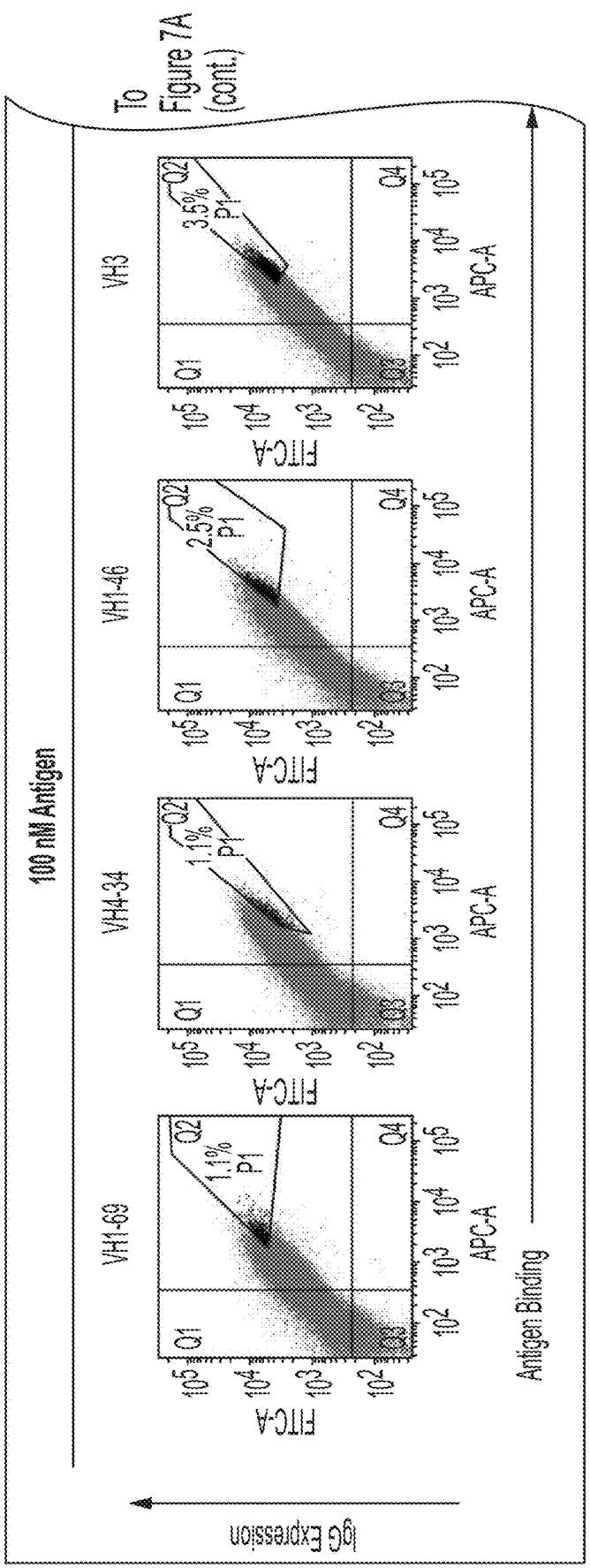
FIGS. 7A and 7B depict yeast-binding populations for the eight depicted individual germline libraries in the absence (FIG. 7A) and presence (FIG. 7B) of an exemplary polyclonal mixture of antibodies. Percentages represent populations in polygon gate. The same gates shown in each plot in FIG. 7A were used in the corresponding plots depicted in FIG. 7B for each depicted library.
Figure 7A:
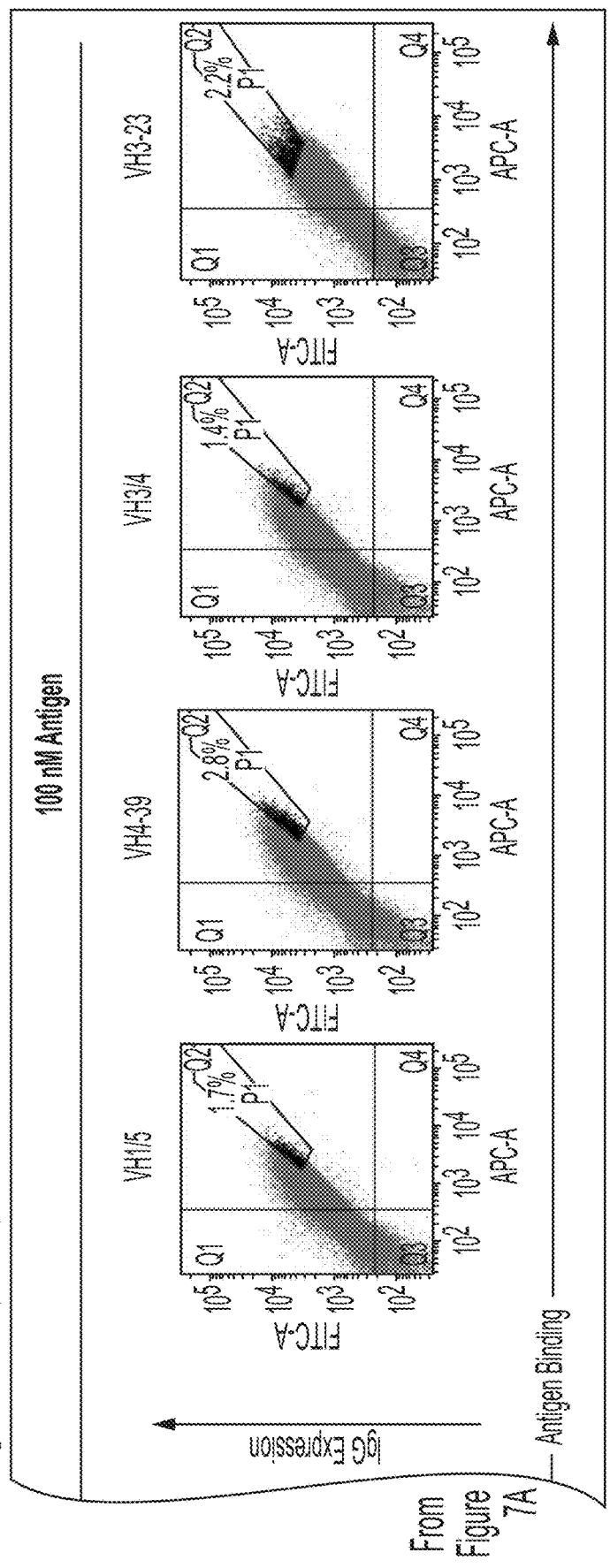
Figure 7B:
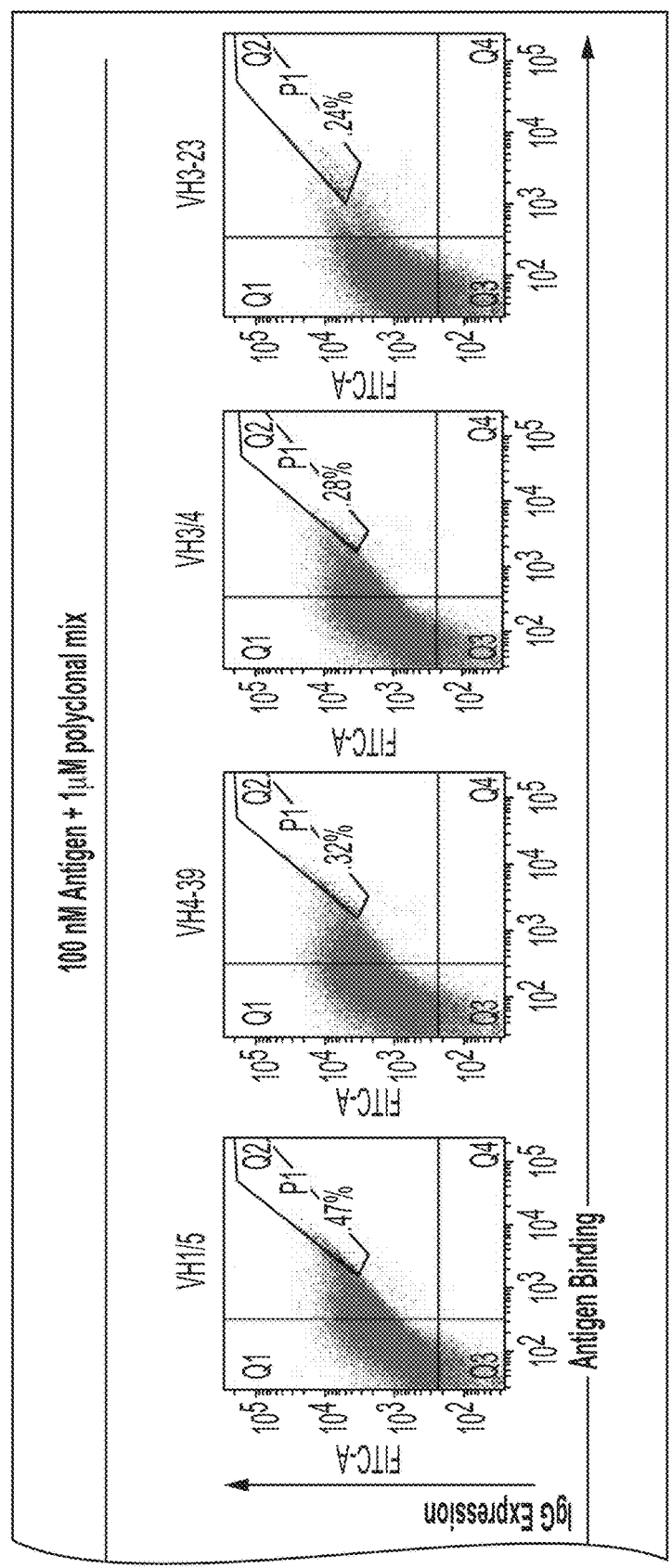

In this example, in order to prepare compositions comprising polyclonal antibody mixtures, yeast populations from round 4 selection outputs were induced to secrete soluble antibodies, and the secreted antibodies were purified over a Protein A column. To block dominant epitopes during selections, the polyclonal antibody mixtures were pre-incubated with the target antigen and then added to the corresponding round 3 library selection output. For all eight libraries, a significant reduction in antigen-binding signal was observed after pre-complexing the antigen with the polyclonal antibodies, suggesting that the soluble antibodies were competing with a large fraction of the population of binders (compare FIG. 7B to FIG. 7A). Sort gates were drawn to select clones that retained antigen-binding in the presence of the polyclonal antibodies, as these clones were likely to bind non-dominant (i.e., "rare") epitopes. CDR H3 sequence analysis of 176 individual clones isolated from these selections indicated that 76 unique antibodies representing 15 germline gene families were rescued (FIG. 2B). Notably, only 13 of these clones were previously identified in the initial round 4 selection outputs.

Figure 8A:
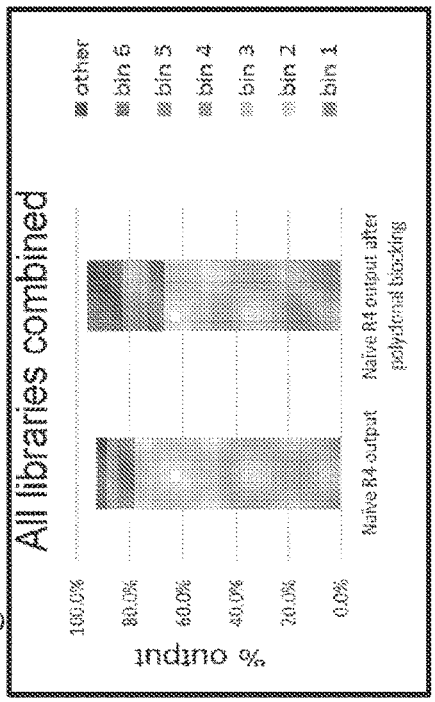
FIGS. 8A and 8B each depict epitopic coverage for selection outputs in the absence and presence of the polyclonal antibody mixture, as described in the Examples.
Figure 8B:
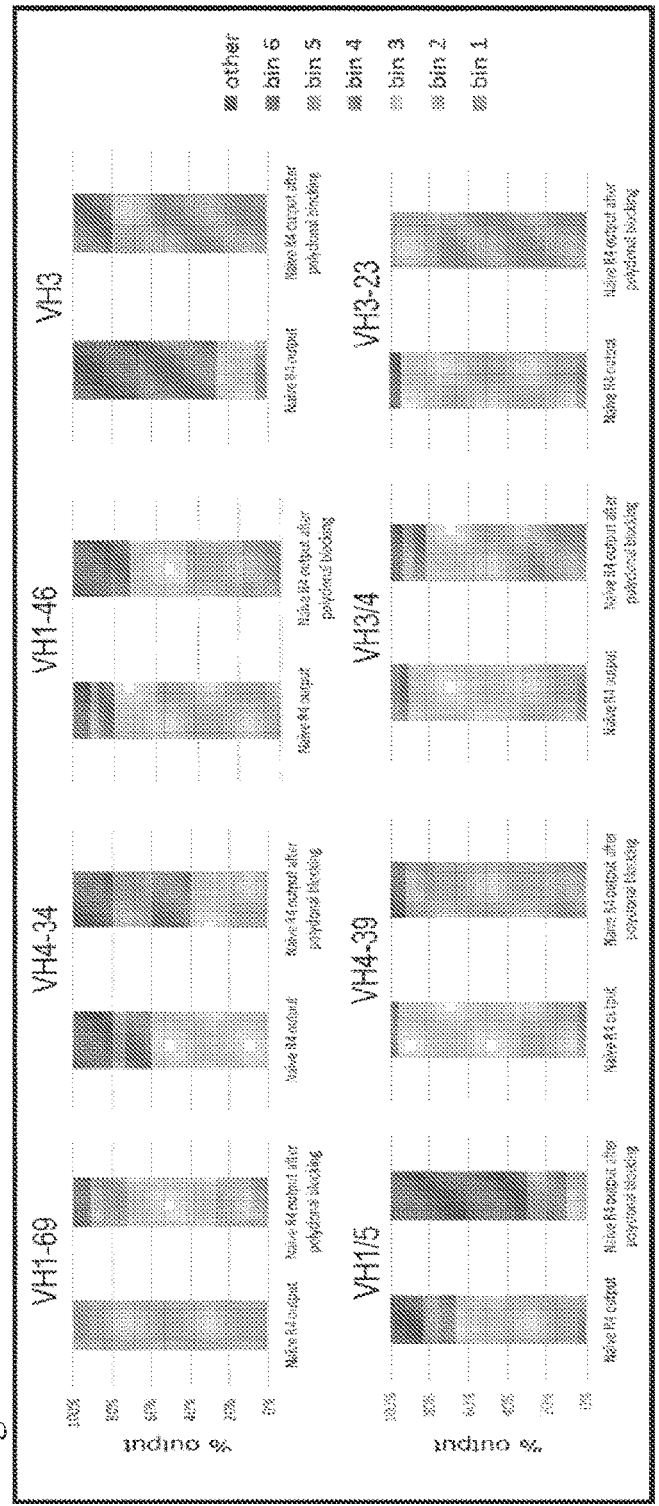

Selections Performed with Compositions Comprising Polyclonal Antibody Mixtures Promote Recovery of Clones Against Rare Epitopes Antibody cross-competition assays were performed on the recovered clones for comparison with the results obtained from the initial round 4 selection outputs. Analysis of the results from all unique clones from the eight libraries showed that the polyclonal mixture blocking selection strategy resulted in a significantly less biased epitope distribution compared to the original selections (FIG. 8A). These differences were even more dramatic when the epitope distributions of the eight individual germline libraries were analyzed separately (FIG. 8B).

Figure 9A:
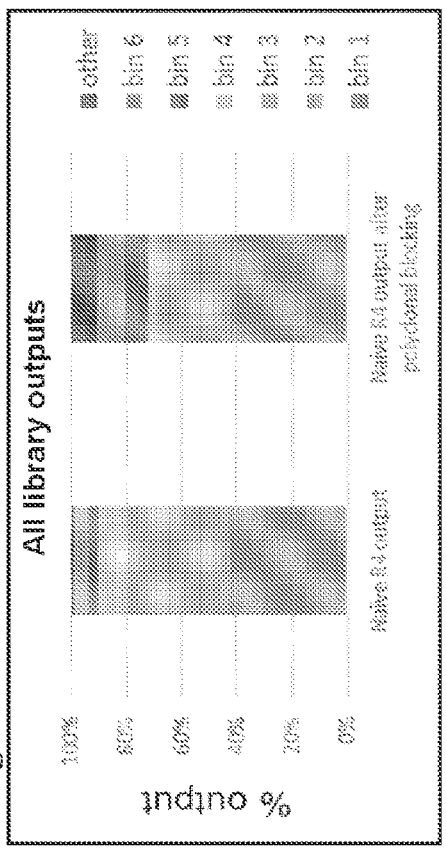
FIGS. 9A and 9B provide an epitopic coverage analysis of the results depicted in FIGS. 8A and 8B, but based on total sequence output. Epitopic representation is shown for round 4 selection outputs in the absence (left columns) and presence (right columns) of the polyclonal antibody mixtures.
Figure 9B:
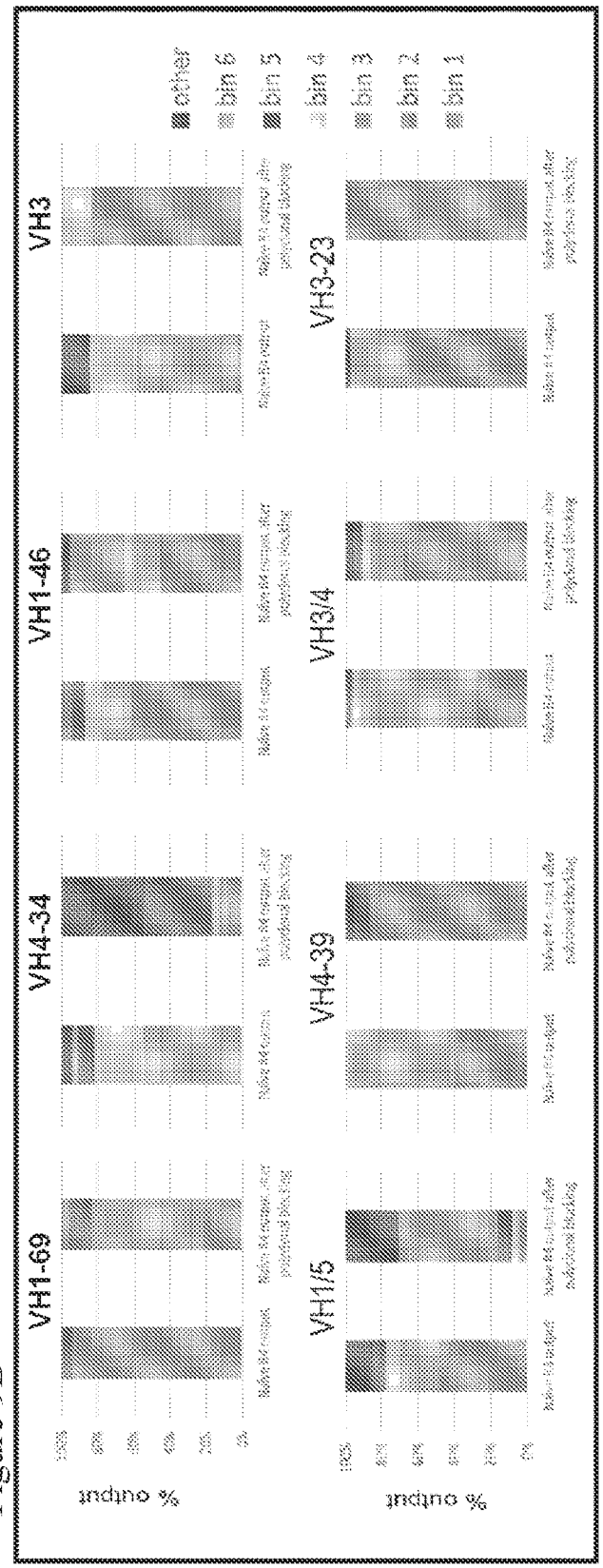
Figure 10:
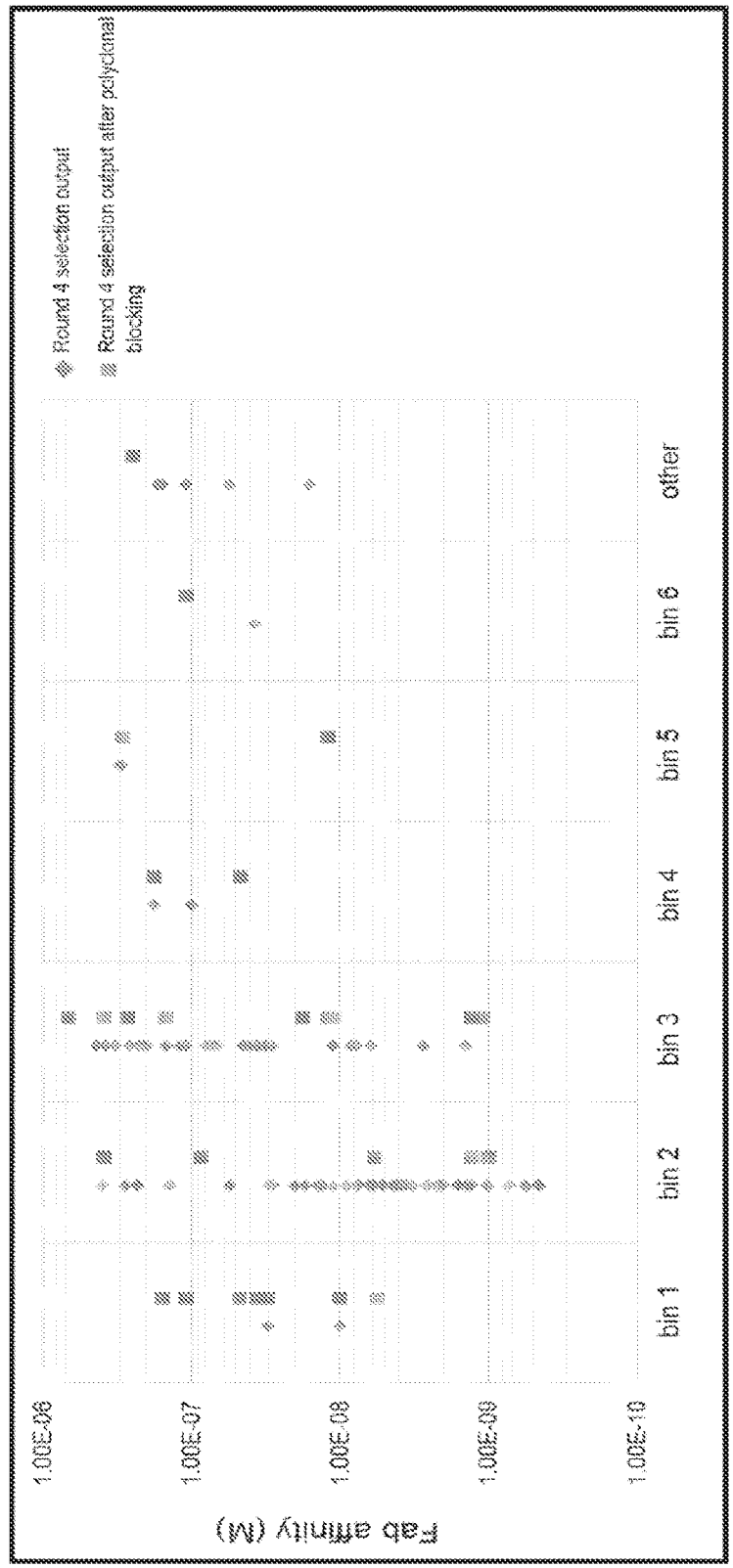
FIG. 10 depicts binding affinities of antibodies selected in the absence (blue diamonds) or presence (orange squares) of the polyclonal antibodies mixtures. Fab affinities are plotted for clones isolated from initial selections and for clones isolated from selections after employing the polyclonal antibody mixtures. Equilibrium affinity measurements were determined using MSD, and the data are representative of two independent experiments, as described in the Examples. A fraction of lower affinity clones consistently showed high data scatter and are therefore not shown on the plot.

For instance, the initial round 4 output of the VH1-69 library was dominated by clones in two bins, with bin 2 representing 92% of the output. However, when this library was re-interrogated after pre-blocking the antigen with the polyclonal antibody mixture, the epitope distribution was increased to 5 different bins, with bin 2 only representing 17% of the output. In other cases, blocking with the polyclonal antibody mixture skewed the epitope distribution toward epitopes that were under-represented in the initial selection output. For example, whereas clones in bins 2 and 3 dominated the initial VH1/5 library selections, re-interrogation of this library after pre-blocking the antigen with the polyclonal antibody mixture biased the selection toward clones in bin 6 and other rare bins. Similar trends were observed when the results were analyzed by total sequence output rather than unique clones (FIG. 9A for data presented for all libraries combined and FIG. 9B for data presented for each individual library). Importantly, the binding affinities of the clones recovered from the selections that had been competed with polyclonal antibody mixtures were comparable to those isolated from the original selections (FIG. 10).

Accordingly, the use of the polyclonal mixture demonstrated, for example, that such use yielded antibodies having specificities for the antigen, wherein the binding specificities of the antibodies were indicative of: broadening of epitopic coverage of the antigen, normalization of epitopic coverage of the antigen, reduction of selection bias towards at least one dominant epitope of the antigen, blockage of at least one dominant epitope of the antigen, enrichment of antibodies for at least one rare epitope of the antigen, and the identification of antibodies having specificity for at least one rare epitope, and the identification of a greater number of antibodies collectively having specificities for a greater number of epitopes relative to the number of antibodies identified against the antigen of interest in selections in which polyclonal mixtures were not employed.

Discussion

In recent years, antibody display technology has emerged as a leading method for the isolation and characterization of monoclonal antibodies. However, one of the major limitations of library technology is that, in the absence of control reagents of defined specificity, it is often difficult to control the epitope representation of selection outputs. Under these circumstances, it is usually necessary to isolate and characterize large numbers of binders in order to identify functional clones. To overcome this limitation, as disclosed throughout, Applicants have developed general strategies to more efficiently interrogate antibody repertoires by broadening epitopic coverage, normalizing epitopic coverage, reducing selection bias towards dominant epitopes, blocking dominant epitopes, enriching for antibodies having specificity for rare epitopes, and increasing the recovery of clones for rare epitopes, by preparing soluble polyclonal antibody mixtures from selection outputs and using them to block dominant epitopes during reinterrogation of the library repertoires. Without wishing to be bound by any theory, it is believed clones targeting dominant epitopes often comprise a large fraction of the polyclonal mixtures, and these epitopes are efficiently blocked by the polyclonal mixtures when contacted with the antigen of interest and therefore be unavailable for binding by yeast library clones upon reinterrogation.

Using an exemplary antigen and yeast library technology as described above, Applicants have demonstrated that this strategy effectively counteracts epitope bias in selection outputs. In initial selections, it was found that clones targeting two epitopes comprised approximately 75% of the selection output, whereas clones targeting five other epitopes only represented 1-7% of the output. However, after pre-blocking the antigen with the polyclonal antibody mixtures and reinterrogating the libraries, the epitope distribution was significantly less skewed, with each of the seven bins comprising 5-28% of the output. Interestingly, however, when the results were analyzed for each of the eight germline-specific libraries separately, we found that the outcome of the polyclonal antibody blocking approach varied considerably. For some libraries, the new method resulted in a less biased epitope distribution, but clones targeting new epitopes were not identified. In other cases, the new method dramatically skewed the epitope distribution toward clones targeting novel epitopes and away from clones targeting dominant epitopes. Importantly, given that clones against dominant epitopes were de-enriched using these methods, combining this strategy with traditional selection protocols maximizes epitope breadth in selection outputs.

Furthermore, although yeast technology was employed for these exemplary studies, these methods may be readily applied to any platform in which soluble antibodies can be directly secreted from the selection system (Horlick et al., 2013, Mazor et al., 2007, Nett et al., 2013, Rakestraw et al., 2011). In cases where direct antibody secretion is not feasible, an alternative approach may be to use polyclonal sera from immunized animals to block immunodominant epitopes.

Additionally, this approach compares favorably to other approaches requiring deep-sequencing singly screened phage display libraries (Ravn et al., 2010) or animal repertoires (Reddy et al., 2010) followed by synthesis of the genes of those clones found to be represented multiple times in the library and therefore inferred to be antigen-specific. Advantageously, the speed and biochemically direct assessment of epitope cross-blocking phenotypes demonstrates the superiority of the inventive methods disclosed throughout relative to such deep sequencing methods both in terms of the significantly higher throughput afforded by the inventive methods and diminished propensity for error characteristic of deep sequencing methodologies.

REFERENCES

Batista F. D. and Neuberger M. S. (1998) *Immunity*, 8, 751-759. First published on 1998 Jul. 9.

Boder E. T., Midelfort K. S. and Wittrup K. D. (2000) *Proceedings of the National Academy of Sciences of the United States of America*, 97, 10701-10705. First published on 2000 Sep. 14, doi: 10.1073/pnas.170297297.

Boder E. T. and Wittrup K. D. (1997) *Nature biotechnology*, 15, 553-557. First published on 1997 Jun. 1, doi: 10.1038/nbt0697-553.

Bostrom J., Lee C. V., Haber L. and Fuh G. (2009) *Methods in molecular biology*, 525, 353-376, xiii. First published on 2009 Mar. 3, doi: 10.1007/978-1-59745-554-1_19.

Bostrom J., Yu S. F., Kan D., Appleton B. A., Lee C. V., Billeci K., Man W., Peale F., Ross S., Wiesmann C. et al. (2009) *Science*, 323, 1610-1614. First published on 2009 Mar. 21, doi: 10.1126/science.1165480.

Bowley D. R., Labrijn A. F., Zwick M. B. and Burton D. R. (2007) *Protein engineering, design & selection: PEDS*, 20, 81-90. First published on 2007 Jan. 24, doi: 10.1093/protein/gz1057.

Bradbury A. R., Sidhu S., Dubel S. and McCafferty J. (2011) *Nature biotechnology*, 29, 245-254. First published on 2011 Mar. 11, doi: 10.1038/nbt.1791.

Bueno L. L., Lobo F. P., Morais C. G., Mourao L. C., de Avila R. A., Soares I. S., Fontes C. J., Lacerda M. V., Chavez Olortegui C., Bartholomeu D. C. et al. (2011) *PloS one*, 6, e21289. First published on 2011 Jun. 30, doi: 10.1371/journal.pone.0021289.

Caton A. J., Brownlee G. G., Yewdell J. W. and Gerhard W. (1982) *Cell*, 31, 417-427. First published on 1982 Dec. 1.

Decker J. M., Bibollet-Ruche F., Wei X., Wang S., Levy D. N., Wang W., Delaporte E., Peeters M., Derdeyn C. A., Allen S. et al. (2005) *The Journal of experimental medicine*, 201, 1407-1419. First published on 2005 May 4, doi: 10.1084/jem.20042510.

DeLano W. L., Ultsch M. H., de Vos A. M. and Wells J. A. (2000) *Science*, 287, 1279-1283. First published on 2000 Feb. 26.

Deng L., Zhong L., Struble E., Duan H., Ma L., Harman C., Yan H., Virata-Theimer M. L., Zhao Z., Feinstone S. et al. (2013) *Proceedings of the National Academy of Sciences of the United States of America*, 110, 7418-7422. First published on 2013 Apr. 17, doi: 10.1073/pnas.1305306110.

Ditzel H. J., Binley J. M., Moore J. P., Sodroski J., Sullivan N., Sawyer L. S., Hendry R. M., Yang W. P., Barbas C. F., 3rd and Burton D. R. (1995) *Journal of immunology*, 154, 893-906. First published on 1995 Jan. 15.

Ekiert D. C. and Wilson I. A. (2012) *Current opinion in virology*, 2, 134-141. First published on 2012 Apr. 10, doi: 10.1016/j.coviro.2012.02.005.

Estep P., Reid F., Nauman C., Liu Y., Sun T., Sun J. and Xu Y. (2013) *mAbs*, 5, 270-278. First published on 2013 Apr. 12, doi: 10.4161/mabs.23049.

Fagete S., Rousseau F., Magistrelli G., Gueneau F., Ravn U., Kosco-Vilbois M. H. and Fischer N. (2012) *The Journal of biological chemistry*, 287, 1458-1467. First published on 2011 Nov. 2, doi: 10.1074/jbc.M111.253658.

Feldhaus M. J., Siegel R. W., Opresko L. K., Coleman J. R., Feldhaus J. M., Yeung Y. A., Cochran J. R., Heinzelman P., Colby D., Swers J. et al. (2003) *Nature biotechnology*, 21, 163-170. First published on 2003 Jan. 22, doi: 10.1038/nbt785.

Felding-Habermann B., Lerner R. A., Lillo A., Zhuang S., Weber M. R., Arrues S., Gao C., Mao S., Saven A. and Janda K. D. (2004) *Proceedings of the National Academy of Sciences of the United States of America*, 101, 17210-17215. First published on 2004 Nov. 26, doi: 10.1073/pnas.0407869101.

Foote J. and Eisen H. N. (2000) *Proceedings of the National Academy of Sciences of the United States of America*, 97, 10679-10681. First published on 2000 Sep. 27.

Fuh G. (2007) *Expert opinion on biological therapy*, 7, 73-87. First published on 2006 Dec. 8, doi: 10.1517/14712598.7.1.73.

Garcia-Rodriguez C., Geren I. N., Lou J., Conrad F., Forsyth C., Wen W., Chakraborti S., Zao H., Manzanarez G., Smith T. J. et al. (2011) *Protein engineering, design & selection: PEDS*, 24, 321-331. First published on 2010 Dec. 15, doi: 10.1093/protein/gzq111.

Hanes J., Schaffitzel C., Knappik A. and Pluckthun A. (2000) *Nature biotechnology*, 18, 1287-1292. First published on 2000 Dec. 2, doi: 10.1038/82407.

Hawkins R. E., Russell S. J. and Winter G. (1992) *Journal of molecular biology*, 226, 889-896. First published on 1992 Aug. 5.

Hoogenboom H. R. (2005) *Nature biotechnology*, 23, 1105-1116. First published on 2005 Sep. 10, doi: 10.1038/nbt1126.

Horlick R. A., Macomber J. L., Bowers P. M., Neben T. Y., Tomlinson G. L., Krapf I. P., Dalton J. L., Verdino P. and King D. J. (2013) *The Journal of biological chemistry*. First published on 2013 May 22, doi: 10.1074/jbc.M113.452482.

Kong L., Giang E., Robbins J. B., Stanfield R. L., Burton D. R., Wilson I. A. and Law M. (2012) *Proceedings of the National Academy of Sciences of the United States of America*, 109, 9499-9504. First published on 2012 May 25, doi: 10.1073/pnas.1202924109.

Kwong P. D. and Mascola J. R. (2012) *Immunity*, 37, 412-425. First published on 2012 Sep. 25, doi: 10.1016/j.immuni.2012.08.012.

Kwong P. D. and Wilson I. A. (2009) *Nature immunology*, 10, 573-578. First published on 2009 May 19, doi: 10.1038/ni.1746.

Lou J., Geren I., Garcia-Rodriguez C., Forsyth C. M., Wen W., Knopp K., Brown J., Smith T., Smith L. A. and Marks J. D. (2010) *Protein engineering, design & selection: PEDS*, 23, 311-319. First published on 2010 Feb. 17, doi: 10.1093/protein/gzq001.

Mazor Y., Van Blarcom T., Mabry R., Iverson B. L. and Georgiou G. (2007) *Nature biotechnology*, 25, 563-565. First published on 2007 Apr. 17, doi: 10.1038/nbt1296.

Nett J. H., Cook W. J., Chen M. T., Davidson R. C., Bobrowicz P., Kett W., Brevnova E., Potgieter T. I., Mellon M. T., Prinz B. et al. (2013) *PloS one*, 8, e68325. First published on 2013 Jul. 11, doi: 10.1371/journal.pone.0068325.

Pavoor T. V., Wheasler J. A., Kamat V. and Shusta E. V. (2012) *Protein engineering, design & selection: PEDS*, 25, 625-630. First published on 2012 Jul. 7, doi: 10.1093/protein/gzs041.

Rakestraw J. A., Aird D., Aha P. M., Baynes B. M. and Lipovsek D. (2011) *Protein engineering, design & selection: PEDS*, 24, 525-530. First published on 2011 Mar. 16, doi: 10.1093/protein/gzr008.

Ravn U., Gueneau F., Baerlocher L., Osteras M., Desmurs M., Malinge P., Magistrelli G., Farinelli L., Kosco-Vilbois M. H. and Fischer N. (2010) *Nucleic acids research*, 38, e193. First published on 2010 Sep. 18, doi: 10.1093/nar/gkq789.

Reddy S. T., Ge X., Miklos A. E., Hughes R. A., Kang S. H., Hoi K. H., Chrysostomou C., Hunicke-Smith S. P., Iverson B. L., Tucker P. W. et al. (2010) *Nature biotechnology*, 28, 965-969. First published on 2010 Aug. 31, doi: 10.1038/nbt.1673.

Schaefer G., Haber L., Crocker L. M., Shia S., Shao L., Dowbenko D., Totpal K., Wong A., Lee C. V., Stawicki S.

et al. (2011) *Cancer cell,* 20, 472-486. First published on 2011 Oct. 22, doi: 10.1016/j.ccr.2011.09.003.

Siegel R. W., Coleman J. R., Miller K. D. and Feldhaus M. J. (2004) *Journal of immunological methods,* 286, 141-153. First published on 2004 Apr. 17, doi: 10.1016/j.jim.2004.01.005.

Traxlmayr M. W., Lobner E., Antes B., Kainer M., Wiederkum S., Hasenhindl C., Stadlmayr G., Ruker F., Woisetschlager M., Moulder K. et al. (2013) *Protein engineering, design & selection: PEDS,* 26, 255-265. First published on 2012 Dec. 26, doi: 10.1093/protein/gzs102.

Winter G., Griffiths A. D., Hawkins R. E. and Hoogenboom H. R. (1994) *Annual review of immunology,* 12, 433-455. First published on 1994 Jan. 1, doi: 10.1146/annurev.iy.12.040194.002245.

Xu Y., Roach, W., Sun T., Jain T., Prinz B., Yu T., Torrey J., Thomas J., Bobrowicz P., Vasquez M., Wittrup, $K_D$., Krauland E (2013) *Protein engineering, design & selection: PEDS.* Published online. doi:10.1093/protein/gzt047.

What is claimed is:

1. A method of identifying an antibody with specificity for a rare epitope on an antigen, the method comprising:
   (a) contacting a first sample of the antigen with a first plurality of antibodies and identifying antibodies from among the first plurality of antibodies with specificity for a dominant epitope on the antigen;
   (b) contacting a second sample of the antigen with antibodies identified in step (a) and a second plurality of antibodies; and
   (c) identifying an antibody from the second plurality of antibodies with specificity for the rare epitope on the antigen.

2. The method of claim 1, wherein the first and/or second plurality of antibodies comprise a library of antibodies.

3. The method of claim 2, wherein the library of antibodies comprises a phage library or is associated with host cells.

4. The method of claim 3, wherein the library is associated with host cells comprising one or more of prokaryotic cells, eukaryotic cells, bacteria, *E. coli*, and yeast.

5. The method of claim 4, wherein the host cells comprise yeast comprising *Saccharomyces cerevisiae* and/or *Pichia pastoris*.

6. The method of claim 1, wherein the first and second plurality of antibodies comprise the same antibodies.

7. The method of claim 1, wherein the first and second plurality of antibodies consist essentially of the same antibodies.

8. The method of claim 1, wherein the first and second plurality of antibodies consist of the same antibodies.

9. The method of claim 1, wherein the second plurality of antibodies comprises a subset of antibodies comprised by the first plurality of antibodies.

10. The method of claim 1, wherein identifying antibodies in step a) and/or step c) comprises the use of flow cytometry.

11. The method of claim 10, wherein the flow cytometry comprises florescence-activated cell sorting (FACS) and/or magnetic assisted cell sorting (MACS).

12. The method of claim 1, wherein the first and/or second plurality of antibodies comprise one or more of full length immunoglobulins; full length IgGs; full length IgMs; full length IgEs; full length IgAs; variable domains; antibody fragments; linear antibodies; single chain antibodies; scFvs; Fv fragments; Fab fragments, Fab' fragments, (Fab')$_2$ fragments; multispecific antibodies; bispecific antibodies; trispecific antibodies; tetraspecific antibodies; humanized antibodies; and combinations thereof.

13. The method of claim 1, wherein step (b) comprises pre-incubating the second sample of the antigen with antibodies identified in step (a) before contacting the second sample of the antigen with the second plurality of antibodies.

14. The method of claim 13, wherein the second plurality of antibodies is associated with a plurality of host cells used to express the second plurality of antibodies.

15. The method of claim 14, wherein the plurality of host cells comprises eukaryotic cells.

16. The method of claim 15, wherein the eukaryotic cells comprise yeast cells.

* * * * *

SEQUENCE LISTING

```
<160> NUMBER OF SEQ ID NOS: 16

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Glu Tyr Phe Gln His
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Tyr Phe Gln His
1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Phe Gln His
1

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Trp Tyr Phe Asp Leu
1               5

<210> SEQ ID NO 5
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 5

Trp Tyr Phe Asp Leu
1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Phe Asp Leu
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Phe Asp Val
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Phe Asp Tyr
1

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Trp Phe Asp Ser
1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Trp Phe Asp Ser
1
```

```
<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Tyr Tyr Tyr Tyr Gly Met Asp Val
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Tyr Tyr Tyr Gly Met Asp Val
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Tyr Tyr Gly Met Asp Val
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Tyr Gly Met Asp Val
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Gly Met Asp Val
1               5

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 16

Gly Met Asp Val
1
```